(12) United States Patent
Shen et al.

(10) Patent No.: US 10,173,984 B2
(45) Date of Patent: Jan. 8, 2019

(54) DNA2 INHIBITORS FOR CANCER TREATMENT

(71) Applicants: City of Hope, Duarte, CA (US); California Institute of Technology, Pasadena, CA (US)

(72) Inventors: Binghui Shen, La Verne, CA (US); Judith Campbell, Pasadena, CA (US); Li Zheng, Arcadia, CA (US); Hongzhi Li, Duarte, CA (US); David Horne, Duarte, CA (US); Jun Xie, Duarte, CA (US); Kenneth Karanja, Maple Grove, MN (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 15/866,268

(22) Filed: Jan. 9, 2018

(65) Prior Publication Data

US 2018/0134664 A1 May 17, 2018

Related U.S. Application Data

(63) Continuation of application No. 15/428,021, filed on Feb. 8, 2017, now Pat. No. 9,932,310.

(60) Provisional application No. 62/292,506, filed on Feb. 8, 2016.

(51) Int. Cl.
| | |
|---|---|
| *C07D 215/56* | (2006.01) |
| *A61K 31/47* | (2006.01) |
| *A61K 45/06* | (2006.01) |

(52) U.S. Cl.
CPC ............ *C07D 215/56* (2013.01); *A61K 31/47* (2013.01); *A61K 45/06* (2013.01)

(58) Field of Classification Search
CPC .................................................... C07D 215/56
USPC ......................................................... 546/152
See application file for complete search history.

(56) References Cited

U.S. PATENT DOCUMENTS 9,932,310 B2  4/2018  Shen et al.

OTHER PUBLICATIONS

Wason, Nanomedicine: Nanotechnology, Biology, and Medicine 9 (2013) 558-569.*
Pasquini, J. Med. Chem. 2011, 54, 5444-5453.*
Abdul-Ahad. Eur. J. Med. Chem. 1982, 17(4), 301-306.*
Balakrishnan, L. et al. (Dec. 10, 2010, e-published Oct. 6, 2010). "Dna2 exhibits a unique strand end-dependent helicase function," *J Biol Chem* 285(50):38861-38868.
Begg, A.C. et al. (Apr. 2011). "Strategies to improve radiotherapy with targeted drugs," *Nat Rev Cancer* 11(4):239-253.
Budd, M.E. et al. (Apr. 28, 2000). "The pattern of sensitivity of yeast dna2 mutants to DNA damaging agents suggests a role in DSB and postreplication repair pathways," *Mutat Res* 459(3):173-186.
Budd, M.E. et al. (Dec. 2005, e-published Dec. 2, 2005). "A network of multitasking proteins at the DNA replication fork preserves genome stability," *PLoS Genet* 1(6):e61.
Chen, M.C. et al. (Jun. 2015, e-published Mar. 26, 2015). "The Novel Ribonucleotide Reductase Inhibitor COH29 Inhibits DNA Repair in Vitro," *Mol Pharmacol* 87(6):996-1005.
Chou, T.C. (Jan. 15, 2010, e-published Jan. 12, 2010). "Drug combination studies and their synergy quantification using the Chou-Talalay method," *Cancer Res* 70(2):440-446.
Duxin, J.P. et al. (Jun. 22, 2012, e-published May 7, 2012). "Okazaki fragment processing-independent role for human Dna2 enzyme during DNA replication," *J Biol Chem* 287(26):21980-21991.
Fathers, C. et al. (Mar. 1, 2012, e-published Mar. 1, 2012). "Inhibition of poly(ADP-ribose) glycohydrolase (PARG) specifically kills BRCA2-deficient tumor cells," *Cell Cycle* 11(5):990-997.
Higgs, M.R. et al. (Aug. 6, 2015, e-published Jul. 9, 2015). "BOD1L is Required to Suppress Deleterious Resection of Stressed Replication Forks," *Mol Cell* 59(3):462-477.
Howard, S.M. et al. (Jan. 28, 2015). "DNA damage response factors from diverse pathways, including DNA crosslink repair, mediate alternative end joining," *PLoS Genet* 11(1):e1004943.
Hu, Y. et al. (Dec. 2014, e-published Sep. 24, 2014). "PARP1-driven poly-ADP-ribosylation regulates BRCA1 function in homologous recombination-mediated DNA repair," *Cancer Discov* 4(12):1430-1447.
Kang, Y.H. et al. (Apr. 2010). "Dna2 on the road to Okazaki fragment processing and genome stability in eukaryotes," *Crit Rev Biochem Mol Biol* 45(2):71-96.
Kao, H.I. et al. (Dec. 3, 2004, e-published Sep. 22, 2004). "Dna2p helicase/nuclease is a tracking protein, like FEN1, for flap cleavage during Okazaki fragment maturation," *J Biol Chem* 279(49):50840-50849.
Karanja, K.K. et al. (Nov. 1, 2012, e-published Sep. 17, 2012). "DNA2 and EXO1 in replication-coupled, homology-directed repair and in the interplay between HDR and the FA/BRCA network," *Cell Cycle* 11(21):3983-3996.
Karanja, K.K. et al. (2014, e-published Mar. 12, 2014). "Preventing over-resection by DNA2 helicase/nuclease suppresses repair defects in Fanconi anemia cells," *Cell Cycle* 13(10):1540-1550.
Kumar, S. et al. (Feb. 1, 2013, e-published Jan. 25, 2013). "Lagging strand maturation factor Dna2 is a component of the replication checkpoint initiation machinery," *Genes Dev* 27(3):313-321.
Lai, M.S. et al. (Jun. 8, 2012). "Dna2 offers support for stalled forks," *Cell* 149(6):1181-1183.
Masuda-Sasa, T. et al. (Apr. 4, 2006). "Biochemical analysis of human Dna2," *Nucleic Acids Res* 34(6):1865-1875.
Masuda-Sasa, T. et al. (Sep. 5, 2008, e-published Jun. 30, 2008). "Processing of G4 DNA by Dna2 helicase/nuclease and replication protein A (RPA) provides insights into the mechanism of Dna2/RPA substrate recognition," *J Biol Chem* 283(36):24359-24373.
Nimonkar, A.V. et al. (Feb. 15, 2011). "BLM-DNA2-RPA-MRN and EXO1-BLM-RPA-MRN constitute two DNA end resection machineries for human DNA break repair," *Genes Dev* 25(4):350-362.
Peng, G. et al. (Jun. 1, 2012, e-published Apr. 9, 2012). "Human nuclease/helicase DNA2 alleviates replication stress by promoting DNA end resection," *Cancer Res* 72(11):2802-2813.

(Continued)

*Primary Examiner* — Nizal S Chandrakumar
(74) *Attorney, Agent, or Firm* — Mintz Levin Cohn Ferris Glovsky and Popeo, P.C.

(57) ABSTRACT

Disclosed herein, inter alia, are compositions and methods for inhibiting DNA2.

8 Claims, 22 Drawing Sheets

(56) References Cited

OTHER PUBLICATIONS

Strauss, C. et al. (Oct. 15, 2014). "The DNA2 nuclease/helicase is an estrogen-dependent gene mutated in breast and ovarian cancers," Ocotarget 5(19):9396-9409.

Thangavel, S. et al. (Mar. 2, 2015). "DNA2 drives processing and restart of reversed replication forks in human cells," *J Cell Biol* 208(5):545-562.

Weitao, T. et al. (2003). "Dna2 Helicase/Nuclease Causes Replicative Fork Stalling and Double-strand Breaks in the Ribosomal DNA of *Saccharomyces cerevisiae*," *The Journal of Biological Chemistry* 278(25):22513-22522.

Weitao, T. et al. (Nov. 2003). "Evidence that yeast SGS1, DNA2, SRS2, and FOB1 interact to maintain rDNA stability," *Mutat Res* 532(1-2):157-172.

Zhou, B. et al. (Nov. 1, 2013, e-published Sep. 26, 2013). "A small-molecule blocking ribonucleotide reductase holoenzyme formation inhibits cancer cell growth and overcomes drug resistance," *Cancer Res* 73(21):6484-6493.

Zou, L. et al. (Jun. 6, 2003). "Sensing DNA damage through ATRIP recognition of RPA-ssDNA complexes," *Science* 300(5625):1542-1548.

* cited by examiner 4-hydroxy-8-nitroquinoline-3-carboxylic acid

FIG. 2D
FIG. 2E
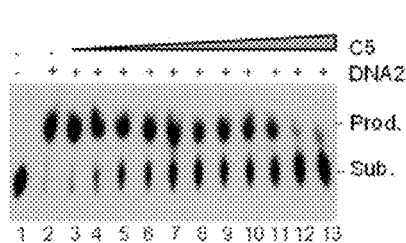
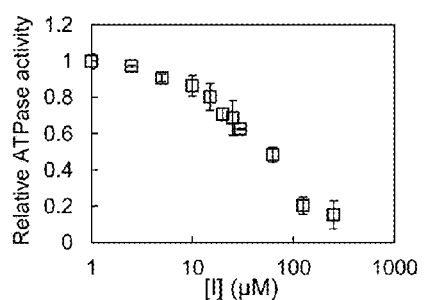
FIG. 2F
FIG. 2G
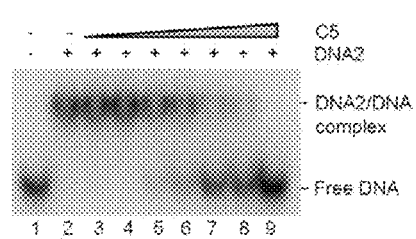
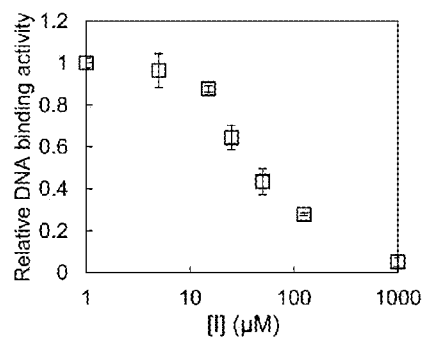
FIG. 3A
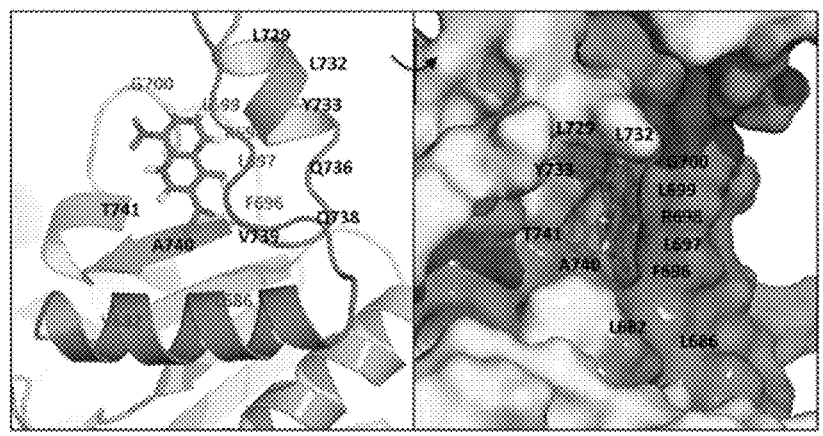

FIG. 3B
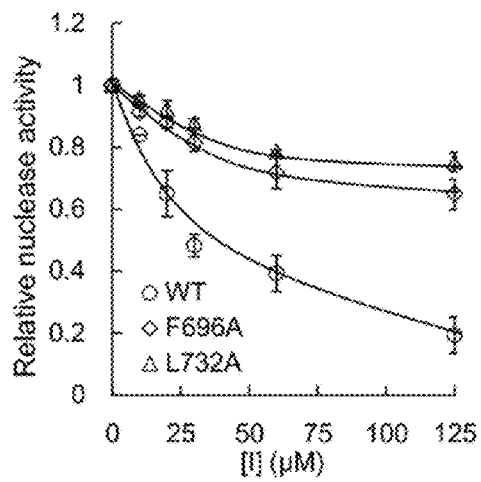
FIG. 3C
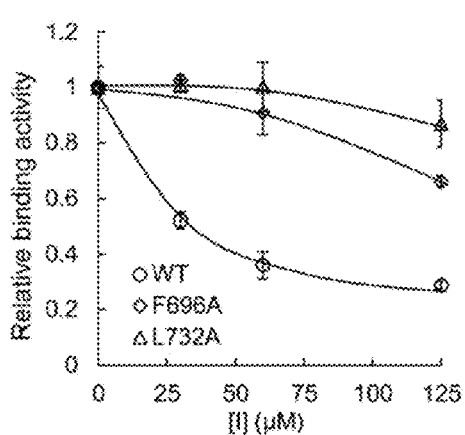
FIG. 4A
| Origins | Cell lines | IC50 (µM) |
|---|---|---|
| Breast | MCF10A | 24.4 |
|  | MCF7 | 7.2 |
|  | MDA-MB-231 | 46.8 |
| Colon | FHC | 75.2 |
|  | DLD-1 | 25.1 |
|  | HCT-8 | 27.5 |
|  | HT-29 | 40.5 |
|  | HCT116 | 24.2 |
|  | WiDr | 52.6 |
| Prostate | RWPE-1 | 78.8 |
|  | PC3 | 20.9 |
|  | C4-2 | 19.7 |
|  | 22RV1 | 11.8 |
|  | CWRR1 | 15.7 |
| Lung | IMR90 | 95.5 |
|  | A549 | 23.6 |
|  | H460 | 43.7 |
|  | H2030 | 17.7 |

DNA2 INHIBITORS FOR CANCER TREATMENT

CROSS-REFERENCES TO RELATED APPLICATIONS

This application is a continuation of application Ser. No. 15/428,021 filed Feb. 8, 2017 which claims the benefit of U.S. Provisional Application No. 62/292,506, filed Feb. 8, 2016, which is incorporated herein by reference in entirety and for all purposes.

STATEMENT AS TO RIGHTS TO INVENTIONS MADE UNDER FEDERALLY SPONSORED RESEARCH AND DEVELOPMENT

This invention was made with Government support under Grant No. CA085344 and GM078666 awarded by the National Institutes of Health and Grant No. W81XWH-09-1-0041 awarded by the United States Army. The Government has certain rights in the invention.

BACKGROUND

DNA replication is the central process of all actively dividing cells. Blocking this process can result in cell cycle arrest, senescence, and apoptosis. Therefore, DNA replication forks are the targets of most cancer chemotherapeutics. However, a drawback of these therapies is that the cancer cell may become resistant to the radiation or chemotherapy. One major conserved DNA repair enzymes is the DNA2 helicase/nuclease (DNA2). Compounds for reducing or inhibiting the repairing functions of DNA2 remains elusive. Disclosed herein, inter alia, are solutions to these and other problems in the art.

BRIEF SUMMARY OF THE INVENTION

The disclosure provides a compound, or pharmaceutically acceptable salt thereof, having the formula:

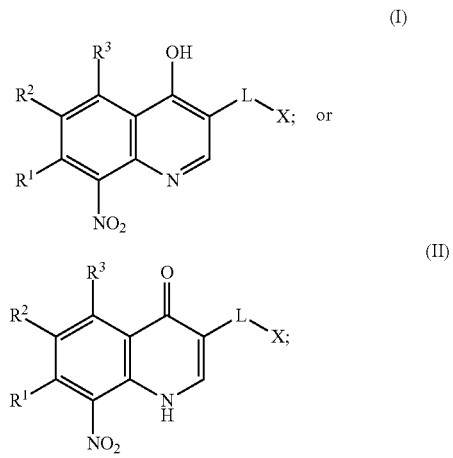

wherein the substituents are as defined herein.

The disclosure provides methods of treating cancer and Fanconi anemia using the compounds of Formula (I) or (II); methods of treating cancer and Fanconi anemia using the compounds of Formula (I) or (II) in conjunction with chemotherapeutic agents, radiation, or a combination thereof; methods of sensitizing cancer cells to radiation or chemotherapy using the compounds of Formula (I) or (II) in conjunction with radiation or chemotherapeutic agents; methods of inhibiting DNA replication using the compounds of Formula (I) or (II); methods of suppressing DNA double-strand break repair end resection, recombination, over-resection of nascent DNA in cells defective in fork protection using the compounds of Formula (I) or (II); restarting stalled DNA replication forks in cells using the compounds of Formula (I) or (II); and interfering with telomere replication or repair using the compounds of Formula (I) or (II).

The disclosure provides pharmaceutical compositions containing compounds of Formula (I) or (II); methods of treating cancer and Fanconi anemia using these pharmaceutical compositions; methods of treating cancer and Fanconi anemia using these pharmaceuticals compositions in conjunction with chemotherapeutic agents, radiation, or a combination thereof; methods of sensitizing cancer cells to radiation or chemotherapy using these pharmaceutical compositions in conjunction with radiation or chemotherapeutic agents; methods of inhibiting DNA replication using these pharmaceutical compositions; methods of suppressing DNA double-strand break repair end resection, recombination, over-resection of nascent DNA in cells defective in fork protection using these pharmaceutical compositions; restarting stalled DNA replication forks in cells using these pharmaceutical compositions; or interfering with telomere replication or repair using these pharmaceutical compositions.

These and other aspects of the invention are described in more detail herein.

BRIEF DESCRIPTION OF THE DRAWINGS

FIG. 1A: A homology model for human DNA2 in complex with single-stranded DNA (ssDNA). Three potential drug binding pockets are specified as Sites 1-3. FIG. 1B: Refinement of the DNA2 model structure by molecular dynamics simulation (50 ns). Root mean square deviation (RMSD) values during simulation at three potential drug binding sites are shown as fluctuating bars. The secondary structures of the sites are represented by color, which is specified at the bottom of the graph. FIG. 1C: The linear domain and motif structures and the drug binding sites of human DNA2. Upper panel: the DNA2 functional domain structure; Middle panel: the three putative drug binding sites; and Bottom panel: the secondary structure motifs. FIG. 1D: Inhibition of DNA2 nuclease activity by chemical compounds that were selected from the virtual screen. Recombinant flag-tagged DNA2 (10 nM) was mixed with $^{32}$P-labeled flap DNA substrates (500 fmol) in the absence or presence of the potential DNA2 binding chemical compound (250 µM each). The image shows a representative biochemical reaction (37° C., 15 min) that was resolved using 15% denaturing polyacrylamide gel electrophoresis (PAGE). The locations of substrates and products on the gel are indicated. FIG. 1E: The chemical name and structure of C5.

FIGS. 2A-2G. Inhibitory kinetics of DNA2 nuclease activity, and C5 inhibitory effects to ATPase activity and DNA substrate binding capacity (see also FIGS. 9A-9B). The nuclease activity of DNA2 was analyzed in the presence of varying concentrations of DNA2 enzyme (0.5-5 nM), flap DNA substrate (5-50 nM), and DNA2 inhibitors C5 (0-250 µM). FIG. 2A: Lineweaver-Burk plot of DNA2 nuclease activity in the presence of various concentrations of flap DNA substrate (x axis) and C5 (04, designated as [I]). FIG. 2B: DNA2 nuclease activity in the presence of various concentrations of compound C5 (x axis) and flap DNA substrate (nM, designated as [S]). The C5 concentration ($IC50_{observed}$) that inhibits 50% of the DNA2 nuclease activity at a given concentration of DNA substrates is indicated with dotted lines. The inhibited nuclease activities were normalized to the DMSO control, set as 1. FIG. 2C: Plot of $IC50_{observed}$ versus [S] for determination of IC50. The values of $IC50_{observed}$ obtained from panel B and corresponding DNA substrate concentrations were plotted. When [S] is zero, the derived corresponding $IC50_{observed}$ value is the theoretical IC50 of C5. In FIGS. 2A-2C, the values are means±s.d of three independent experiments. FIG. 2D: The representative TLC image showing C5 inhibition of the ATPase activity of DNA2. The DNA2 enzyme concentration used was 10 nM; ATP substrate concentration used was 200 µM; DNA concentration used was 200 nM; The inhibitor C5 concentrations used was in a range of 0 to 250 µM. FIG. 2E: Quantification of inhibition of DNA2 in the ATPase activity, the relative ATPase activities normalized to DMSO control. The values shown are the means±s.d. of three independent assays. FIG. 2F: The representative EMSA image showing C5 inhibition of DNA2 binding to the DNA substrate. The DNA2 enzyme concentration used was 50 nM; the $^{32}P$ labeled DNA concentration used was 1 nM; the compound C5 concentrations used ranged from 0 to 1,000 µM. FIG. 2G: Quantification of inhibition of DNA2 substrate binding, the relative binding activities normalized to DMSO control. The values shown are the means±s.d. of three independent assays.

FIGS. 3A-3C. DNA2 mutations at Site 1 impair C5 inhibition of DNA2 nuclease activity (see also FIGS. 10A-10C). FIG. 3A: Three dimensional structure of the Site 1 small molecule binding pocket of DNA2. The left panel shows a cartoon view and the right panel shows a surface view of Site 1. FIG. 3B: The 14 residues within 6 Å spheres around compound C5 that form Site 1 pocket were identified. Among them, F696A and L732A, which did not affect the nuclease activity of DNA2 (FIGS. 11A-11B), reduced C5 inhibition of DNA2 nuclease activity. The nuclease activity of WT, F696A, and L732A (1 nM) was assayed in the presence of various concentrations of C5 (indicated as [I] in a range from 0 to 250 µM) and quantified, the DNA substrate concentration was 15 nM. We added DMSO without the inhibitor C5 as a control where the relative nuclease activity was set as 1. The values shown are the means±s.d. of three independent experiments. FIG. 3C: The DNA binding activity of F696A and L732A is resistant to C5 inhibitor. We added DMSO without the inhibitor C5 as a control where the relative binding activity was set as 1. The DNA2 enzyme concentration used was 50 nM. The DNA concentration used was 1 nM. The inhibitor C5 concentrations ranged from 0 to 125 µM. The values shown are the means±s.d. of three independent experiments.

FIGS. 4A-4C. IC50 and on-target cytotoxic effects of C5 in human cancer cells and mouse embryonic stem (MES) cells. FIG. 4A: IC50 values of C5 with a panel of 18 cell lines from 4 major types of cancers. Human non-cancerous or cancer cells were seeded on a 96-well plate and incubated in culture medium containing 0 to 80 µM C5 for 7 days. The IC50 was calculated using the CompuSyn software (Chou, 2010). Values are the average of two independent assays. FIG. 4B: Control (shSCR) or DNA2 knockdown MCF7cells were cultured in medium containing 0 or 1 µM C5 for 4 days. The live cells were counted. The cell survival was calculated by normalizing the number of live cells from each culture to that of the control MCF7 cells (shSCR), which was arbitrarily set as 100. FIG. 4C: The same experiment as in A was performed on MES cells from WT and DNA2 knockout mice, which were cultured in medium containing 0 or 1 µM C5 for 4 days. The values shown are the means±s.d. of three experiments.

FIG. 5A: C5 inhibits HDR and SSA frequency. The U2OS cells carrying the GFP reporter gene for HDR or single-strand annealing (SSA) assay were transfected with I-Sce I expression vector. The cells were then incubated in medium containing 0, 10, 20, 40, 60 µM C5. After 72 h, the cells were harvested and the GFP positive cells were analyzed by flow cytometry. In the DNA2 knockdown experiment, the U2OS cells were transfected with 10 nM of scrambled or DNA2 siRNA oligos for 24 hours. The cells were then transfected with the I-SceI expression vector. After 48 h, the cells were harvested and the GFP positive cells were analyzed by flow cytometry. Knockdown of DNA2 in the engineered U2OS cells was confirmed by western blot (FIG. 11A-11B). Values are mean±s.d. of three independent experiments. FIG. 5B: DNA2 inhibition by siRNA or C5 impairs replication fork-related DNA end resection in MCF7 cells at similar levels. MCF7 cells were untreated or treated with 10 µM C5 for 24 hours (left panels) or treated with scrambled siRNA (siControl) or siRNA against DNA2 (siDNA2) for 72 hours (right panels). The knockdown efficiency of DNA2 was checked by western blotting. The cells were then treated with 1 µM CPT for 4 hours. The levels of γ-H2AX and phosphorylated RPA (S33) were analyzed by western blot using antibodies against γH2AX (Millipore) and phosphorylated RPA (S33) (Abcam). Total level of RPA and β-actin were used as controls, which were detected using antibodies against RPA32 (Abcam) and β-actin (GeneTex). FIGS. 5C-5H: DNA2 inhibition by siRNA or C5 impairs replication fork-related DNA end resection in A549 cells at similar levels. A549 cells were untreated or treated with 10 µM C5 for 24 hours (FIGS. 5C-5E) or treated with scrambled siRNA (siControl) or siRNA against DNA2 (siDNA2) for 48 hours (FIGS. 5F-5H). The knockdown efficiency of DNA2 was checked by western blotting (FIGS. 11A-11B). The cells were then treated with 1 µM CPT for 4 hours. FIGS. 5C and 5F: Representative images. FIGS. 5D, 5E, 5G, and 5H: Quantifications: the levels of γ-H2AX and phosphorylated RPA (S33) were quantified by ImagePro Premier, and the relative P-RPA or γH2AX per nucleus was calculated. Values are means±s.d. of three independent assays.

FIGS. 6A and 6B: C5 inhibits DNA replication fork restart at similar levels as DNA2 knockdown. FIG. 6A: A549 cells were mock or pretreated with C5 (20 µM) for 2 hours, labeled with IdU (red) for 30 min, and co-cultured with IdU and the indicated drugs (20 µM C5, 150 nM CPT or 2 mM HU) or drug combinations (20 µM C5 combined with 150 nM CPT or 2 mM HU) for 1 hour, and then washed and labeled with CIdU (green) for 40 min. Percentage of restarting forks (red-green tracks) was calculated by dividing the red-green tracks by the sum of the red-green and red only tracks. At least 150 tracks counted for each sample as shown in left panels were calculated. Values are means±s.d. from three independent experiments (Right panel). The p value was calculated by the student's t-test. FIG. 6B: For the control experiment in which knockdown of DNA2 was employed, A549 cells were transfected with scrambled or DNA2 siRNAs for 72 hours, and the ability of the cells to restart replication after CPT or HU fork stalling was determined as in panel A. Western blotting confirmed an efficient knockdown of DNA2 at 72h post siRNA transfections (FIG. 11A-11B). In both panels A and B, red tracks represent synthesis before addition of HU or CPT. Red/green tracks represent molecules that recovered from fork stalling. Green only tracks represent initiations after removal of HU or CPT. FIGS. 6C-6D. C5 prevents single-stranded DNA accumulation in BOD1L-depleted or BRCA2-depleted U2OS cells upon replication stalling with HU at similar level as DNA2 knockdown. FIG. 6C: Cells with more than 15 P-RPA foci indicative of single-stranded DNA were scored in U2OS cells transfected with siRNA against BRCA2 or BOD1L or scrambled siRNA, as indicated, followed by treatment with 4 mM hydroxyurea (HU) for 5 h. Cells were pretreated with MRE11 inhibitor mirin (50 μM) or DNA2 inhibitor C5 (20 μM). In the absence of HU, no cells with greater than 15 foci were observed. FIG. 6D: Cells with more than 15 P-RPA foci indicative of single-stranded DNA were scored in U2OS cells transfected with siRNA against BRCA2 or scrambled siRNA, as indicated, followed by treatment with 4 mM HU for 5 h. Cells were pretreated with MRE11 inhibitor, PFM39 or siRNA against DNA2. In both FIGS. 6C and 6D, top panels show the representative immunofluorescence images, and the bottom panel shows the quantifications. Error bars represent the SEM. p-values were calculated with the student T-test. Western blots of knockdowns are shown in FIGS. 12A-12B.

FIG. 7A: C5 sensitizes MCF cells to CPT. Clonogenic assays were conducted to evaluate the survival rate of MCF cells treated with different concentrations of CPT in the absence or presence of C5 (1 μM). The survival rate of the cells treated with various concentrations of CPT was calculated by normalizing the number of colonies to that of the cells without CPT treatment. The survival rate of the cells without CPT treatment was arbitrarily set as 1. The values shown are the means±s.d. of three independent experiments. FIGS. 7B-7C: The synergy between the DNA2 inhibitor C5 and the PARP inhibitor MK4827 was assayed by clonogenic assay. The values are means±s.d. of three independent clonogenic assays. The IC50 and combination index (CI) was calculated using the Compusyn program. FIG. 7B: Representative inhibition curve of varying concentrations of C5 from 0 to 10 μM in combination with MK4827 (0 or 1 μM). FIG. 7C: Representative inhibition curve of varying concentrations of MK4827 from 0 to 1 μM in combination with C5 (0 or 2 μM).

FIG. 8A and FIG. 8B shows elimination of DNA2 gene sensitizes mouse ES (MES) cells to radiation and camptothecin (CPT) FIG. 8A: The survival curves of WT and dna2$^{-/-}$ MES cells after ionizing radiation (IR) treatment. WT and dna2$^{-/-}$ MES cells were exposed to 1, 2, 4, 6 gray (Gy) γ-irradiation. The surviving MES cell colonies were counted and normalized to the corresponding untreated control, whose survival rate was arbitrarily set as 1. FIG. 8B: The survival curve of the WT and dna2$^{-/-}$ MES cells after CPT treatment. The WT and dna2$^{-/-}$ MES cells were cultured in the medium containing 6.25, 12.5, 25, and 100 nM CPT. The surviving ES cell colonies were counted and normalized to corresponding untreated control, whose survival rate was arbitrarily set as 1. In both panels, each point represents the means±s.d of three independent assays.

FIGS. 8C-8F show DNA2, FEN1 and EXO1 nuclease assays used to test the inhibitor specificity. FIGS. 8C-E show DNA2, FEN1, and EXO1 nuclease assays with the inhibitor titration, respectively. FIG. 8F shows quantification of DNA2 FEN1 and EXO1 activities. The enzyme concentrations used for DNA2, FEN1 and EXO1 are all 10 nM. The DNA substrate concentration used was 50 nM. A range of the inhibitor C5 concentrations used was from 0 to 125 μM. The relative activities normalize to DMSO, which activity set as 1. Each experiment was repeated at least three times. The error bar represents the standard deviations. Symbols used: (diamond) FEN1, (square) EXO1, (triangle) DNA2.

FIG. 9A. Time course of flap substrate cleavage catalyzed by DNA2 enzyme. Various DNA2 concentrations and various substrate concentrations were used to determine the proper time for assays. 12 time points were tested. The efficiency is the best during 1-10 minutes. FIG. 9B: Inhibition of DNA2 helicase activity by C5. hDNA2 D277A, nuclease-deficient, was purified as described previously. The helicase substrate is a 43 base oligonucleotide annealed to M13DNA over 24 bases and having an 18 nt 5' noncomplementary tail. The oligonucleotide was 5' labeled with [g-32P] ATP by T4 polynucleotide kinase and purified with a Sepharose CL4B column. The standard reaction mixture contained 50 mM Tris-HCl, pH7.5, 2 mM DTT, 0.25 mg/ml BSA, 4 mM MgCl$_2$, 4 mM ATP and 32P-labeled helicase substrate. C5 was preincubated with enzyme for 1 min. The reaction was for 30 min at 37° C. The reaction was stopped with 5× stop solution (60 mM EDTA, 40% sucrose, 0.6% SDS, 0.25% bromphenol blue and 0.25% zylene cyanole FF). Reaction products were separated on an 8% native polyacrylamide gel containing 0.1% SDS and detected by phosphorimaging and quantified using ImageQuant. Lane 1, boiled substrate; Lane 2, no enzyme, Lanes 3-6 contained 5, 10 and 15 nM DNA2, respectively; lanes 7-10 contained 5, 10, and 15 nM DNA2 plus 100 mM C5. Lanes 3, 4 and 5 represent the amount of helicase at each of the three increasing helicase concentrations in the absence of C5. Lanes 6, 7, and 8 represent the same amount of enzyme as 3, 4, 5, respectively, but in the presence of C5. The percent of helicase remaining after C5 treatment is presented as the amount of substrate unwound in lane 6 divided by the amount in lane 3, the amount of substrate unwound in lane 7 divided by the amount in lane 4, and the amount of substrate unwound in lane 8 divided by the amount in lane 5.

FIG. 10A: Nuclease assay to determine the activities of the WT and mutants. The enzyme concentrations used for DNA2 and its mutants are all 10 nM. The DNA substrate concentration used was 50 nM. FIG. 10B: Quantification of the WT and mutants nuclease activities. The WT activity was set as 1. FIG. 10C: Nuclease activity assays to measure the sensitivity of the WT (lane 1-9) and mutants F696A (lanes 10-18) and L732A (lanes 19-27) to the inhibitor C5. The enzyme concentrations used for DNA2 and its mutants are all 10 nM. The DNA substrate concentration used was 50 nM. The inhibitor concentrations used were in a range from 0 to 1000 μM.

FIG. 11A: Cell cycle analysis by flow cytometry. HCT116 cells were treated with 0, 10, 50 μM C5 for 48 h. The cells were stained by PI and the cell cycle profile was determined by flow cytometry and calculated by the Flow Jo software based on DNA contents. FIG. 11B: Knockdown of DNA2 in MCF7, A549, and U2OS cells. Cells at 50-60% confluence were transfected with scramble siRNA oligos (siControl) or siRNA oligos against human DNA2 (Sigma). After 48 hours incubation, cells were harvested and lysed. The level of DNA2 were detected by western blot using an antibody against human DNA2. The level of β-actin was used as a loading control. Antibodies were from Abgent.

FIG. 12A: DNA fiber assay confirms that C5 inhibits DNA replication fork restart in the presence of high concentration of CPT. A549 cells were first labeled with IdU (red) and co-cultured with the indicated drugs (10 μM C5 or 2 μM CPT) or drug combinations (10 μM C5 and 2 μM CPT), and then washed and labeled with CldU (green). The different types of typical tracks. Left panels: representative images of different tracks; right panel: Quantification of the different tracks found in the cells with different treatments. Approximate 150 tracks were scored in each assay. Values are means±s.d. from three independent experiments. The p value was calculated with the student's t-test. FIG. 12B: Knockdown of DNA2, BRCA2, and BOD1L in U2OS cells. The cells at 50-60% confluence were transfected with scramble siRNA oligos or siRNA oligos (Sigma) against human BOD1L, BRCA2 and DNA2 individually or in combination. The levels of BOD1L, BRCA2, or DNA2 were detected by western blot using an antibody against human BOD1L, BRCA2, or DNA2. The level of β-actin was used as a loading control. Antibodies were from Abgent.

As shown in FIG. 15, at 125 nM cisplatin, cells treated with 10 μM C5 showed an increase in survival compared to cells not treated with C5.

DETAILED DESCRIPTION

I. Definitions

Figure 1A:
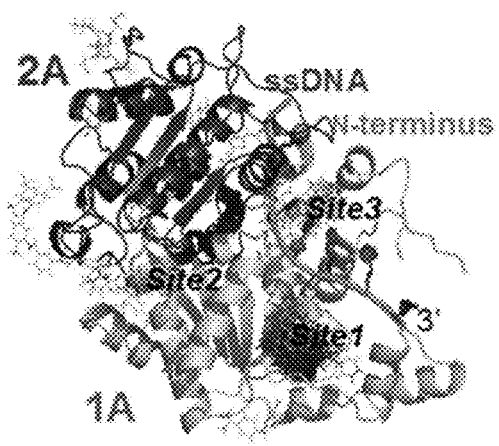
FIGS. 1A-1E. Three dimensional human DNA2 model and potential pockets for screening small molecule DNA2 inhibitors (See also FIGS. 8A-8F and Table 1).

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched non-cyclic chain, or combinations thereof, including at least one carbon atom and at least one heteroatom (e.g. O, N, P, Si, and S), and wherein the nitrogen and sulfur atoms may optionally be oxidized, and the nitrogen heteroatom may optionally be quaternized. The heteroatom(s) (e.g. O, N, P, S, and Si) may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl", "heteroalkyl", "cycloalkyl", "heterocycloalkyl", "aryl", and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S($O)_2$R', —S(O)$_2$NR'R", —NRSO$_2$R', —NR'NR"R'", —ONR'R", —NR'C=(O)NR"NR'"R"", —CN, —$NO_2$, in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR' R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —$NO_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC═(O) NH$_2$, —NHSO$_2$H, —NHC═(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:

(i) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC═(O) NH$_2$, —NHSO$_2$H, —NHC═(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:

(a) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC═(O) NH$_2$, —NHSO$_2$H, —NHC═(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC═(O) NH$_2$, —NHSO$_2$H, —NHC═(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents than are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Provided herein are agents (e.g. compounds, drugs, therapeutic agents) that may be in a prodrug form. Prodrugs of the compounds described herein are those compounds that readily undergo chemical changes under select physiological conditions to provide the final agents (e.g. compounds, drugs, therapeutic agents). Additionally, prodrugs can be converted to agents (e.g. compounds, drugs, therapeutic agents) by chemical or biochemical methods in an ex vivo environment. Prodrugs described herein include compounds that readily undergo chemical changes under select physiological conditions to provide agents (e.g. compounds, drugs, therapeutic agents) to a biological system (e.g. in a subject).

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers. In embodiments, the compounds described herein are tautomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$), or carbon-14 ($^{14}C$). All isotopic variations of the compounds of the present invention, whether radioactive or not, are encompassed within the scope of the present invention.

The symbol "⌇" denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods herein treat hyperproliferative disorders, such as cancer (e.g. ovarian cancer, bladder cancer, head and neck cancer, brain cancer, breast cancer, lung cancer, cervical cancer, bone cancer, spinal cancer, liver cancer, colorectal cancer, pancreatic cancer, glioblastoma, neuroblastoma, rhabdomyosarcoma, osteosarcoma, renal cancer, renal cell carcinoma, non-small cell lung cancer, uterine cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, nasopharyngeal cancer, head and neck squamous cell carcinoma, or prostate cancer). For example certain methods herein treat cancer by decreasing or reducing or preventing the occurrence, growth, metastasis, or progression of cancer or by decreasing or reducing or preventing a symptom of cancer. Symptoms of cancer (e.g., ovarian cancer, bladder cancer, head and neck cancer, brain cancer, breast cancer, lung cancer, cervical cancer, bone cancer, spinal cancer, liver cancer, colorectal cancer, pancreatic cancer, glioblastoma, neuroblastoma, rhabdomyosarcoma, osteosarcoma, renal cancer, renal cell carcinoma, non-small cell lung cancer, uterine cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, nasopharyngeal cancer, head and neck squamous cell carcinoma, or prostate cancer) would be known or may be determined by a person of ordinary skill in the art. The term "treating" and conjugations thereof, include prevention of an injury, pathology, condition, or disease (e.g. preventing the development of one or more symptoms of cancer (e.g. ovarian cancer, bladder cancer, head and neck cancer, brain cancer, breast cancer, lung cancer, cervical cancer, bone cancer, spinal cancer, liver cancer, colorectal cancer, pancreatic cancer, glioblastoma, neuroblastoma, rhabdomyosarcoma, osteosarcoma, renal cancer, renal cell carcinoma, non-small cell lung cancer, uterine cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, nasopharyngeal cancer, head and neck squamous cell carcinoma, or prostate cancer).

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatinifomi carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

An "effective amount" is an amount sufficient to accomplish a stated purpose (e.g. achieve the effect for which it is administered, treat a disease, reduce enzyme activity, increase enzyme activity, reduce protein function, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing the severity or frequency of the symptom(s), or elimination of the symptom(s). A "prophylactically effective amount" of a drug or prodrug is an amount of a drug or prodrug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The term "associated" or "associated with" in the context of a substance or substance activity or function associated with a disease (such as cancer) means that the disease is caused by (in whole or in part), or a symptom of the disease is caused by (in whole or in part) the substance or substance activity or function. As used herein, what is described as being associated with a disease, if a causative agent, could be a target for treatment of the disease. For example cancer may be treated with a composition (e.g. compound, composition, nanoparticle, or conjugate, all as described herein) effective for inhibiting DNA replication.

"Control" or "control experiment" or "standard control" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein. In some embodiments contacting includes allowing a compound described herein to interact with a stromal cell. In some embodiments contacting includes allowing a compound described herein to interact with an immune cell. In some embodiments contacting includes allowing a compound described herein to interact with a protein associate with a stromal cell. In some embodiments contacting includes allowing a compound described herein to interact with a protein associated with an immune cell. In some embodiments contacting includes allowing a compound described herein to interact with the extracellular matrix generated by a stromal cell. In some embodiments contacting includes allowing a compound described herein to interact with the extracellular matrix generated by an immune cell.

As defined herein, the term "inhibition", "inhibit", "inhibiting" and the like in reference to a protein-inhibitor (e.g. antagonist) interaction means negatively affecting (e.g. decreasing) the level of activity or function of the protein relative to the level of activity or function of the protein in the absence of the inhibitor. In embodiments, inhibition refers to a decrease in DNA replication or transcription. In some embodiments inhibition refers to reduction of a disease or symptoms of disease, such as cancer. Thus, inhibition may include, at least in part, partially or totally blocking stimulation, decreasing, preventing, or delaying activation, or inactivating, desensitizing, or down-regulating signal transduction or enzymatic activity or the amount of a protein.

As defined herein, the term "activation", "activate", "activating" and the like in reference to a protein-activator (e.g. agonist) interaction means positively affecting (e.g. increasing) the activity or function of the protein relative to the activity or function of the protein in the absence of the activator (e.g. compound described herein). Thus, activation may include, at least in part, partially or totally increasing stimulation, increasing or enabling activation, or activating, sensitizing, or up-regulating signal transduction or enzymatic activity or the amount of a protein decreased in a disease. Activation may include, at least in part, partially or totally increasing stimulation, increasing or enabling activation, or activating, sensitizing, or up-regulating signal transduction or enzymatic activity or the amount of a protein.

The term "modulator" refers to a composition that increases or decreases the level of a target molecule or the function of a target molecule.

As used herein, the term "cancer" refers to all types of cancer, neoplasm or malignant tumors found in mammals, including leukemia, lymphoma, carcinomas and sarcomas. Exemplary cancers that may be treated with a compound, pharmaceutical composition, or method provided herein include ovarian cancer, lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma, cisplatin resistant lung cancer, carboplatin resistant lung cancer, platinum-based compound resistant lung cancer), glioblastoma multiforme, glioma, or melanoma. Additional examples include, cancer of the thyroid, endocrine system, brain, breast, cervix, colon, head & neck, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer. In embodiments "cancer" refers to a cancer resistant to an anti-cancer therapy (e.g. treatment with an anti-cancer agent). In embodiments, the cancer is breast cancer. In embodiments, the cancer is colon cancer. In embodiments, the cancer is prostate cancer. In embodiments, the cancer is lung cancer. In embodiments, the cancer is ovarian cancer.

"Radiation" and "radiation therapy" refers to any in the art, and includes external beam radiation therapy, internal radiation therapy, and systemic radiation therapy. Systemic radiation therapy refers to administering a patient a radiopharmaceutical (e.g., radioactive substances such as iodine, strontium, samarium, radium; and radioactive substances bound to monoclonal antibodies).

"Patient" or "subject in need thereof" or "subject" refers to a living organism suffering from or prone to a disease or condition that can be treated by administration of a compound or pharmaceutical composition or by a method, as provided herein. Non-limiting examples include humans, other mammals, bovines, rats, mice, dogs, monkeys, goat, sheep, cows, deer, and other non-mammalian animals. In some embodiments, a patient is human. In some embodiments, a subject is human.

"Disease" or "condition" refer to a state of being or health status of a patient or subject capable of being treated with a compound, pharmaceutical composition, or method provided herein. In embodiments, the disease is cancer.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional compositions (e.g., chemotherapeutic agents, radiopharmaceuticals) or therapies (e.g., radiation). The compound of the invention can be administered alone or can be coadministered with a chemotherapeutic agent and/or a radiopharmaceutical. Coadministration is meant to include simultaneous or sequential administration of the compound individually or in combination with one or more chemotherapeutic agents and/or one or more radiopharmaceuticals. Thus, the preparations can also be combined, when desired, with other active substances (e.g. to reduce metabolic degradation, to increase degradation of a prodrug and release of the drug, detectable agent). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J Microencapsul.* 13:293-306, 1996; Chonn, *Curr. Opin. Biotechnol.* 6:698-708, 1995; Ostro, *Am. J Hosp. Pharm.* 46:1576-1587, 1989). The compositions of the present invention can also be delivered as nanoparticles.

Pharmaceutical compositions provided by the present invention include compositions wherein the active ingredient (e.g. compounds described herein, including embodiments or examples) may be contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., reducing, eliminating, or slowing the progression of disease symptoms. Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents (e.g. anti-cancer agents) known to be useful in treating a disease described herein (e.g. cancer), or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent (e.g. anti-cancer agent). Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds or platinum containing agents (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflomithine; elemene; emitefur; epirubicin, epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras famesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodeaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflomithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-azaepothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), Vincristine sulfate, Cryptophycin 52 (i.e. LY-355703), Vitilevuamide, Tubulysin A, Canadensol, Centaureidin (i.e. NSC-106969), Oncocidin Al (i.e. BTO-956 and DIME), Fijianolide B, Laulimalide, Narcosine (also known as NSC-5366), Nascapine, Hemiasterlin, Vanadocene acetylacetonate, Monsatrol, lnanocine (i.e. NSC-698666), Eleutherobins (such as Desmethyleleutherobin, Desaetyleleutherobin, lsoeleutherobin A, and Z-Eleutherobin), Caribaeoside, Caribaeolin, Halichondrin B, Diazonamide A, Taccalonolide A, Diozostatin, (-)-Phenylahistin (i.e. NSCL-96F037), Myoseverin B, Resverastatin phosphate sodium, steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, hormonal therapies, or the like.

"Analog" and "analogue" are used interchangeably and are used in accordance with their plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound, including isomers thereof. Accordingly, an analog is a compound that is similar or comparable in function and appearance but not in structure or origin to a reference compound.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/-10% of the specified value. In embodiments, about means the specified value.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature. Sulfur-containing amino acids refers to naturally occurring and synthetic amino acids comprising sulfur, e.g., methionine, cysteine, homocysteine, and taurine.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

Fanconi anemia is a disease characterized by developmental abnormalities, bone marrow failure and cancer predisposition. In embodiments, Fanconi anemia is referred to as Fanconi hypoplastic anemia, Fanconi pancytopenia, or Fanconi panmyelopathy.

The term "sensitize" or "sensitizing" as used herein in reference to cancer cells susceptibility to cancer therapies (e.g., chemotherapeutic agent, radiation, or a combination thereof) means positively affecting (e.g., increasing) the susceptibility of the cancer cells (e.g., improving the efficacy of the cancer therapies) relative to the susceptibility of the cancer cells in the absence of the compound as described herein. In embodiments, sensitizing permits lower doses of cancer therapies (e.g., chemotherapeutic agent, radiation, or a combination thereof) relative to the absence of sensitizing to be therapeutically effective.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Where a moiety is substituted (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene), the moiety is substituted with at least one substituent (e.g., a substituent group, a size-limited substituent group, or lower substituent group) and each substituent is optionally different. Additionally, where multiple substituents are present on a moiety, each substituent may be optionally differently.

II. Compositions

Provided herein are compounds that are, inter alia, useful for the treatment of cancer or Fanconi anemia.

In an aspect is provided a compound or pharmaceutically acceptable salt thereof, having the formula:

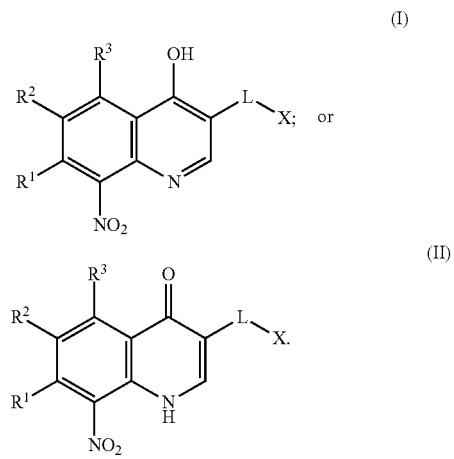

$R^1$, $R^2$, and $R^3$ are each independently hydrogen, halogen, —$N_3$, —NHC=(O)NHNH$_2$, —CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)$_n$R$^{13}$, —S(O)$_n$NR$^9$R$^{10}$, —NR$^{12}$S(O)$_n$R$^{13}$, —NO$_2$, —OR$^{14}$, —SR$^{14}$, —NR$^{15}$, —OCOR$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. L is a bond, —C(O)—NH—, —NH—C(O)—, —C(O)—, —C(O)—O, —NH—, —O—, —S—, —S(O)—, —S(O)$_2$—, —NH—S(O)—, —NH—S(O)$_2$—, —CH$_2$N(C(O)OH)—, —CH$_2$—N(CH(O))—, —CH$_2$—N(SO$_2$)—, —CH$_2$NH—, —CH$_2$C(O)NH—, —CH$_2$NHC(O)—, —CH$_2$NHS(O)—, —CH$_2$NHS(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. X is hydrogen, halogen, —N$_3$, —NHC=(O)NHNH$_2$, —CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)$_n$R$^{13}$, —S(O)$_n$NR$^9$R$^{10}$, —NR$^{12}$S(O)$_n$R$^{13}$, —NO$_2$, —OR$^{14}$, —SR$^{14}$, —NR$^{15}$, —OCOR$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^9$, R$^{10}$ R$^{11}$, R$^{12}$, R$^{13}$, R$^{14}$, R$^{15}$, and R$^{16}$, are independently hydrogen, halogen, —CN, —CF$_3$, —CCl$_3$, —CBr$_3$, —CI$_3$, —OH, —NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol n is an integer from 1 to 4.

In embodiments, the disclosure provides compounds of formula (I) or a pharmaceutically acceptable salt thereof, wherein the substituents are as defined herein.

In embodiments, the disclosure provides compounds of formula (II) or a pharmaceutically acceptable salt thereof, wherein the substituents are as defined herein.

In embodiments, L is a bond, —C(O)—NH—, —NH—C(O)—, —NH—, —O—, —S—, —S(O)—, —S(O)$_2$—, —NH—S(O)—, —NH—S(O)$_2$—, —CH$_2$N(C(O)OH)—, —CH$_2$—N(CH(O))—, —CH$_2$—N(SO$_2$)—, —CH$_2$NH—, —CH$_2$C(O)NH—, —CH$_2$NHC(O)—, —CH$_2$NHS(O)—, —CH$_2$NHS(O)$_2$—, substituted (e.g., substituted with substituent group(s), size-limited substituent group(s), or lower substituent group(s)) or unsubstituted alkylene, substituted (e.g., substituted with substituent group(s), size-limited substituent group(s), or lower substituent group(s)) or unsubstituted heteroalkylene, substituted (e.g., substituted with substituent group(s), size-limited substituent group(s), or lower substituent group(s)) or unsubstituted cycloalkylene, substituted (e.g., substituted with substituent group(s), size-limited substituent group(s), or lower substituent group(s)) or unsubstituted heterocycloalkylene, substituted (e.g., substituted with substituent group(s), size-limited substituent group(s), or lower substituent group(s)) or unsubstituted arylene, or substituted (e.g., substituted with substituent group(s), size-limited substituent group(s), or lower substituent group(s)) or unsubstituted heteroarylene.

In embodiments, L is —C(O)—NH—, —NH—C(O)—, —C(O)—, —C(O)—O, —NH—, —O—, —S—, —S(O)—, —S(O)$_2$—, —NH—S(O)—, —NH—S(O)$_2$—, —CH$_2$N(C(O)OH)—, —CH$_2$—N(CH(O))—, —CH$_2$—N(SO$_2$)—, —CH$_2$NH—, —CH$_2$C(O)NH—, —CH$_2$NHC(O)—, —CH$_2$NHS(O)—, —CH$_2$NHS(O)$_2$—, unsubstituted C$_1$-C$_6$ alkylene, unsubstituted C$_1$-C$_6$ heteroalkylene, unsubstituted 5-6 membered cycloalkylene, 5 to 6 membered unsubstituted heterocycloalkylene, 5-6 membered unsubstituted arylene, or 5 to 6 membered or unsubstituted heteroarylene. In embodiments, L is —C(O)—NH—, —NH—C(O)—, —NH—, —O—, —S—, —S(O)—, —S(O)$_2$—, —NH—S(O)—, —NH—S(O)$_2$—, —CH$_2$N(C(O)OH)—, —CH$_2$—N(CH(O))—, —CH$_2$—N(SO$_2$)—, —CH$_2$NH—, —CH$_2$C(O)NH—, —CH$_2$NHC(O)—, —CH$_2$NHS(O)—, —CH$_2$NHS(O)$_2$—, unsubstituted C$_1$-C$_6$ alkylene, unsubstituted C$_1$-C$_6$ heteroalkylene, unsubstituted 5-6 membered cycloalkylene, 5 to 6 membered unsubstituted heterocycloalkylene, 5-6 membered unsubstituted arylene, or 5 to 6 membered or unsubstituted heteroarylene.

In embodiments, L is —C(O)—NH—, —C(O)—, —C(O)—O—, —NH—, —O—, —S—, —S(O)—, or —S(O)$_2$—. In embodiments, L is —C(O)—NH—, —NH—, —O—, —S—, —S(O)—, or —S(O)$_2$—. In embodiments, L is —C(O)—NH— or —C(O)—O—. In embodiments, L is —C(O)—NH—.

In embodiments, R$^1$, is hydrogen, halogen, —N$_3$, —NHC=(O)NHNH$_2$, —CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)$_n$R$^{13}$, —S(O)$_n$NR$^9$R$^{10}$, —NR$^{12}$S(O)R$^{13}$, —NO$_2$, —OR$^{14}$, —SR$^{14}$, —NR$^{15}$, —OCOR$^{16}$, R$^{17}$-substituted or unsubstituted alkyl (e.g. C$_1$-C$_8$ alkyl, C$_1$-C$_6$ alkyl, or C$_1$-C$_4$ alkyl), R$^{17}$-substituted or unsubstituted heteroalkyl (e.g. 2 to 8 membered heteroalkyl, 2 to 6 membered heteroalkyl, or 2 to 4 membered heteroalkyl), R$^{17}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{17}$-substituted or unsubstituted heterocycloalkyl (e.g. 3 to 8 membered heterocycloalkyl, 4 to 8 membered heterocycloalkyl, or 5 to 6 membered heterocycloalkyl), R$^{17}$-substituted or unsubstituted aryl (e.g. C$_6$-C$_{10}$ aryl or C$_6$ aryl), or R$^{17}$-substituted or unsubstituted heteroaryl (e.g. 5 to 10 membered heteroaryl, 5 to 9 membered heteroaryl, or 5 to 6 membered heteroaryl). In embodiments, R$^1$ is hydrogen.

R$^{17}$ is oxo, halogen, —F, —Cl, —Br, —I, —CF$_3$, —CCl$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl (e.g. C$_1$-C$_8$ alkyl, C$_1$-C$_6$ alkyl, or C$_1$-C$_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. C$_3$-C$_8$ cycloalkyl, C$_4$-C$_8$ cycloalkyl, or C$_5$-C$_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. C$_6$-C$_{10}$ aryl or C$_6$ aryl), or unsubstituted heteroaryl (e.g. 5 to 10 membered heteroaryl, 5 to 9 membered heteroaryl, or 5 to 6 membered heteroaryl).

In embodiments, R$^2$ is hydrogen, halogen, —N$_3$, —NHC=(O)NHNH$_2$, —CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)$_n$R$^{13}$, —S(O)$_n$NR$^9$R$^{10}$, —NR$^{12}$S(O)$_n$R$^{13}$, —NO$_2$, —OR$^{14}$, —SR$^{14}$, —NR$^{15}$, —OCOR$^{16}$, R$^{18}$-substituted or unsubstituted alkyl (e.g. C$_1$-C$_8$ alkyl, C$_1$-C$_6$ alkyl, or C$_1$-C$_4$ alkyl), R$^{18}$-substituted or unsubstituted heteroalkyl (e.g. 2 to 8 membered heteroalkyl, 2 to 6 membered heteroalkyl, or 2 to 4 membered heteroalkyl), R$^{18}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{18}$-substituted or unsubstituted heterocycloalkyl (e.g. 3 to 8 membered heterocycloalkyl, 4 to 8 membered heterocycloalkyl, or 5 to 6 membered heterocycloalkyl), R$^{18}$-substituted or unsubstituted aryl (e.g. C$_6$-C$_{10}$ aryl or C6 aryl), or R$^{18}$-substituted or unsubstituted heteroaryl (e.g. 5 to 10 membered heteroaryl, 5 to 9 membered heteroaryl, or 5 to 6 membered heteroaryl). In embodiments, R$^2$ is hydrogen.

R$^{18}$ is oxo, halogen, —F, —Cl, —Br, —I, —CF$_3$, —CCl$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl (e.g. C$_1$-C$_8$ alkyl, C$_1$-C$_6$ alkyl, or C$_1$-C$_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. C$_3$-C$_8$ cycloalkyl, C$_4$-C$_8$ cycloalkyl, or C$_5$-C$_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

In embodiments, $R^3$, is hydrogen, halogen, —$N_3$, —NHC═(O)NHNH$_2$, —CN, —$CF_3$, —$CCl_3$, —$CBr_3$, —$CI_3$, —$NR^9R^{10}$, —$C(O)R^{11}$, —$C(O)NR^9R^{10}$, —$NR^{12}C(O)R^{11}$, —$S(O)_nR^{13}$, —$S(O)_nNR^9R^{10}$, —$NR^{12}S(O)_nR^{13}$, —$NO_2$, —$OR^{14}$, —$SR^{14}$, —$NR^{15}$, —$OCOR^{16}$, $R^{19}$-substituted or unsubstituted alkyl (e.g. $C_1$-$C_8$ alkyl, $C_1$-$C_6$ alkyl, or $C_1$-$C_4$ alkyl), $R^{19}$-substituted or unsubstituted heteroalkyl (e.g. 2 to 8 membered heteroalkyl, 2 to 6 membered heteroalkyl, or 2 to 4 membered heteroalkyl), $R^{19}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{19}$-substituted or unsubstituted heterocycloalkyl (e.g. 3 to 8 membered heterocycloalkyl, 4 to 8 membered heterocycloalkyl, or 5 to 6 membered heterocycloalkyl), $R^{19}$-substituted or unsubstituted aryl (e.g. $C_6$-$C_{10}$ aryl or $C_6$ aryl), or $R^{19}$-substituted or unsubstituted heteroaryl (e.g. 5 to 10 membered heteroaryl, 5 to 9 membered heteroaryl, or 5 to 6 membered heteroaryl). In embodiments, $R^3$ is hydrogen.

$R^{19}$ is OXO, halogen, —F, —Cl, —Br, —I, —$CF_3$, —$CCl_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)NHNH$_2$, —NHC═(O) NH$_2$, —NHSO$_2$H, —NHC═(O)H, —NHC(O)—OH, —NHOH, —$OCF_3$, —$OCHF_2$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. C3-C cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

In embodiments, $R^1$, $R^2$, and $R^3$ are independently hydrogen, halogen, —$NH_2$, —OH, —$NO_2$, —$C(O)CH_3$, —NHC(O)CH$_3$, —OC(O)CH$_3$, or unsubstituted $C_1$-$C_4$ alkyl. In embodiments, $R^1$, $R^2$, and $R^3$ are hydrogen. In embodiments, $R^1$, $R^2$, and $R^3$ are independently hydrogen, and L is —C(O)NH—.

In embodiments, X is hydrogen, halogen, —$N_3$, —NHC═(O)NHNH$_2$, —CN, —$CF_3$, —$CCl_3$, —$CBr_3$, —$CI_3$, —$NR^9R^{10}$, —$C(O)R^{11}$, —$C(O)NR^9R^{10}$, —$NR^{12}C(O)R^{11}$, —$S(O)_nR^{13}$, —$S(O)_nNR^9R^{10}$, —$NR^{12}S(O)_nR^{13}$, —$NO_2$, —$OR^{14}$, —$SR^{14}$, —$NR^{15}$, or —$OCOR^{16}$. In embodiments, X is substituted or unsubstituted alkylene (e.g. $C_1$-$C_8$ alkylene, $C_1$-$C_6$ alkylene, or $C_1$-$C_4$ alkylene), substituted or unsubstituted heteroalkylene (e.g. 2 to 10 membered heteroalkylene, 2 to 8 membered heteroalkylene, 4 to 8 membered heteroalkylene, 2 to 6 membered heteroalkylene, or 2 to 4 membered heteroalkylene), substituted or unsubstituted cycloalkylene (e.g. $C_3$-$C_8$ cycloalkylene, $C_4$-$C_8$ cycloalkylene, or $C_5$-$C_6$ cycloalkylene), substituted or unsubstituted heterocycloalkylene (e.g. 3 to 8 membered heterocycloalkylene, 4 to 8 membered heterocycloalkylene, or 5 to 6 membered heterocycloalkylene), substituted or unsubstituted arylene (e.g. $C_6$-$C_{10}$ arylene or $C_6$ arylene), or substituted or unsubstituted heteroarylene (e.g. 5 to 10 membered heteroarylene, 5 to 9 membered heteroarylene, or 5 to 6 membered heteroarylene).

In embodiments, X is substituted $C_1$-$C_8$ alkyl, substituted 2-8 membered heteroalkyl, substituted $C_3$-$C_8$ cycloalkyl, substituted 3-6 membered heterocycloalkyl, substituted phenyl, or substituted 5 or 6 membered heteroaryl. In embodiments, X is unsubstituted $C_1$-$C_8$ alkyl, unsubstituted 2-8 membered heteroalkyl, unsubstituted $C_3$-$C_8$ cycloalkyl, unsubstituted 3-6 membered heterocycloalkyl, unsubstituted phenyl, or unsubstituted 5 or 6 membered heteroaryl. In embodiments, X is a substituted or unsubstituted $C_1$-$C_8$ alkyl. In embodiments, X is a substituted or unsubstituted $C_1$-$C_6$ alkyl. In embodiments, X is a substituted or unsubstituted $C_1$-$C_4$ alkyl. In embodiments, X is a substituted or unsubstituted $C_4$ alkyl. In embodiments, X is an unsubstituted $C_1$-$C_8$ alkyl. In embodiments, X is an unsubstituted $C_1$-$C_6$ alkyl. In embodiments, X is an unsubstituted $C_1$-$C_4$ alkyl. In embodiments, X is an unsubstituted $C_4$ alkyl. In embodiments, X is —$CH_3$. In embodiments, X is a substituted $C_1$-$C_8$ alkyl. In embodiments, X is a substituted $C_1$-$C_6$ alkyl. In embodiments, X is a substituted $C_1$-$C_4$ alkyl. In embodiments, X is a substituted $C_4$ alkyl.

In embodiments, X is $R^{2a}$-substituted or unsubstituted $C_1$-$C_8$ alkyl, $R^{2a}$-substituted or unsubstituted 2 to 8 membered heteroalkyl, $R^{2a}$-substituted or unsubstituted $C_3$-$C_8$ cycloalkyl, $R^{2a}$-substituted or unsubstituted 3 to 6 membered heterocycloalkyl, $R^{2a}$-substituted or unsubstituted phenyl, or $R^{2a}$-substituted or unsubstituted 5 or 6 membered heteroaryl. In embodiments, X is a $R^{2a}$-substituted or unsubstituted $C_1$-$C_8$ alkyl. In embodiments, X is a $R^{2a}$ substituted or unsubstituted $C_1$-$C_6$ alkyl. In embodiments, X is a $R^{2a}$-substituted or unsubstituted $C_1$-$C_4$ alkyl. In embodiments, X is a $R^{2a}$-substituted or unsubstituted $C_4$ alkyl. In embodiments, X is a $R^{2a}$-substituted $C_1$-$C_8$ alkyl. In embodiments, X is a $R^{2a}$-substituted $C_1$-$C_6$ alkyl. In embodiments, X is a $R^{2a}$-substituted $C_1$-$C_4$ alkyl. In embodiments, X is a $R^{2a}$-substituted $C_4$ alkyl. In embodiments, X is a $R^{2a}$-substituted $C_1$ alkyl. In embodiments, X has the formula:

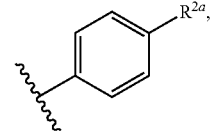

wherein $R^{2a}$ is as described herein. In embodiments, X has the formula:

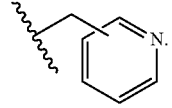

In embodiments, X has the formula:

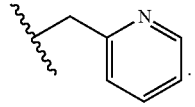

$R^{2a}$ is independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —NHC(O)NHNH$_2$, $R^{2b}$-substituted or unsubstituted $C_1$-$C_8$ alkyl, $R^{2b}$-substituted or unsubstituted 2-8 membered heteroalkyl, $R^{2b}$-substituted or unsubstituted $C_3$-$C_8$ cycloalkyl, $R^{2b}$-substituted or unsubstituted 3-6 membered heterocycloalkyl, $R^{2b}$-substituted or unsubstituted phenyl, or $R^{2b}$-substituted or unsubstituted 5 or 6 membered heteroaryl. In embodiments, $R^{2a}$ is independently halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_3$H, —SO$_4$H, —SO$_2$NH$_2$, —NHNH$_2$, —ONH$_2$, —NHC(O)NHNH$_2$, $R^{2b}$-substituted or unsubstituted C$_1$-C$_8$ alkyl, $R^{2b}$-substituted or unsubstituted 2-8 membered heteroalkyl, $R^{2b}$-substituted or unsubstituted C$_3$-C$_8$ cycloalkyl, $R^{2b}$-substituted or unsubstituted 3-6 membered heterocycloalkyl, $R^{2b}$-substituted or unsubstituted phenyl, or $R^{2b}$-substituted or unsubstituted 5 or 6 membered heteroaryl.

In embodiments, $R^{2a}$ is a $R^{2b}$-substituted or unsubstituted 3-6 membered heterocycloalkyl, $R^{2b}$-substituted or unsubstituted phenyl, or $R^{2b}$-substituted or unsubstituted 5 or 6 membered heteroaryl. In embodiments, $R^{2a}$ is an unsubstituted 3-6 membered heterocycloalkyl, unsubstituted phenyl, or unsubstituted 5 or 6 membered heteroaryl. In embodiments, $R^{2a}$ is an unsubstituted 5 or 6 membered heteroaryl. In embodiments, $R^{2a}$ is an unsubstituted pyridinyl. In embodiments, $R^{2a}$ is —C(CF$_3$)$_2$OH. In embodiments, $R^{2a}$ is —C(CF$_3$)$_3$.

$R^{2b}$ is independently hydrogen, halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_3$H, —SO$_4$H, —SO$_2$NH$_2$, —NHNH$_2$, —ONH$_2$, —NHC(O)NHNH$_2$, unsubstituted C$_1$-C$_8$ alkyl, unsubstituted 2-8 membered heteroalkyl, unsubstituted C$_3$-C$_8$ cycloalkyl, unsubstituted 3-6 membered heterocycloalkyl, unsubstituted phenyl, or unsubstituted 5 or 6 membered heteroaryl. In embodiments, $R^{2b}$ is independently halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_3$H, —SO$_4$H, —SO$_2$NH$_2$, —NHNH$_2$, —ONH$_2$, —NHC(O)NHNH$_2$. In embodiments, $R^{2b}$ is independently —CF$_3$, —CCl$_3$, —CBr$_3$, —CI$_3$, —CN, —CHO, —OH, —NH$_2$, —COOH, or —CONH$_2$. In embodiments, $R^{2b}$ is independently —CF$_3$ or —OH.

In embodiments, $R^9$ is independently hydrogen, halogen, —CN, —CF$_3$, —CCl$_3$, —CBr$_3$, —CI$_3$, —OH, —NH$_2$, $R^{20}$-substituted or unsubstituted alkylene (e.g. C$_1$-C$_8$ alkylene, C$_1$-C$_6$ alkylene, or C$_1$-C$_4$ alkylene), $R^{20}$-substituted or unsubstituted heteroalkylene (e.g. 2 to 10 membered heteroalkylene, 2 to 8 membered heteroalkylene, 4 to 8 membered heteroalkylene, 2 to 6 membered heteroalkylene, or 2 to 4 membered heteroalkylene), $R^{20}$-substituted or unsubstituted cycloalkylene (e.g. C$_3$-C$_8$ cycloalkylene, C$_4$-C$_8$ cycloalkylene, or C$_5$-C$_6$ cycloalkylene), $R^{20}$-substituted or unsubstituted heterocycloalkylene (e.g. 3 to 8 membered heterocycloalkylene, 4 to 8 membered heterocycloalkylene, or 5 to 6 membered heterocycloalkylene), R20-substituted or unsubstituted arylene (e.g. C$_6$-C$_{10}$ arylene or C$_6$ arylene), or $R^{20}$-substituted or unsubstituted heteroarylene (e.g. 5 to 10 membered heteroarylene, 5 to 9 membered heteroarylene, or 5 to 6 membered heteroarylene).

In embodiments, $R^{10}$ is independently hydrogen, halogen, —CN, —CF$_3$, —CCl$_3$, —CBr$_3$, —CI$_3$, —OH, —NH$_2$, $R^{21}$-substituted or unsubstituted alkylene (e.g. C$_1$-C$_8$ alkylene, C$_1$-C$_6$ alkylene, or C$_1$-C$_4$ alkylene), $R^{21}$-substituted or unsubstituted heteroalkylene (e.g. 2 to 10 membered heteroalkylene, 2 to 8 membered heteroalkylene, 4 to 8 membered heteroalkylene, 2 to 6 membered heteroalkylene, or 2 to 4 membered heteroalkylene), $R^{21}$-substituted or unsubstituted cycloalkylene (e.g. C$_3$-C$_8$ cycloalkylene, C$_4$-C$_8$ cycloalkylene, or C$_5$-C$_6$ cycloalkylene), $R^{21}$-substituted or unsubstituted heterocycloalkylene (e.g. 3 to 8 membered heterocycloalkylene, 4 to 8 membered heterocycloalkylene, or 5 to 6 membered heterocycloalkylene), R21-substituted or unsubstituted arylene (e.g. C$_6$-C$_{10}$ arylene or C$_6$ arylene), or $R^{21}$-substituted or unsubstituted heteroarylene (e.g. 5 to 10 membered heteroarylene, 5 to 9 membered heteroarylene, or 5 to 6 membered heteroarylene).

In embodiments, $R^{11}$ is independently hydrogen, halogen, —CN, —CF$_3$, —CCl$_3$, —CBr$_3$, —CI$_3$, —OH, —NH$_2$, $R^{22}$-substituted or unsubstituted alkylene (e.g. C$_1$-C$_8$ alkylene, C$_1$-C$_6$ alkylene, or C$_1$-C$_4$ alkylene), $R^{22}$-substituted or unsubstituted heteroalkylene (e.g. 2 to 10 membered heteroalkylene, 2 to 8 membered heteroalkylene, 4 to 8 membered heteroalkylene, 2 to 6 membered heteroalkylene, or 2 to 4 membered heteroalkylene), $R^{22}$-substituted or unsubstituted cycloalkylene (e.g. C$_3$-C$_8$ cycloalkylene, C$_4$-C$_8$ cycloalkylene, or C$_5$-C$_6$ cycloalkylene), $R^{22}$-substituted or unsubstituted heterocycloalkylene (e.g. 3 to 8 membered heterocycloalkylene, 4 to 8 membered heterocycloalkylene, or 5 to 6 membered heterocycloalkylene), $R^{22}$-substituted or unsubstituted arylene (e.g. C$_6$-C$_{10}$ arylene or C$_6$ arylene), or $R^{22}$-substituted or unsubstituted heteroarylene (e.g. 5 to 10 membered heteroarylene, 5 to 9 membered heteroarylene, or 5 to 6 membered heteroarylene).

In embodiments, $R^{11}$ is independently hydrogen, halogen, —CN, —CF$_3$, —CCl$_3$, —CBr$_3$, —CI$_3$, —OH, —NH$_2$, $R^{22}$-substituted or unsubstituted alkylene (e.g. C$_1$-C$_8$ alkylene, C$_1$-C$_6$ alkylene, or C$_1$-C$_4$ alkylene), $R^{22}$-substituted or unsubstituted heteroalkylene (e.g. 2 to 10 membered heteroalkylene, 2 to 8 membered heteroalkylene, 4 to 8 membered heteroalkylene, 2 to 6 membered heteroalkylene, or 2 to 4 membered heteroalkylene), $R^{22}$-substituted or unsubstituted cycloalkylene (e.g. C$_3$-C$_8$ cycloalkylene, C$_4$-C$_8$ cycloalkylene, or C$_5$-C$_6$ cycloalkylene), $R^{22}$-substituted or unsubstituted heterocycloalkylene (e.g. 3 to 8 membered heterocycloalkylene, 4 to 8 membered heterocycloalkylene, or 5 to 6 membered heterocycloalkylene), $R^{22}$-substituted or unsubstituted arylene (e.g. C$_6$-C$_{10}$ arylene or C$_6$ arylene), or $R^{22}$-substituted or unsubstituted heteroarylene (e.g. 5 to 10 membered heteroarylene, 5 to 9 membered heteroarylene, or 5 to 6 membered heteroarylene).

In embodiments, $R^{12}$ is independently hydrogen, halogen, —CN, —CF$_3$, —CCl$_3$, —CBr$_3$, —CI$_3$, —OH, —NH$_2$, $R^{23}$-substituted or unsubstituted alkylene (e.g. C$_1$-C$_8$ alkylene, C$_1$-C$_6$ alkylene, or C$_1$-C$_4$ alkylene), $R^{23}$-substituted or unsubstituted heteroalkylene (e.g. 2 to 10 membered heteroalkylene, 2 to 8 membered heteroalkylene, 4 to 8 membered heteroalkylene, 2 to 6 membered heteroalkylene, or 2 to 4 membered heteroalkylene), $R^{23}$-substituted or unsubstituted cycloalkylene (e.g. C$_3$-C$_8$ cycloalkylene, C$_4$-C$_8$ cycloalkylene, or C$_5$-C$_6$ cycloalkylene), $R^{23}$-substituted or unsubstituted heterocycloalkylene (e.g. 3 to 8 membered heterocycloalkylene, 4 to 8 membered heterocycloalkylene, or 5 to 6 membered heterocycloalkylene), $R^{23}$-substituted or unsubstituted arylene (e.g. C$_6$-C$_{10}$ arylene or C$_6$ arylene), or $R^{23}$-substituted or unsubstituted heteroarylene (e.g. 5 to 10 membered heteroarylene, 5 to 9 membered heteroarylene, or 5 to 6 membered heteroarylene).

In embodiments, $R^{13}$ is independently hydrogen, halogen, —CN, —CF$_3$, —CCl$_3$, —CBr$_3$, —CI$_3$, —OH, —NH$_2$, $R^{24}$-substituted or unsubstituted alkylene (e.g. C$_1$-C$_8$ alkylene, C$_1$-C$_6$ alkylene, or C$_1$-C$_4$ alkylene), $R^{24}$-substituted or unsubstituted heteroalkylene (e.g. 2 to 10 membered heteroalkylene, 2 to 8 membered heteroalkylene, 4 to 8 membered heteroalkylene, 2 to 6 membered heteroalkylene, or 2 to 4 membered heteroalkylene), $R^{24}$-substituted or unsubstituted cycloalkylene (e.g. C$_3$-C$_8$ cycloalkylene, C$_4$-C$_8$ cycloalkylene, or C$_5$-C$_6$ cycloalkylene), $R^{24}$-substituted or unsubstituted heterocycloalkylene (e.g. 3 to 8 membered heterocycloalkylene, 4 to 8 membered heterocycloalkylene, or 5 to 6 membered heterocycloalkylene), $R^{24}$-substituted or unsubstituted arylene (e.g. $C_6$-$C_{10}$ arylene or $C_6$ arylene), or $R^{24}$-substituted or unsubstituted heteroarylene (e.g. 5 to 10 membered heteroarylene, 5 to 9 membered heteroarylene, or 5 to 6 membered heteroarylene).

In embodiments, $R^{14}$ is independently hydrogen, halogen, —CN, —$CF_3$, —$CCl_3$, —$CBr_3$, —$CI_3$, —OH, —$NH_2$, $R^{25}$-substituted or unsubstituted alkylene (e.g. $C_1$-$C_8$ alkylene, $C_1$-$C_6$ alkylene, or $C_1$-$C_4$ alkylene), $R^{25}$-substituted or unsubstituted heteroalkylene (e.g. 2 to 10 membered heteroalkylene, 2 to 8 membered heteroalkylene, 4 to 8 membered heteroalkylene, 2 to 6 membered heteroalkylene, or 2 to 4 membered heteroalkylene), $R^{25}$-substituted or unsubstituted cycloalkylene (e.g. $C_3$-$C_8$ cycloalkylene, $C_4$-$C_8$ cycloalkylene, or $C_5$-$C_6$ cycloalkylene), $R^{25}$-substituted or unsubstituted heterocycloalkylene (e.g. 3 to 8 membered heterocycloalkylene, 4 to 8 membered heterocycloalkylene, or 5 to 6 membered heterocycloalkylene), $R^{25}$-substituted or unsubstituted arylene (e.g. $C_6$-$C_{10}$ arylene or $C_6$ arylene), or $R^{25}$-substituted or unsubstituted heteroarylene (e.g. 5 to 10 membered heteroarylene, 5 to 9 membered heteroarylene, or 5 to 6 membered heteroarylene).

In embodiments, $R^{15}$ is independently hydrogen, halogen, —CN, —$CF_3$, —$CCl_3$, —$CBr_3$, —$CI_3$, —OH, —$NH_2$, $R^{26}$-substituted or unsubstituted alkylene (e.g. $C_1$-$C_8$ alkylene, $C_1$-$C_6$ alkylene, or $C_1$-$C_4$ alkylene), $R^{26}$-substituted or unsubstituted heteroalkylene (e.g. 2 to 10 membered heteroalkylene, 2 to 8 membered heteroalkylene, 4 to 8 membered heteroalkylene, 2 to 6 membered heteroalkylene, or 2 to 4 membered heteroalkylene), $R^{26}$-substituted or unsubstituted cycloalkylene (e.g. $C_3$-$C_8$ cycloalkylene, $C_4$-$C_8$ cycloalkylene, or $C_5$-$C_6$ cycloalkylene), $R^{26}$-substituted or unsubstituted heterocycloalkylene (e.g. 3 to 8 membered heterocycloalkylene, 4 to 8 membered heterocycloalkylene, or 5 to 6 membered heterocycloalkylene), $R^{26}$-substituted or unsubstituted arylene (e.g. $C_6$-$C_{10}$ arylene or $C_6$ arylene), or $R^{26}$-substituted or unsubstituted heteroarylene (e.g. 5 to 10 membered heteroarylene, 5 to 9 membered heteroarylene, or 5 to 6 membered heteroarylene).

In embodiments, $R^{16}$ is independently hydrogen, halogen, —CN, —$CF_3$, —$CCl_3$, —$CBr_3$, —$CI_3$, —OH, —$NH_2$, $R^{27}$-substituted or unsubstituted alkylene (e.g. $C_1$-$C_8$ alkylene, $C_1$-$C_6$ alkylene, or $C_1$-$C_4$ alkylene), $R^{27}$-substituted or unsubstituted heteroalkylene (e.g. 2 to 10 membered heteroalkylene, 2 to 8 membered heteroalkylene, 4 to 8 membered heteroalkylene, 2 to 6 membered heteroalkylene, or 2 to 4 membered heteroalkylene), $R^{27}$-substituted or unsubstituted cycloalkylene (e.g. $C_3$-$C_8$ cycloalkylene, $C_4$-$C_8$ cycloalkylene, or $C_5$-$C_6$ cycloalkylene), $R^{27}$-substituted or unsubstituted heterocycloalkylene (e.g. 3 to 8 membered heterocycloalkylene, 4 to 8 membered heterocycloalkylene, or 5 to 6 membered heterocycloalkylene), $R^{27}$-substituted or unsubstituted arylene (e.g. $C_6$-$C_{10}$ arylene or $C_6$ arylene), or $R^{27}$-substituted or unsubstituted heteroarylene (e.g. 5 to 10 membered heteroarylene, 5 to 9 membered heteroarylene, or 5 to 6 membered heteroarylene).

$R^{20}$, $R^{21}$, $R^{22}$, $R^{23}$, $R^{24}$, $R^{25}$, $R^{26}$, and $R^{27}$ are independently oxo, halogen, —F, —Cl, —Br, —I, —$CF_3$, —$CCl_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

In embodiments, n is 1. In embodiments, n is 2. In embodiments, n is 3. In embodiments, n is 4.

In embodiments, the compound has the formula:

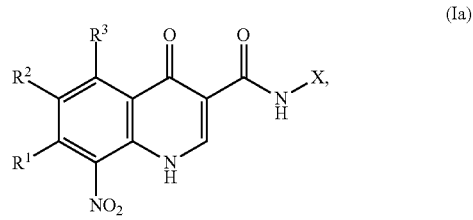

(Ia)

wherein $R^1$, $R^2$, $R^3$, and X are as described herein.

In embodiments, the compound has the formula:

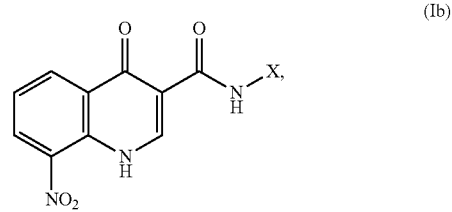

(Ib)

wherein X is as described herein.

In embodiments, the compound has the formula:

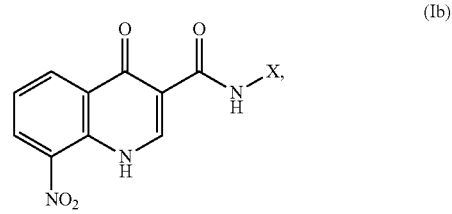

(Ib)

wherein X is a substituted or unsubstituted alkyl or a substituted or unsubstituted heteroalkyl.

In embodiments, the compound has the formula:

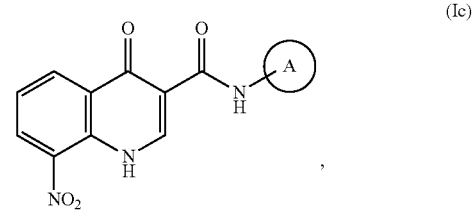

(Ic)

wherein Ring A is a substituted or unsubstituted cycloalkyl, substituted or unsubstituted heterocycloalkyl, substituted or unsubstituted aryl or substituted or unsubstituted heteroaryl.

In embodiments, Ring A is $R^{2a}$-substituted or unsubstituted $(C_6-C_{10})$ aryl or $R^{2a}$ substituted or unsubstituted 5 to 10 membered heteroaryl. Ring A may be $R^{2a}$-substituted or unsubstituted $(C_6-C_{10})$ aryl. Ring A may be $R^{2a}$-substituted or unsubstituted phenyl. Ring A may be $R^{2a}$-substituted or unsubstituted napthyl. Ring A may be $R^{2a}$-substituted or unsubstituted 5 to 10 membered heteroaryl. Ring A may be $R^{2a}$-substituted or unsubstituted 5 to 6 membered heteroaryl. Ring A may be $R^{2a}$-substituted or unsubstituted thienyl. Ring A may be $R^{2a}$-substituted or unsubstituted furanyl. Ring A may be $R^{2a}$-substituted or unsubstituted pyrrolyl. Ring A may be $R^{2a}$-substituted or unsubstituted imidazolyl. Ring A may be $R^{2a}$-substituted or unsubstituted pyrazolyl. Ring A may be $R^{2a}$-substituted or unsubstituted oxazolyl. Ring A may be $R^{2a}$-substituted or unsubstituted isoxazolyl. Ring A may be $R^{2a}$-substituted or unsubstituted thiazolyl. Ring A may be $R^{2a}$-substituted or unsubstituted pyridinyl. Ring A may be $R^{2a}$-substituted or unsubstituted pyridyl. Ring A may be $R^{2a}$-substituted or unsubstituted pyrazinyl. Ring A may be $R^{2a}$-substituted or unsubstituted pyrimidinyl. Ring A may be $R^{2a}$-substituted or unsubstituted pyridazinyl. Ring A may be $R^{2a}$-substituted or unsubstituted 1,2,3-triazinyl. Ring A may be $R^{2a}$-substituted or unsubstituted 1,2,4-triazinyl. Ring A may be $R^{2a}$-substituted or unsubstituted 1,3,5-triazinyl. In embodiments, Ring A is $R^{2a}$-substituted $(C_6-C_{10})$ aryl or $R^{2a}$ substituted 5 to 10 membered heteroaryl. Ring A may be $R^{2a}$-substituted $(C_6-C_{10})$ aryl. Ring A may be $R^{2a}$-substituted phenyl. Ring A may be $R^{2a}$-substituted napthyl. Ring A may be $R^{2a}$-substituted 5 to 10 membered heteroaryl. Ring A may be $R^{2a}$-substituted 5 to 6 membered heteroaryl. Ring A may be $R^{2a}$-substituted thienyl. Ring A may be $R^{2a}$-substituted furanyl. Ring A may be $R^{2a}$-substituted pyrrolyl. Ring A may be $R^{2a}$-substituted imidazolyl. Ring A may be $R^{2a}$-substituted pyrazolyl. Ring A may be $R^{2a}$-substituted oxazolyl. Ring A may be $R^{2a}$-substituted isoxazolyl. Ring A may be $R^{2a}$-substituted thiazolyl. Ring A may be $R^{2a}$-substituted pyridinyl. Ring A may be $R^{2a}$-substituted pyridyl. Ring A may be $R^{2a}$-substituted pyrazinyl. Ring A may be $R^{2a}$-substituted pyrimidinyl. Ring A may be $R^{2a}$-substituted pyridazinyl. Ring A may be $R^{2a}$-substituted 1,2,3-triazinyl. Ring A may be $R^{2a}$-substituted 1,2,4-triazinyl. Ring A may be $R^{2a}$-substituted 1,3,5-triazinyl. Ring A may be substituted with one $R^{2a}$. Ring A may be substituted with two optionally different $R^{2a}$ substituents. Ring A may be substituted with three optionally different $R^{2a}$ substituents. Ring A may be substituted with four optionally different $R^{2a}$ substituents. Ring A may be substituted with five optionally different $R^{2a}$ substituents.

Ring A may be unsubstituted thienyl. Ring A may be unsubstituted furanyl. Ring A may be unsubstituted pyrrolyl. Ring A may be unsubstituted imidazolyl. Ring A may be unsubstituted pyrazolyl. Ring A may be unsubstituted oxazolyl. Ring A may be unsubstituted isoxazolyl. Ring A may be unsubstituted thiazolyl. Ring A may be unsubstituted pyridinyl. Ring A may be unsubstituted pyridyl. Ring A may be unsubstituted pyrazinyl. Ring A may be unsubstituted pyrimidinyl. Ring A may be unsubstituted pyridazinyl. Ring A may be unsubstituted 1,2,3-triazinyl. Ring A may be unsubstituted 1,2,4-triazinyl. Ring A may be unsubstituted 1,3,5-triazinyl.

In embodiments, the compound has the formula:

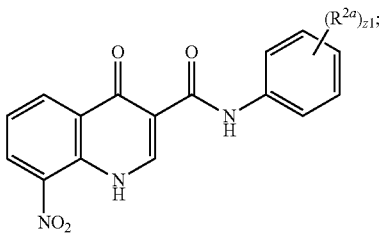

wherein $R^{2a}$ is as defined herein and the symbol z1 is an integer from 0 to 5. In embodiments, z1 is 0 or 1. In embodiments, z1 is 0. In embodiments, z1 is 1. In embodiments, z1 is 2. In embodiments, z1 is 3. In embodiments, z1 is 4. In embodiments, z1 is 5.

In embodiments, the compound has the formula:

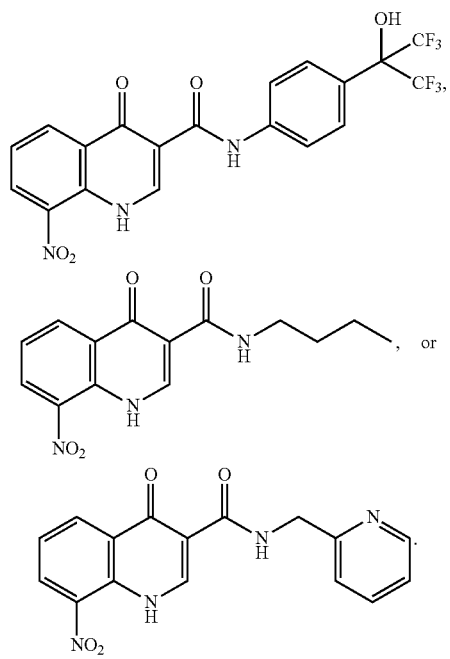

In embodiments, the compound has the formula:

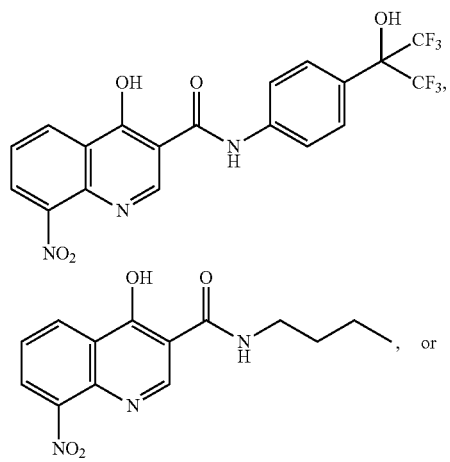

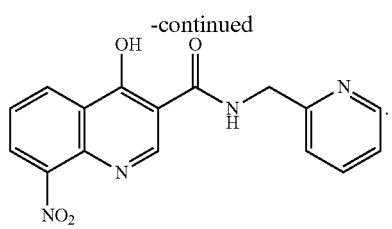

In embodiments, the compound has the formula:

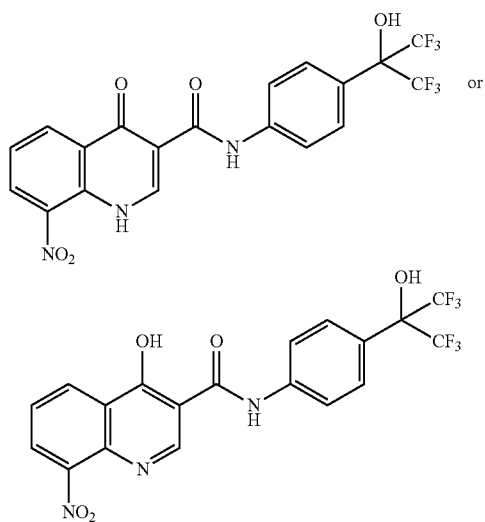

(also referred to herein as C5-1).

In embodiments, the compound has the formula:

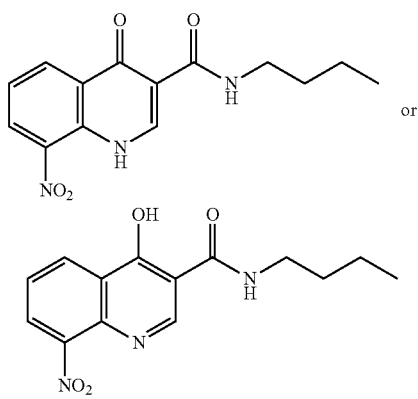

(also referred to herein as C5-2).

In embodiments, the compound has the formula

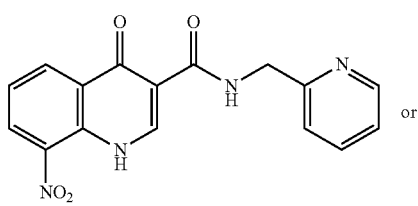

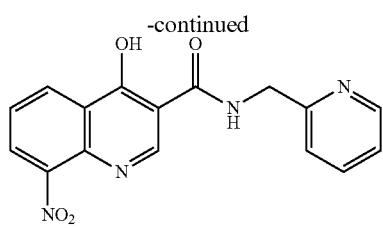

(also referred to herein as C5-3).

In embodiments, there is a proviso that the compound of Formula (I) is not a compound wherein the substituents are concurrently the following: $R^1$, $R^2$, and $R^3$ are hydrogen; L is —C(O)—; X is —OR$^{14}$; and $R^{14}$ is hydrogen. In embodiments, the compound is not:

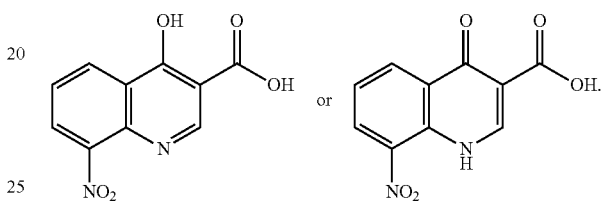

In embodiments, the compound is not:

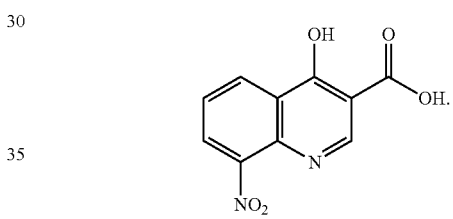

In embodiments, the compound is not:

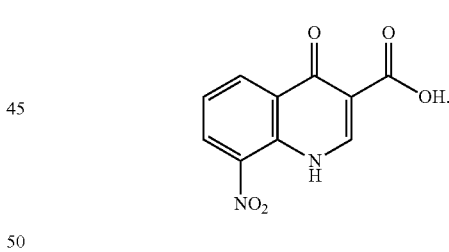

III. Pharmaceutical Compositions

In another aspect, is provided a pharmaceutical composition including a pharmaceutically acceptable excipient and a compound as described herein or a pharmaceutically acceptable salt thereof.

The pharmaceutical compositions may include optical isomers, diastereomers, or pharmaceutically acceptable salts of the compounds disclosed herein. The compound included in the pharmaceutical composition may be covalently attached to a carrier moiety. Alternatively, the compound included in the pharmaceutical composition is not covalently linked to a carrier moiety.

The compounds of the present invention can be prepared and administered in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compounds of the present invention can also be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable excipient and one or more compounds of the invention.

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of cancer symptoms. Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g., cancer, breast cancer, colon cancer, prostate cancer, lung cancer, or ovarian cancer), kind of concurrent treatment, complications from the disease being treated or other health-related problems. Other therapeutic regimens or agents can be used in conjunction with the methods and compounds described herein. Adjustment and manipulation of established dosages (e.g., frequency and duration) are well within the ability of those skilled in the art.

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration and dosage can be chosen by the individual physician in view of the patient's condition and the particular method in which the compound is used.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compositions described herein of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

In another embodiment, the compositions of the present invention are useful for parenteral administration, such as intravenous (IV) administration or administration into a body cavity or lumen of an organ. The formulations for administration will commonly include a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The compounds described herein can be used in combination with one another, with other active agents known to be useful in treating a disease associated with cells expressing folate transporters (e.g. breast cancer, colon cancer, prostate cancer, lung cancer, or ovarian cancer), or with adjunctive agents that may not be effective alone, but may contribute to the efficacy of the active agent.

In embodiments, the compositions and compounds of Formula (I) described herein can be co-administered with conventional chemotherapeutic agents including alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, methotrexate, leucovorin, capecitabine, cytarabine, floxuridine, fludarabine, gemcitabine, pemetrexed, raltitrexed, etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), and the like. In embodiments, the compound of Formula (I) is administered prior to the chemotherapeutic agent.

In other embodiments, the pharmaceutical compositions described herein comprise a compound of Formula (I) or a pharmaceutically acceptable salt thereof; a chemotherapeutic agent (such as alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, methotrexate, leucovorin, capecitabine, cytarabine, floxuridine, fludarabine, gemcitabine, pemetrexed, raltitrexed, etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin); and a pharmaceutically acceptable excipient.

The compounds or drugs described herein can also be co-administered with conventional hormonal therapeutic agents including, but not limited to, steroids (e.g., dexamethasone), finasteride, aromatase inhibitors, tamoxifen, and gonadotropin-releasing hormone agonists (GnRH) such as goserelin. In embodiments, the compound of Formula (I) is administered prior to the hormonal therapeutic agent.

In other embodiments, the pharmaceutical compositions described herein comprise a compound of Formula (I) or (II) or a pharmaceutically acceptable salt thereof; a hormonal therapeutic agent (including, but not limited to, steroids (e.g., dexamethasone), finasteride, aromatase inhibitors, tamoxifen, and gonadotropin-releasing hormone agonists (GnRH) such as goserelin); and a pharmaceutically acceptable excipient.

The compounds or drugs described herein can also be co-administered with PARP inhibiting agents (e.g., PARP inhibitors) including, but not limited to 4-iodo-3-nitrobenzamide, 4-[(3-[(4-cyclopropylcarbonyl)piperazin-4-yl]carbonyl)-4-fluorophenyl]methyl(2H)phthalazin-1-one, 8-Fluoro-2-{4-[(methylamino)methyl]phenyl}-1,3,4,5-tetrahydro-6H-azepino[5,4,3-cd]indol-6-one, 2-((R)-2-Methylpyrrolidin-2-yl)-1H-benzimidazole-4-carboxamide, and 3-aminobenzamide. In embodiments, the compound of Formula (I) or (II) is administered prior to the PARP inhibiting agent.

In other embodiments, the pharmaceutical compositions described herein comprise a compound of Formula (I) or (II) or a pharmaceutically acceptable salt thereof; a PARP inhibiting agent (including, but not limited to 4-iodo-3-nitrobenzamide, 4-[(3-[(4-cyclopropylcarbonyl)piperazin-4-yl]carbonyl)-4-fluorophenyl]methyl(2H)phthalazin-1-one, 8-Fluoro-2-{4-[(methylamino)methyl]phenyl}-1,3,4,5-tetrahydro-6H-azepino[5,4,3-cd]indol-6-one, 2-((R)-2-Methylpyrrolidin-2-yl)-1H-benzimidazole-4-carboxamide, and 3-aminobenzamide); and a pharmaceutically acceptable excipient.

In a further embodiment, the compounds or drugs described herein can be co-administered with conventional radiopharmaceuticals including, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens. In embodiments, the compound of Formula (I) or (II) is administered prior to the radiopharmaceutical.

In other embodiments, the pharmaceutical compositions described herein comprise a compound of Formula (I) or (II) or a pharmaceutically acceptable salt thereof; a radiopharmaceutical (including, but not limited to, radionuclides such as $^{47}$Sc, $^{64}$Cu, $^{67}$Cu, $^{89}$Sr, $^{86}$Y, $^{87}$Y, $^{90}$, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens); and a pharmaceutically acceptable excipient.

The pharmaceutical compositions of the present invention may be sterilized by conventional, well-known sterilization techniques or may be produced under sterile conditions. Aqueous solutions can be packaged for use or filtered under aseptic+conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents, and the like, e.g., sodium acetate, sodium lactate, sodium chloride, potassium chloride, calcium chloride, sorbitan monolaurate, and triethanolamine oleate.

Formulations suitable for oral administration can comprise: (a) liquid solutions, such as an effective amount of a packaged compound or drug suspended in diluents, e.g., water, saline, or PEG 400; (b) capsules, sachets, or tablets, each containing a predetermined amount of a compound or drug, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise a compound or drug in a flavor, e.g., sucrose, as well as pastilles comprising the polypeptide or peptide fragment in an inert base, such as gelatin and glycerin or sucrose and acacia emulsions, gels, and the like, containing, in addition to the polypeptide or peptide, carriers known in the art.

The compound or drug of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which comprises an effective amount of a packaged compound or drug with a suppository base. Suitable suppository bases include natural or synthetic triglycerides or paraffin hydrocarbons. In addition, it is also possible to use gelatin rectal capsules which contain a combination of the compound or drug of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can also be prepared from sterile powders, granules, and tablets. In the practice of the present invention, compositions can be administered, for example, by intravenous infusion, orally, topically, intraperitoneally, intravesically, or intrathecally. Parenteral administration, oral administration, and intravenous administration are the preferred methods of administration. The formulations of compounds can be presented in unit-dose or multi-dose sealed containers, such as ampoules and vials.

The pharmaceutical preparation is preferably in unit dosage form. In such form the preparation is subdivided into unit doses containing appropriate quantities of the active component, e.g., a compound or drug. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

IV. Methods of Treatment

In an aspect is provided, a method of treating cancer in a patient in need thereof including administering to the patient a therapeutically effective amount of a pharmaceutical composition as described herein to treat the cancer in the patient.

In an aspect is provided, a method of treating cancer in a patient in need thereof including administering to the patient a therapeutically effective amount of a compound as described herein, and a chemotherapeutic agent, radiation, or a combination thereof, to treat the cancer in the patient. In embodiments, the compound as described herein is administered prior to the chemotherapeutic agent, radiation, or a combination thereof. In embodiments, the compound as described herein is administered concurrently with the chemotherapeutic agent, radiation, or a combination thereof. The concurrent administration may be separate pharmaceutical compositions or may be a single pharmaceutical composition. The single pharmaceutical composition for treating cancer may comprise a compound described herein or a pharmaceutically acceptable salt thereof; one or more chemotherapeutic agents; and a pharmaceutically acceptable excipient. The single pharmaceutical composition for treating cancer may comprise a compound described herein or a pharmaceutically acceptable salt thereof; one or more radiopharmaceuticals; and a pharmaceutically acceptable excipient. The single pharmaceutical composition for treating cancer may comprise a compound described herein or a pharmaceutically acceptable salt thereof; one or more chemotherapeutic agents; one or more radiopharmaceuticals; and a pharmaceutically acceptable excipient. The cancer may be breast, colon, prostate, lung, or ovarian cancer.

In an aspect is provided a method of sensitizing cancer cells to radiation therapy or chemotherapy including administering the compound as described herein to the cancer cells in vitro or in vivo to sensitize the cancer cells to radiation therapy or chemotherapy. In embodiments, the method of sensitizing cancer cells to radiation therapy or chemotherapy includes administering the compound as described herein to the cancer cells in vitro to sensitize the cancer cells to radiation therapy or chemotherapy. In embodiments, the method of sensitizing cancer cells to radiation therapy or chemotherapy includes administering the compound as described herein to the cancer cells in vivo to sensitize the cancer cells to radiation therapy or chemotherapy. In embodiments, the method of sensitizing cancer cells to radiation therapy includes administering the compound as described herein to the cancer cells in vitro or in vivo to sensitize the cancer cells to radiation therapy. In embodiments, the method of sensitizing cancer cells to chemotherapy includes administering the compound as described herein to the cancer cells in vitro or in vivo to sensitize the cancer cells to chemotherapy.

In another aspect is provided a method of potentiating the clinical efficacy of a PARP inhibitor including co-administering the compound as described herein with the PARP inhibitor to potentiate the clinical efficacy of the PARP inhibitor. In this embodiment, the PARP inhibitor will exhibit improved clinical efficacy when co-administered with the compounds described herein than if the PARP inhibitor was administered without the compounds described herein.

Provided in an aspect is a method of potentiating the clinical efficacy of a topoisomerase inhibitor including administering the compound as described herein in conjunction with the topoisomerase inhibitor to potentiate the clinical efficacy of the topoisomerase inhibitor. In embodiments, the topoisomerase inhibitor is irinotecan, topotecan, camptothecin, lamellarin D, etoposide, teniposide, doxorubicin, daunorubicin, mitoxantrone, amsacrine, ellipticines, aurintricarboxylic acid, a quinolone synthesized from cannabidiol (e.g., HU-331), or plant-derived phenols (e.g., epigallocatechin gallate, genistein, quercetin, or resveratrol). In embodiments, the topoisomerase inhibitor is a topoisomerase I inhibitor. In embodiments, the topoisomerase inhibitor is irinotecan, topotecan, camptothecin, lamellarin D. In embodiments, the topoisomerase inhibitor is camptothecin. In this embodiment, the topoisomerase inhibitor will exhibit improved clinical efficacy when co-administered with the compounds described herein than if the topoisomerase inhibitor was administered without the compounds described herein.

In embodiments, the chemotherapeutic agent is a PARP inhibitor, topoisomerase inhibitor, or topoisomerase I inhibitor. In embodiments, the chemotherapeutic agent is a PARP inhibitor. In embodiments, the chemotherapeutic agent is a topoisomerase inhibitor. In embodiments, the chemotherapeutic agent is a topoisomerase I inhibitor. In embodiments, the chemotherapeutic agent is irinotecan, topotecan, camptothecin, lamellarin D, etoposide, teniposide, doxorubicin, daunorubicin, mitoxantrone, amsacrine, ellipticines, aurintricarboxylic acid, a quinolone synthesized from cannabidiol (e.g., HU-331), or plant-derived phenols (e.g., epigallocatechin gallate, genistein, quercetin, or resveratrol).

In embodiments, the cancer is breast cancer, colon cancer, prostate cancer, lung cancer, or ovarian cancer. In embodiments, the cancer is breast cancer. In embodiments, the cancer is colon cancer. In embodiments, the cancer is prostate cancer. In embodiments, the cancer is lung cancer. In embodiments, the cancer is ovarian cancer.

In an aspect is provided a method of inhibiting DNA replication in cells including administering the compound as described herein in vitro or in vivo to the cells to inhibit DNA replication. In embodiments, the method of inhibiting DNA replication in cells includes administering the compound as described herein in vitro to the cells to inhibit DNA replication. In embodiments, the method of inhibiting DNA replication in cells includes administering the compound as described herein in vivo to the cells to inhibit DNA replication. In embodiments, the method includes interfering with telomere replication or repait.

In an aspect is provided a method of inhibiting DNA replication in a patient in need thereof including administering the compound as described herein to the patient to inhibit DNA replication in the patient.

Provided in an aspect is a method of suppressing DNA double-strand break repair end resection, recombination, over-resection of nascent DNA in cells defective in fork protection, and restart of stalled DNA replication forks in cells or a patient in need thereof including administering the compound as described herein in vitro or in vivo to cells or the patient to suppress DNA double-strand break repair end resection, recombination, over-resection of nascent DNA in cells defective in fork protection, and restart of stalled DNA replication forks. In embodiments, the method of suppressing DNA double-strand break repair end resection, recombination, over-resection of nascent DNA in cells defective in fork protection, and restart of stalled DNA replication forks in cells or a patient in need thereof further includes administering a chemotherapeutic agent, radiation, or a combination thereof. In embodiments, the method of suppressing DNA double-strand break repair includes inhibiting replication, inhibiting resection, inhibiting telomere homeostasis, or inhibiting DNA protein activity. In embodiments, the method includes interfering with telomere replication or repair.

In an aspect is provided a pharmaceutical composition including the compound as described herein; a chemotherapeutic agent; and a pharmaceutically acceptable carrier.

In an aspect is provided, a pharmaceutical composition including the compound as described herein; a PARP inhibitor; and a pharmaceutically acceptable carrier.

In an aspect is provided, a pharmaceutical composition including the compound as described herein; a topoisomerase inhibitor; and a pharmaceutically acceptable carrier.

In an aspect is provided, a pharmaceutical composition including the compound as described herein; a radiopharmaceutical; and a pharmaceutically acceptable carrier.

In an aspect is provided, a pharmaceutical composition including the compound as described herein; a chemotherapeutic agent; a radiopharmaceutical; and a pharmaceutically acceptable carrier.

In an aspect is provided, a method of treating Fanconi anemia in a patient in need thereof including administering to the patient a therapeutically effective amount of the compound or pharmaceutical composition as described herein. In embodiments, the patient further has cancer (e.g., leukemias and solid tumors of the head and neck). In embodiments, the patient has both cancer (e.g., leukemias and solid tumors of the head and neck) and Fanconi anemia.

In embodiments of the methods described herein, the compound has the formula:

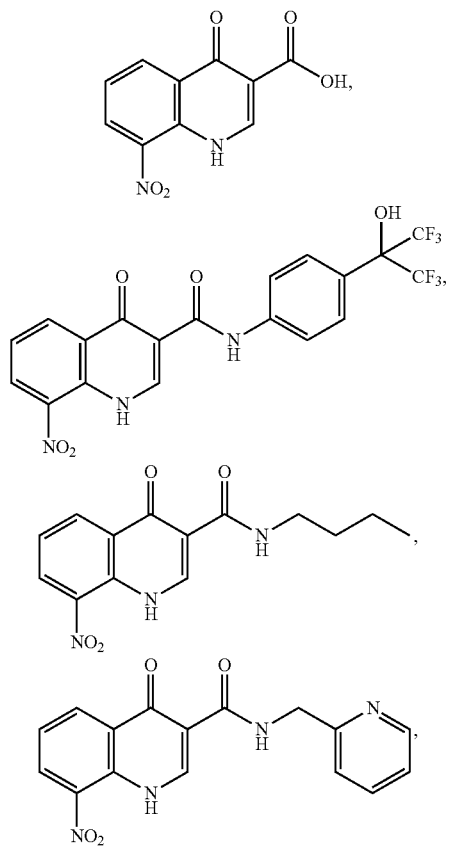 [SMILES: O=C(O)c1c[nH]c2c([N+](=O)[O-])cccc2c1=O ; O=C(Nc1ccc(C(O)(C(F)(F)F)C(F)(F)F)cc1)c1c[nH]c2c([N+](=O)[O-])cccc2c1=O ; CCCCNC(=O)c1c[nH]c2c([N+](=O)[O-])cccc2c1=O ; O=C(NCc1ccccn1)c1c[nH]c2c([N+](=O)[O-])cccc2c1=O]

or a tautomer of any one of the foregoing.

In embodiments of the methods described herein, the compound has the formula:

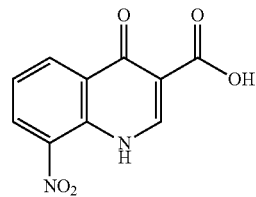 [SMILES: O=C(O)c1c[nH]c2c([N+](=O)[O-])cccc2c1=O]

or a tautomer thereof.

In embodiments of the methods described herein, the compound has the formula:

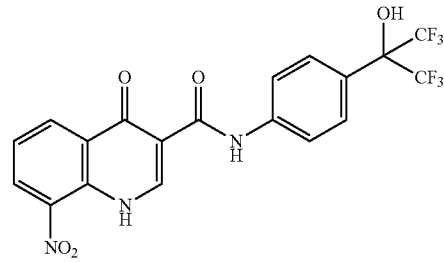 [SMILES: O=C(Nc1ccc(C(O)(C(F)(F)F)C(F)(F)F)cc1)c1c[nH]c2c([N+](=O)[O-])cccc2c1=O]

or a tautomer thereof.

In embodiments of the methods described herein, the compound has the formula:

53

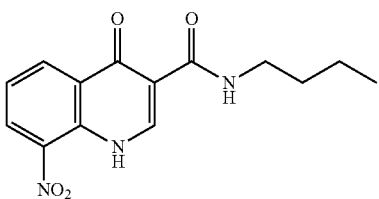 [SMILES: CCCCNC(=O)c1c[nH]c2c([N+](=O)[O-])cccc2c1=O]

or a tautomer thereof.

In embodiments of the methods described herein, the compound has the formula:

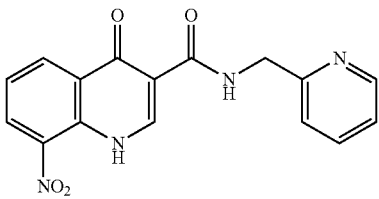 [SMILES: O=C(NCc1ccccn1)c1c[nH]c2c([N+](=O)[O-])cccc2c1=O]

or a tautomer thereof.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

V. Embodiments

Embodiment P1

A compound of Formula (I):

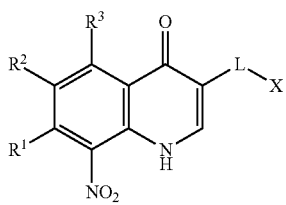

(I)

wherein $R^1$, $R^2$, and $R^3$ are each independently hydrogen, halogen, —$N_3$, —NHC=(O)NHNH$_2$, —CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)$_n$R$^{13}$, —S(O)$_n$NR$^9$R$^{10}$, —NR$^{12}$S(O)$_n$R$^{13}$, —NO$_2$, —OR$^{14}$, —SR$^{14}$, —NR$^{15}$, —OCOR$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

L is a bond, —C(O)—NH—, —NH—C(O)—, —C(O)—, —C(O)—O—, —NH—, —O—, —S—, —S(O)—, —S(O)$_2$—, —NH—S(O)—, —NH—S(O)$_2$—, —CH$_2$N(C(O)OH)—, —CH$_2$—N(CH(O))—, —CH$_2$—N(SO$_2$)—, —CH$_2$NH—, —CH$_2$C(O)NH—,

54

—CH$_2$NHC(O)—, —CH$_2$NHS(O)—, —CH$_2$NHS(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

X is hydrogen, halogen, —$N_3$, —NHC=(O)NHNH$_2$, —CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)$_n$R$^{13}$, —S(O)$_n$NR$^9$R$^{10}$, —NR$^{12}$S(O)$_n$R$^{13}$, —NO$_2$, —OR$^{14}$, —SR$^{14}$, —NR$^{15}$, —OCOR$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$, $R^{10}$ $R^{11}$, $R^{12}$, $R^{13}$, $R^{14}$, $R^{15}$, and $R^{16}$, are independently hydrogen, halogen, —CN, —CF$_3$, —CCl$_3$, —CBr$_3$, —CI$_3$, —OH, —NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n is 1 to 4.

Embodiment P2

The compound of Embodiment P1, wherein L is —C(O)—NH—, —NH—C(O)—, —C(O)—, —C(O)—O—, —NH—, —O—, —S—, —S(O)—, —S(O)$_2$—, —NH—S(O)—, —NH—S(O)$_2$—, —CH$_2$N(C(O)OH)—, —CH$_2$—N(CH(O))—, —CH$_2$—N(SO$_2$)—, —CH$_2$NH—, —CH$_2$C(O)NH—, —CH$_2$NHC(O)—, —CH$_2$NHS(O)—, —CH$_2$NHS(O)$_2$—, unsubstituted $C_1$-$C_6$ alkylene, unsubstituted $C_1$-$C_6$ heteroalkylene, unsubstituted 5-6 membered cycloalkylene, 5-6 membered unsubstituted heterocycloalkylene, 5-6 membered unsubstituted arylene, or 5-6 membered or unsubstituted heteroarylene.

Embodiment P3

The compound of Embodiment P1, wherein L is —C(O)—NH—, —C(O)—, —C(O)—O—, —NH—, —O—, —S—, —S(O)—, or —S(O)$_2$—.

Embodiment P4

The compound of Embodiment P1, wherein L is —C(O)—NH— or —C(O)—O—.

Embodiment P5

The compound of Embodiment P1, wherein $R^1$, $R^2$, and $R^3$ are each independently hydrogen, halogen, —NH$_2$, —OH, —NO$_2$, —C(O)CH$_3$, —NHC(O)CH$_3$, —OC(O)CH$_3$, or unsubstituted $C_{1-4}$ alkyl.

Embodiment P6

The compound of Embodiment P1, wherein $R^1$, $R^2$, and $R^3$ are hydrogen.

Embodiment P7

The compound of Embodiment P1, wherein $R^1$, $R^2$, and $R^3$ are hydrogen, and L is —C(O)NH—.

Embodiment P8

The compound of any one of Embodiments P1 to P7, wherein X is hydrogen, halogen, —N$_3$, —NHC=(O)NHNH$_2$, —CN, —CF$_3$, —CCl$_3$, —CBr$_3$, —CI$_3$, —NR$^9$R$^{10}$, —C(O)R$^1$, —C(O)NR$^9$R$^{10}$, —NR$^{12}$C(O)R$^{11}$, —S(O)$_n$R$^{13}$, —S(O)$_n$NR$^9$R$^{10}$, —NR$^{12}$S(O)$_n$R$^{13}$, —NO$_2$, —OR$^{14}$, —SR$^{14}$, NR$^{15}$, or —OCOR$^{16}$.

Embodiment P9

The compound of any one of Embodiments P1 to P7, wherein X is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P10

The compound of any one of Embodiments P1 to P7, wherein X is R$^{2a}$-substituted or unsubstituted C$_1$-C$_8$ alkyl, R$^{2a}$-substituted or unsubstituted 2-8 membered heteroalkyl, R$^{2a}$-substituted or unsubstituted C$_3$-C$_8$ cycloalkyl, R$^{2a}$-substituted or unsubstituted 3-6 membered heterocycloalkyl, R$^{2a}$-substituted or unsubstituted phenyl, or R$^{2a}$-substituted or unsubstituted 5 or 6 membered heteroaryl;

R$^{2a}$ is independently hydrogen, halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_3$H, —SO$_4$H, —SO$_2$NH$_2$, —NHNH$_2$, —ONH$_2$, —NHC(O)NHNH$_2$, R$^{2b}$-substituted or unsubstituted C$_1$-C$_8$ alkyl, R$^{2b}$-substituted or unsubstituted 2-8 membered heteroalkyl, R$^{2b}$-substituted or unsubstituted C$_3$-C$_8$ cycloalkyl, R$^{2b}$-substituted or unsubstituted 3-6 membered heterocycloalkyl, R$^{2b}$-substituted or unsubstituted phenyl, or R$^{2b}$ substituted or unsubstituted 5 or 6 membered heteroaryl; and R$^{2b}$ is independently hydrogen, halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_3$H, —SO$_4$H, —SO$_2$NH$_2$, —NHNH$_2$, —ONH$_2$, —NHC(O)NHNH$_2$, unsubstituted C$_1$-C$_8$ alkyl, unsubstituted 2-8 membered heteroalkyl, unsubstituted C$_3$-C$_8$ cycloalkyl, unsubstituted 3-6 membered heterocycloalkyl, unsubstituted phenyl, or unsubstituted 5 or 6 membered heteroaryl.

Embodiment P11

The compound of any one of Embodiments P1 to P7, wherein X is unsubstituted C$_1$-C$_8$ alkyl, unsubstituted 2-8 membered heteroalkyl, unsubstituted C$_3$-C$_8$ cycloalkyl, unsubstituted 3-6 membered heterocycloalkyl, unsubstituted phenyl, or unsubstituted 5 or 6 membered heteroaryl.

Embodiment P12

The compound of any one of Embodiments P1 to P7, wherein X is substituted C$_1$-C$_8$ alkyl, substituted 2-8 membered heteroalkyl, substituted C$_3$-C$_8$ cycloalkyl, substituted 3-6 membered heterocycloalkyl, substituted phenyl, or substituted 5 or 6 membered heteroaryl.

Embodiment P13

The compound of Embodiment P1, with the proviso that the compound does not concurrently have substituents wherein R$_1$, R$_2$, and R$_3$ are hydrogen; L is —C(O)—; X is —OR$_{14}$; and R$^{14}$ is hydrogen.

Embodiment P14

A compound of the formula:

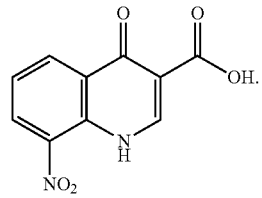 [SMILES: O=C(O)c1c[nH]c2c([N+](=O)[O-])cccc2c1=O]

Embodiment P15

A compound of the formula:

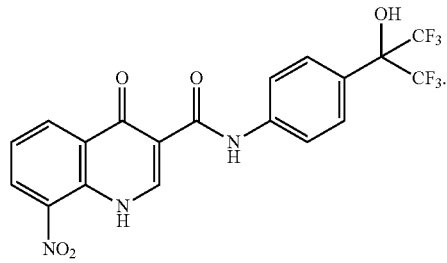

Embodiment P16

A compound of the formula:

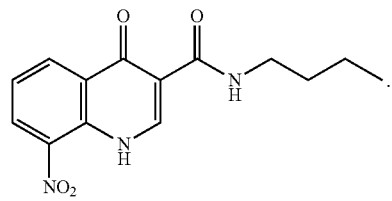

Embodiment P17

A compound of the formula:

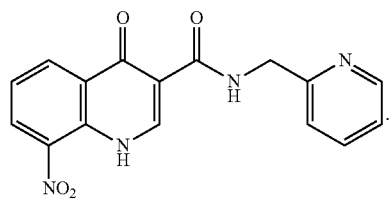 [SMILES: O=C(NCc1ccccn1)c1c[nH]c2c([N+](=O)[O-])cccc2c1=O]

Embodiment P18

A pharmaceutical composition comprising the compound of any one of Embodiments P1 to P17 and a pharmaceutically acceptable carrier.

Embodiment P19

A method of treating cancer in a patient in need thereof comprising administering to the patient a therapeutically effective amount of a compound of any one of Embodiments P1 to P17 to treat the cancer in the patient.

Embodiment P20

The method of Embodiment P19, wherein the cancer is breast cancer, colon cancer, prostate cancer, lung cancer, or ovarian cancer.

Embodiment P21

A method of treating cancer in a patient in need thereof comprising administering to the patient a therapeutically effective amount of a pharmaceutical composition of Embodiment P18 to treat the cancer in the patient.

Embodiment P22

The method of Embodiment P21, wherein the cancer is breast cancer, colon cancer, prostate cancer, lung cancer, or ovarian cancer.

Embodiment P23

A method of treating cancer in a patient in need thereof comprising administering to the patient a therapeutically effective amount of
  (i) a compound of any one of Embodiments P1 to P17, and
  (ii) a chemotherapeutic agent, radiation, or a combination thereof, to treat the cancer in the patient.

Embodiment P24

The method of Embodiment P23, wherein the cancer is breast cancer, colon cancer, prostate cancer, lung cancer, or ovarian cancer.

Embodiment P25

The method of Embodiment P23, wherein the chemotherapeutic agent is a PARP inhibitor.

Embodiment P26

The method of Embodiment P23, wherein the chemotherapeutic agent is a topoisomerase inhibitor.

Embodiment P27

The method of Embodiment P26, wherein the topoisomerase inhibitor is a topoisomerase I inhibitor.

Embodiment P28

The method of Embodiment P23, wherein (i) is administered prior to (ii).

Embodiment P29

The method of Embodiment P23, wherein (i) and (ii) are administered concurrently.

Embodiment P30

A method of sensitizing cancer cells to radiation therapy or chemotherapy comprising administering the compound of any one of Embodiments P1 to P17 to the cancer cells in vitro or in vivo to sensitize the cancer cells to radiation therapy or chemotherapy.

Embodiment P31

A method of potentiating the clinical efficacy of a PARP inhibitor comprising administering the compound of any one of Embodiments P1 to P17 in conjunction with the PARP inhibitor to potentiate the clinical efficacy of the PARP inhibitor.

Embodiment P32

A method of potentiating the clinical efficacy of a topoisomerase inhibitor comprising administering the compound of any one of Embodiments P1 to P17 in conjunction with the topoisomerase inhibitor to potentiate the clinical efficacy of the topoisomerase inhibitor.

Embodiment P33

The method of Embodiment P32, wherein the topoisomerase inhibitor is a topoisomerase I inhibitor.

Embodiment P34

A method of inhibiting DNA replication in cells comprising administering the compound of any one of Embodiments P1 to P17 in vitro or in vivo to the cells to inhibit DNA replication.

Embodiment P35

A method of inhibiting DNA replication in a patient in need thereof comprising administering the compound of any one of Embodiments P1 to P17 to the patient to inhibit DNA replication in the patient.

Embodiment P36

A method of suppressing DNA double-strand break repair end resection, recombination, over-resection of nascent DNA in cells defective in fork protection, and restart of stalled NDA replication forks in cells or a patient in need thereof comprising administering the compound of any one of Embodiments P1 to P17 in vitro or in vivo to cells or the patient to suppress DNA double-strand break repair end resection, recombination, over-resection of nascent DNA in cells defective in fork protection, and restart of stalled NDA replication forks.

Embodiment P37

The method of Embodiment P36, further comprising administering a chemotherapeutic agent, radiation, or a combination thereof.

Embodiment P38

A pharmaceutical composition comprising the compound of any one of Embodiments P1 to P17; a chemotherapeutic agent; and a pharmaceutically acceptable carrier.

Embodiment P39

A pharmaceutical composition comprising the compound of any one of Embodiments P1 to P17; a PARP inhibitor; and a pharmaceutically acceptable carrier.

Embodiment P40

A pharmaceutical composition comprising the compound of any one of Embodiments P1 to P17; a topoisomerase inhibitor; and a pharmaceutically acceptable carrier.

Embodiment P41

A method of treating Fanconi anemia in a patient in need thereof comprising administering to the patient a therapeutically effective amount of the compound of any one of Embodiments P1-P17.

Embodiment P42

A method of treating Fanconi anemia in a patient in need thereof comprising administering to the patient a therapeutically effective amount of the composition of Embodiment P18.

VI. Additional Embodiments

Embodiment 1

A compound or a pharmaceutically acceptable salt thereof, wherein the compound has formula (I) or formula (II):

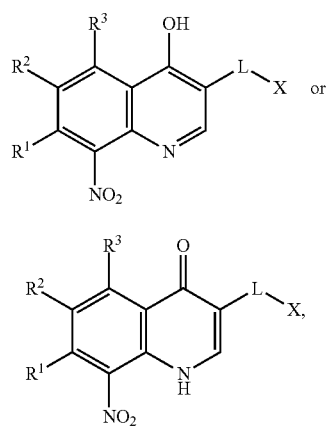

wherein
$R^1$, $R^2$, and $R^3$ are each independently hydrogen, halogen, —$N_3$, —NHC═(O)NHNH$_2$, —CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)$_n$R$^{13}$, —S(O)$_n$NR$^9$R$^{10}$, —NR$^{12}$S(O)$_n$R$^{13}$, —NO$_2$, —OR$^{14}$, —SR$^{14}$, —NR$^{15}$, —OCOR$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

L is a bond, —C(O)—NH—, —NH—C(O)—, —C(O)—, —C(O)—O—, —NH—, —O—, —S—, —S(O)—, —S(O)$_2$—, —NH—S(O)—, —NH—S(O)$_2$—, —CH$_2$N(C(O)OH)—, —CH$_2$—N(CH(O))—, —CH$_2$—N(SO$_2$)—, —CH$_2$NH—, —CH$_2$C(O)NH—, —CH$_2$NHC(O)—, —CH$_2$NHS(O)—, —CH$_2$NHS(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

X is hydrogen, halogen, —$N_3$, —NHC═(O)NHNH$_2$, —CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)$_n$R$^{13}$, —S(O)$_n$NR$^9$R$^{10}$, —NR$^{12}$S(O)R$^{13}$, —NO$_2$, —OR$^{14}$, —SR$^{14}$, —NR$^{15}$, —OCOR$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$, $R^{10}$ $R^{11}$, $R^{12}$, $R^{13}$, $R^{14}$, $R^{15}$, and $R^{16}$, are independently hydrogen, halogen, —CN, —CF$_3$, —CCl$_3$, —CBr$_3$, —CI$_3$, —OH, —NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n is 1 to 4;
wherein the compound of formula (I) is not:

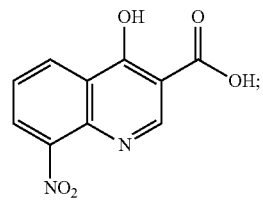 [SMILES: O=C(O)c1cnc2c([N+](=O)[O-])cccc2c1O]

and
wherein the compound of formula (II) is not:

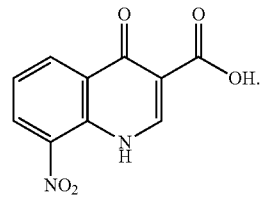 [SMILES: O=C(O)c1c[nH]c2c([N+](=O)[O-])cccc2c1=O]

Embodiment 2

The compound of Embodiment 1, wherein L is —C(O)—NH—, —NH—C(O)—, —C(O)—, —C(O)—O—, —NH—, —O—, —S—, —S(O)—, —S(O)$_2$—, —NH—S(O)—, —NH—S(O)$_2$—, —CH$_2$N(C(O)OH)—, —CH$_2$—N(CH(O))—, —CH$_2$—N(SO$_2$)—, —CH$_2$NH—, —CH$_2$C(O)NH—, —CH$_2$NHC(O)—, —CH$_2$NHS(O)—, —CH$_2$NHS $(O)_2$—, unsubstituted $C_1$-$C_6$ alkylene, unsubstituted $C_1$-$C_6$ heteroalkylene, unsubstituted 5-6 membered cycloalkylene, 5-6 membered unsubstituted heterocycloalkylene, 5-6 membered unsubstituted arylene, or 5-6 membered or unsubstituted heteroarylene.

Embodiment 3

The compound of Embodiment 1, wherein L is —C(O)—NH—, —NH—C(O)—, —NH—, —O—, —S—, —S(O)—, —S(O)$_2$—, —NH—S(O)—, —NH—S(O)$_2$—, —CH$_2$N(C(O)OH)—, —CH$_2$—N(CH(O))—, —CH$_2$—N(SO$_2$)—, —CH$_2$NH—, —CH$_2$C(O)NH—, —CH$_2$NHC(O)—, —CH$_2$NHS(O)—, —CH$_2$NHS(O)$_2$—, unsubstituted $C_1$-$C_6$ alkylene, unsubstituted $C_1$-$C_6$ heteroalkylene, unsubstituted 5-6 membered cycloalkylene, 5-6 membered unsubstituted heterocycloalkylene, 5-6 membered unsubstituted arylene, or 5-6 membered or unsubstituted heteroarylene.

Embodiment 4

The compound of Embodiment 1, wherein L is —C(O)—NH—, —C(O)—, —C(O)—O—, —NH—, —O—, —S—, —S(O)—, or —S(O)$_2$—. The compound of Embodiment 1, wherein L is —C(O)—NH—, —NH—, —O—, —S—, —S(O)—, or —S(O)$_2$—.

Embodiment 5

The compound of Embodiment 1, wherein L is —C(O)—NH— or —C(O)—O—.

Embodiment 6

The compound of Embodiment 1, wherein L is —C(O)—NH—.

Embodiment 7

The compound of Embodiment 1, wherein $R^1$, $R^2$, and $R^3$ are each independently hydrogen, halogen, —NH$_2$, —OH, —NO$_2$, —C(O)CH$_3$, —NHC(O)CH$_3$, —OC(O)CH$_3$, or unsubstituted $C_{1-4}$ alkyl.

Embodiment 8

The compound of Embodiment 1, wherein $R^1$, $R^2$, and $R^3$ are hydrogen.

Embodiment 9

The compound of Embodiment 1, wherein $R^1$, $R^2$, and $R^3$ are hydrogen, and L is —C(O)NH—.

Embodiment 10

The compound of any one of Embodiments 1 to 7, wherein X is hydrogen, halogen, —N$_3$, —NHC=(O)NHNH$_2$, —CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)R$^{13}$, —S(O)NR$^9$R$^{10}$, —NR$^{12}$S(O)$_n$R$^{13}$, —NO$_2$, —OR$^{14}$, —SR$^{14}$, NR$^{15}$, or —OCOR$^{16}$.

Embodiment 11

The compound of any one of Embodiments 1 to 7, wherein X is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 12

The compound of any one of Embodiments 1 to 7, wherein X is $R^{2a}$-substituted or unsubstituted $C_1$-$C_8$ alkyl, $R^{2a}$-substituted or unsubstituted 2-8 membered heteroalkyl, $R^{2a}$-substituted or unsubstituted $C_3$-$C_8$ cycloalkyl, $R^{2a}$-substituted or unsubstituted 3-6 membered heterocycloalkyl, $R^{2a}$-substituted or unsubstituted phenyl, or $R^{2a}$-substituted or unsubstituted 5 or 6 membered heteroaryl;

$R^{2a}$ is independently hydrogen, halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_3$H, —SO$_4$H, —SO$_2$NH$_2$, —NHNH$_2$, —ONH$_2$, —NHC(O)NHNH$_2$, $R^{2b}$-substituted or unsubstituted $C_1$-$C_8$ alkyl, $R^{2b}$-substituted or unsubstituted 2-8 membered heteroalkyl, $R^{2b}$-substituted or unsubstituted $C_3$-$C_8$ cycloalkyl, $R^{2b}$-substituted or unsubstituted 3-6 membered heterocycloalkyl, $R^{2b}$-substituted or unsubstituted phenyl, or $R^{2b}$-substituted or unsubstituted 5 or 6 membered heteroaryl; and $R^{2b}$ is independently hydrogen, halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_3$H, —SO$_4$H, —SO$_2$NH$_2$, —NHNH$_2$, —ONH$_2$, —NHC(O)NHNH$_2$, unsubstituted $C_1$-$C_8$ alkyl, unsubstituted 2-8 membered heteroalkyl, unsubstituted $C_3$-$C_8$ cycloalkyl, unsubstituted 3-6 membered heterocycloalkyl, unsubstituted phenyl, or unsubstituted 5 or 6 membered heteroaryl.

Embodiment 13

The compound of any one of Embodiments 1 to 7, wherein X is unsubstituted $C_1$-$C_8$ alkyl, unsubstituted 2-8 membered heteroalkyl, unsubstituted $C_3$-$C_8$ cycloalkyl, unsubstituted 3-6 membered heterocycloalkyl, unsubstituted phenyl, or unsubstituted 5 or 6 membered heteroaryl.

Embodiment 14

The compound of any one of Embodiments 1 to 7, wherein X is substituted $C_1$-$C_8$ alkyl, substituted 2-8 membered heteroalkyl, substituted $C_3$-$C_8$ cycloalkyl, substituted 3-6 membered heterocycloalkyl, substituted phenyl, or substituted 5 or 6 membered heteroaryl.

Embodiment 15

The compound of embodiment 1, having the formula:

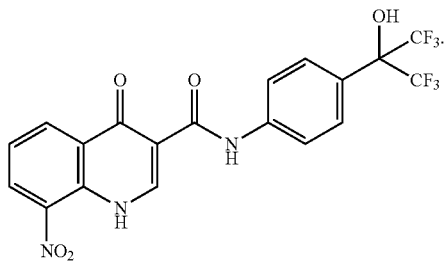 [SMILES: O=C(Nc1ccc(C(O)(C(F)(F)F)C(F)(F)F)cc1)c1c[nH]c2c([N+](=O)[O-])cccc2c1=O]

Embodiment 16

The compound of embodiment 1, having the formula:

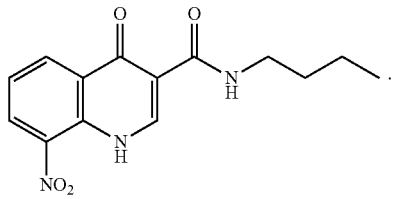 [SMILES: CCCCNC(=O)c1c[nH]c2c([N+](=O)[O-])cccc2c1=O]

Embodiment 17

The compound of embodiment 1, having the formula:

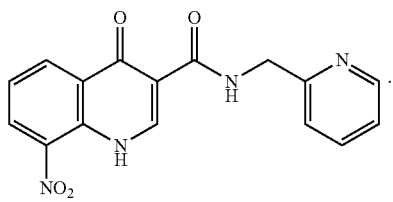 [SMILES: O=C(NCc1ccccn1)c1c[nH]c2c([N+](=O)[O-])cccc2c1=O]

Embodiment 18

A pharmaceutical composition comprising a pharmaceutically acceptable carrier and a compound or a pharmaceutically acceptable salt thereof, wherein the compound has formula (I) or formula (II):

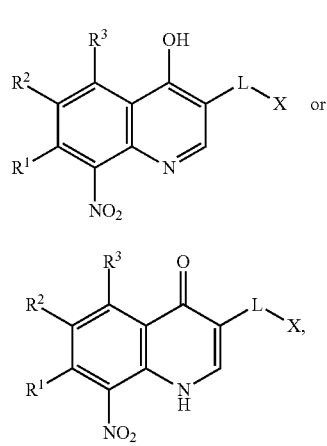

wherein $R^1$, $R^2$, and $R^3$ are each independently hydrogen, halogen, —$N_3$, —NHC═(O)NHNH$_2$, —CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)$_n$R$^{13}$, —S(O)$_n$NR$^9$R$^{10}$, —NR$^{12}$S(O)$_n$R$^{13}$, —NO$_2$, —OR$^{14}$, —SR$^{14}$, —NR$^{15}$, —OCOR$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

L is a bond, —C(O)—NH—, —NH—C(O)—, —C(O)—, —C(O)—O—, —NH—, —O—, —S—, —S(O)—, —S(O)$_2$—, —NH—S(O)—, —NH—S(O)$_2$—, —CH$_2$N(C(O)OH)—, —CH$_2$—N(CH(O))—, —CH$_2$—N(SO$_2$)—, —CH$_2$NH—, —CH$_2$C(O)NH—, —CH$_2$NHC(O)—, —CH$_2$NHS(O)—, —CH$_2$NHS(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

X is hydrogen, halogen, —$N_3$, —NHC═(O)NHNH$_2$, —CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)$_n$R$^{13}$, —S(O)$_n$NR$^9$R$^{10}$, —NR$^{12}$S(O)$_n$R$^{13}$, —NO$_2$, —OR$^{14}$, —SR$^{14}$, —NR$^{15}$, —OCOR$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$, $R^{10}$, $R^{11}$, $R^{12}$, $R^{13}$, $R^{14}$, $R^{15}$, and $R^{16}$, are independently hydrogen, halogen, —CN, —CF$_3$, —CCl$_3$, —CBr$_3$, —CI$_3$, —OH, —NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n is 1 to 4.

Embodiment 19

A method of treating cancer in a patient in need thereof comprising administering to the patient a therapeutically effective amount of a compound or a pharmaceutically acceptable salt thereof, wherein the compound has formula (I) or formula (II):

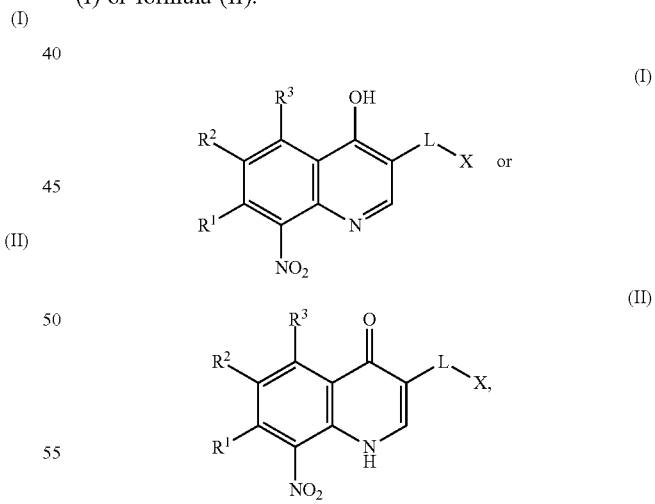

wherein $R^1$, $R^2$, and $R^3$ are each independently hydrogen, halogen, —$N_3$, —NHC═(O)NHNH$_2$, —CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)$_n$R$^{13}$, —S(O)$_n$NR$^9$R$^{10}$, —NR$^{12}$S(O)$_n$R$^{13}$, —NO$_2$, —OR$^{14}$, —SR$^{14}$, —NR$^{15}$, —OCOR$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

L is a bond, —C(O)—NH—, —NH—C(O)—, —C(O)—, —C(O)—O—, —NH—, —O—, —S—, —S(O)—, —S(O)$_2$—, —NH—S(O)—, —NH—S(O)$_2$—, —CH$_2$N(C(O)OH)—, —CH$_2$—N(CH(O))—, —CH$_2$—N(SO$_2$)—, —CH$_2$NH—, —CH$_2$C(O)NH—, —CH$_2$NHC(O)—, —CH$_2$NHS(O)—, —CH$_2$NHS(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

X is hydrogen, halogen, —N$_3$, —NHC=(O)NHNH$_2$, —CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)$_n$ R$^{13}$, —S(O)$_n$NR$^9$R$^{10}$, —NR$^{12}$S(O)$_n$R$^{13}$, —NO$_2$, —OR$^{14}$, —SR$^{14}$, —NR$^{15}$, —OCOR$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^9$, R$^{10}$, R$^{11}$, R$^{12}$, R$^{13}$, R$^{14}$, R$^{15}$, and R$^{16}$, are independently hydrogen, halogen, —CN, —CF$_3$, —CCl$_3$, —CBr$_3$, —CI$_3$, —OH, —NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n is 1 to 4.

Embodiment 20

The method of Embodiment 19, wherein the cancer is breast cancer, colon cancer, prostate cancer, lung cancer, or ovarian cancer.

Embodiment 21

A method of treating cancer in a patient in need thereof comprising administering to the patient a therapeutically effective amount of a pharmaceutical composition of Embodiment 20 to treat the cancer in the patient.

Embodiment 22

The method of Embodiment 23, wherein the cancer is breast cancer, colon cancer, prostate cancer, lung cancer, or ovarian cancer.

Embodiment 23

A method of treating cancer in a patient in need thereof comprising: (i) administering to the patient a therapeutically effective amount of a compound or a pharmaceutically acceptable salt thereof, wherein the compound has formula (I) or formula (II):

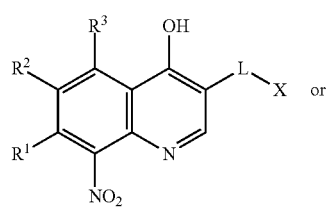

or

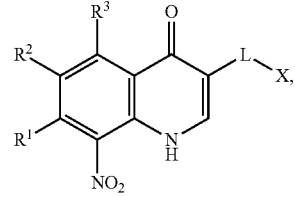

wherein

R$^1$, R$^2$, and R$^3$ are each independently hydrogen, halogen, —N$_3$, —NHC=(O)NHNH$_2$, —CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)$_n$R$^{13}$, —S(O)$_n$NR$^9$R$^{10}$, —NR$^{12}$S(O)$_n$R$^{13}$, —NO$_2$, —OR$^{14}$, —SR$^{14}$, —NR$^{15}$, —OCOR$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

L is a bond, —C(O)—NH—, —NH—C(O)—, —C(O)—, —C(O)—O—, —NH—, —O—, —S—, —S(O)—, —S(O)$_2$—, —NH—S(O)—, —NH—S(O)$_2$—, —CH$_2$N(C(O)OH)—, —CH$_2$—N(CH(O))—, —CH$_2$—N(SO$_2$)—, —CH$_2$NH—, —CH$_2$C(O)NH—, —CH$_2$NHC(O)—, —CH$_2$NHS(O)—, —CH$_2$NHS(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

X is hydrogen, halogen, —N$_3$, —NHC=(O)NHNH$_2$, —CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)$_n$ R$^{13}$, —S(O)$_n$NR$^9$R$^{10}$, —NR$^{12}$S(O)$_n$R$^{13}$, —NO$_2$, —OR$^{14}$, —SR$^{14}$, —NR$^{15}$, —OCOR$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^9$, R$^{10}$, R$^{11}$, R$^{12}$, R$^{13}$, R$^{14}$, R$^{15}$, and R$^{16}$, are independently hydrogen, halogen, —CN, —CF$_3$, —CCl$_3$, —CBr$_3$, —CI$_3$, —OH, —NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n is 1 to 4, and (ii) a chemotherapeutic agent, radiation, or a combination thereof, to treat the cancer in the patient.

Embodiment 24

The method of Embodiment 25, wherein the cancer is breast cancer, colon cancer, prostate cancer, lung cancer, or ovarian cancer.

Embodiment 25

The method of Embodiment 25, wherein the chemotherapeutic agent is a PARP inhibitor.

Embodiment 26

The method of Embodiment 25, wherein the chemotherapeutic agent is a topoisomerase inhibitor.

Embodiment 27

The method of Embodiment 28, wherein the topoisomerase inhibitor is a topoisomerase I inhibitor.

Embodiment 28

The method of Embodiment 25, wherein (i) is administered prior to (ii).

Embodiment 29

The method of Embodiment 25, wherein (i) and (ii) are administered concurrently.

Embodiment 30

A method of sensitizing cancer cells to radiation therapy or chemotherapy comprising administering a compound or a pharmaceutically acceptable salt thereof, wherein the compound has formula (I) or formula (II):

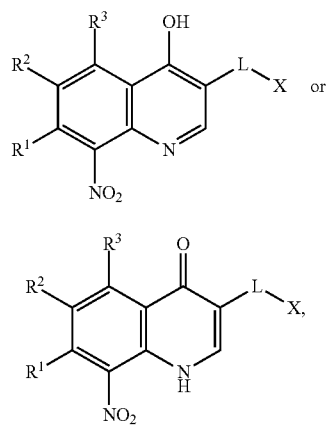

wherein
$R^1$, $R^2$, and $R^3$ are each independently hydrogen, halogen, —$N_3$, —NHC═(O)NHNH$_2$, —CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)$_n$R$^{13}$, —S(O)$_n$NR$^9$R$^{10}$, —NR$^{12}$S(O)$_n$R$^{13}$, —NO$_2$, —OR$^{14}$, —SR$^{14}$, —NR$^{15}$, —OCOR$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
L is a bond, —C(O)—NH—, —NH—C(O)—, —C(O)—, —C(O)—O—, —NH—, —O—, —S—, —S(O)—, —S(O)$_2$—, —NH—S(O)—, —NH—S(O)$_2$—, —CH$_2$N(C(O)OH)—, —CH$_2$—N(CH(O))—, —CH$_2$—N(SO$_2$)—, —CH$_2$NH—, —CH$_2$C(O)NH—, —CH$_2$NHC(O)—, —CH$_2$NHS(O)—, —CH$_2$NHS(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
X is hydrogen, halogen, —N$_3$, —NHC═(O)NHNH$_2$, —CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)$_n$R$^{13}$, —S(O)$_n$NR$^9$R$^{10}$, —NR$^{12}$S(O)$_n$R$^{13}$, —NO$_2$, —OR$^{14}$, —SR$^{14}$, —NR$^{15}$, —OCOR$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^9$, $R^{10}$, $R^{11}$, $R^{12}$, $R^{13}$, $R^{14}$, $R^{15}$, and $R^{16}$, are independently hydrogen, halogen, —CN, —CF$_3$, —CCl$_3$, —CBr$_3$, —CI$_3$, —OH, —NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
and n is 1 to 4.

Embodiment 31

A method of potentiating the clinical efficacy of a PARP inhibitor comprising administering a compound or a pharmaceutically acceptable salt thereof, wherein the compound has formula (I) or formula (II):

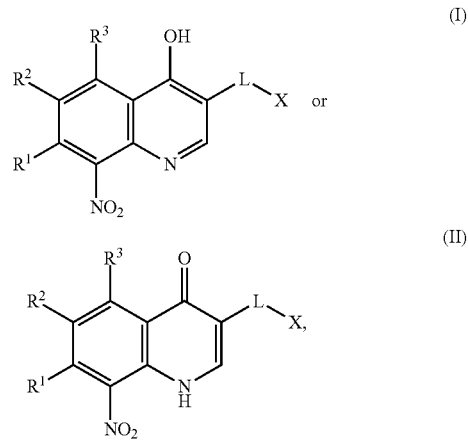

wherein
$R^1$, $R^2$, and $R^3$ are each independently hydrogen, halogen, —N$_3$, —NHC═(O)NHNH$_2$, —CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)R$^{13}$, —S(O)$_1$NR$^9$R$^{10}$, —NR$^{12}$S(O)R$^{13}$, —NO$_2$, —OR$^{14}$, —SR$^{14}$, —NR$^{15}$, —OCOR$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
L is a bond, —C(O)—NH—, —NH—C(O)—, —C(O)—, —C(O)—O—, —NH—, —O—, —S—, —S(O)—, —S(O)$_2$—, —NH—S(O)—, —NH—S(O)$_2$—, —CH$_2$N(C(O)OH)—, —CH$_2$—N(CH(O))—, —CH$_2$—N(SO$_2$)—, —CH$_2$NH—, —CH$_2$C(O)NH—, —CH$_2$NHC(O)—, —CH$_2$NHS(O)—, —CH$_2$NHS(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

X is hydrogen, halogen, $-N_3$, $-NHC=(O)NHNH_2$, $-CN$, $-CF_3$, $-CCl_3$, $-CBr_3$, $-CI_3$, $-NR^9R^{10}$, $-C(O)R^{11}$, $-C(O)NR^9R^{10}$, $-NR^{12}C(O)R^{11}$, $-S(O)_nR^{13}$, $-S(O)_nNR^9R^{10}$, $-NR^{12}S(O)_nR^{13}$, $-NO_2$, $-OR^{14}$, $-SR^{14}$, $-NR^{15}$, $-OCOR^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$, $R^{10}$ $R^{11}$, $R^{12}$, $R^{13}$, $R^{14}$, $R^{15}$, and $R^{16}$, are independently hydrogen, halogen, $-CN$, $-CF_3$, $-CCl_3$, $-CBr_3$, $-CI_3$, $-OH$, $-NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n is 1 to 4.

Embodiment 32

A method of potentiating the clinical efficacy of a topoisomerase inhibitor comprising administering a compound or a pharmaceutically acceptable salt thereof, wherein the compound has formula (I) or formula (II):

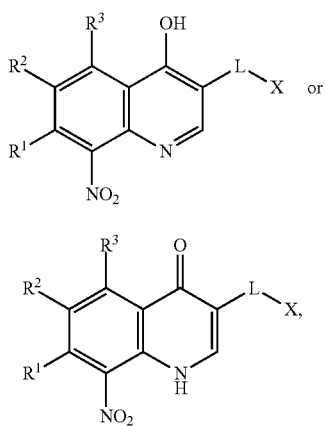

wherein
$R^1$, $R^2$, and $R^3$ are each independently hydrogen, halogen, $-N_3$, $-NHC=(O)NHNH_2$, $-CN$, $-CF_3$, $-CCl_3$, $-CBr_3$, $-CI_3$, $-NR^9R^{10}$, $-C(O)R^{11}$, $-C(O)NR^9R^{10}$, $-NR^{12}C(O)R^{11}$, $-S(O)_nR^{13}$, $-S(O)_nNR^9R^{10}$, $-NR^{12}S(O)_nR^{13}$, $-NO_2$, $-OR^{14}$, $-SR^{14}$, $-NR^{15}$, $-OCOR^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

L is a bond, $-C(O)-NH-$, $-NH-C(O)-$, $-C(O)-$, $-C(O)-O-$, $-NH-$, $-O-$, $-S-$, $-S(O)-$, $-S(O)_2-$, $-NH-S(O)-$, $-NH-S(O)_2-$, $-CH_2N(C(O)OH)-$, $-CH_2-N(CH(O))-$, $-CH_2-N(SO_2)-$, $-CH_2NH-$, $-CH_2C(O)NH-$, $-CH_2NHC(O)-$, $-CH_2NHS(O)-$, $-CH_2NHS(O)_2-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

X is hydrogen, halogen, $-N_3$, $-NHC=(O)NHNH_2$, $-CN$, $-CF_3$, $-CCl_3$, $-CBr_3$, $-CI_3$, $-NR^9R^{10}$, $-C(O)R^{11}$, $-C(O)NR^9R^{10}$, $-NR^{12}C(O)R^{11}$, $-S(O)_nR^{13}$, $-S(O)_nNR^9R^{10}$, $-NR^{12}S(O)_nR^{13}$, $-NO_2$, $-OR^{14}$, $-SR^{14}$, $-NR^{15}$, $-OCOR^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$, $R^{10}$ $R^{11}$, $R^{12}$, $R^{13}$, $R^{14}$, $R^{15}$, and $R^{16}$, are independently hydrogen, halogen, $-CN$, $-CF_3$, $-CCl_3$, $-CBr_3$, $-CI_3$, $-OH$, $-NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and
n is 1 to 4.

Embodiment 33

The method of Embodiment 34, wherein the topoisomerase inhibitor is a topoisomerase I inhibitor.

Embodiment 34

A method of inhibiting DNA replication in cells comprising administering a compound or a pharmaceutically acceptable salt thereof, wherein the compound has formula (I) or formula (II):

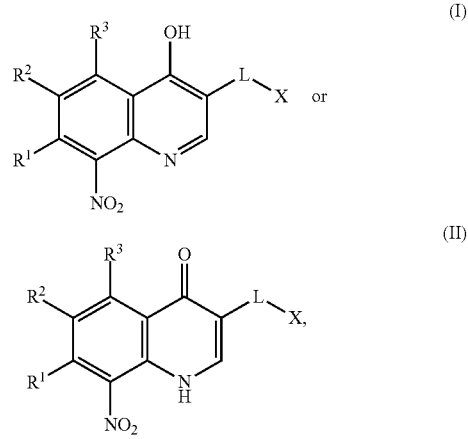

wherein
$R^1$, $R^2$, and $R^3$ are each independently hydrogen, halogen, $-N_3$, $-NHC=(O)NHNH_2$, $-CN$, $-CF_3$, $-CCl_3$, $-CBr_3$, $-CI_3$, $-NR^9R^{10}$, $-C(O)R^{11}$, $-C(O)NR^9R^{10}$, $-NR^{12}C(O)R^{11}$, $-S(O)_nR^{13}$, $-S(O)_nNR^9R^{10}$, $-NR^{12}S(O)R^{13}$, $-NO_2$, $-OR^{14}$, $-SR^{14}$, $-NR^{15}$, $-OCOR^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

L is a bond, $-C(O)-NH-$, $-NH-C(O)-$, $-C(O)-$, $-C(O)-O-$, $-NH-$, $-O-$, $-S-$, $-S(O)-$, $-S(O)_2-$, $-NH-S(O)-$, $-NH-S(O)_2-$, —CH$_2$N(C(O)OH)—, —CH$_2$—N(CH(O))—, —CH$_2$—N(SO$_2$)—, —CH$_2$NH—, —CH$_2$C(O)NH—, —CH$_2$NHC(O)—, —CH$_2$NHS(O)—, —CH$_2$NHS(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

X is hydrogen, halogen, —N$_3$, —NHC=(O)NHNH$_2$, —CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)$_n$R$^{13}$, —S(O)$_n$NR$^9$R$^{10}$, —NR$^{12}$S(O)$_n$R$^{13}$, —NO$_2$, —OR$^{14}$, —SR$^{14}$, —NR$^{15}$, —OCOR$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^9$, R$^{10}$ R$^{11}$, R$^{12}$, R$^{13}$, R$^{14}$, R$^{15}$, and R$^{16}$, are independently hydrogen, halogen, —CN, —CF$_3$, —CCl$_3$, —CBr$_3$, —CI$_3$, —OH, —NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n is 1 to 4.

Embodiment 35

A method of inhibiting DNA replication in a patient in need thereof comprising administering a compound or a pharmaceutically acceptable salt thereof, wherein the compound has formula (I) or formula (II):

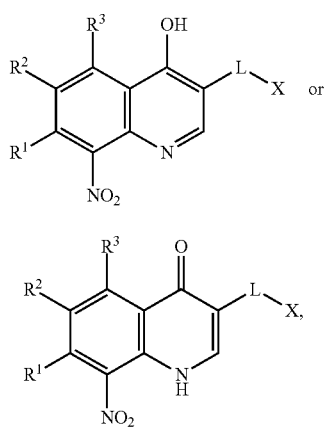

wherein
R$^1$, R$^2$, and R$^3$ are each independently hydrogen, halogen, —N$_3$, —NHC=(O)NHNH$_2$, —CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)$_n$R$^{13}$, —S(O)$_n$NR$^9$R$^{10}$, —NR$^{12}$S(O)$_n$R$^{13}$, —NO$_2$, —OR$^{14}$, —SR$^{14}$, —NR$^{15}$, —OCOR$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
L is a bond, —C(O)—NH—, —NH—C(O)—, —C(O)—, —C(O)—O—, —NH—, —O—, —S—, —S(O)—, —S(O)$_2$—, —NH—S(O)—, —NH—S(O)$_2$—, —CH$_2$N(C(O)OH)—, —CH$_2$—N(CH(O))—, —CH$_2$—N(SO$_2$)—, —CH$_2$NH—, —CH$_2$C(O)NH—, —CH$_2$NHC(O)—, —CH$_2$NHS(O)—, —CH$_2$NHS(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

X is hydrogen, halogen, —N$_3$, —NHC=(O)NHNH$_2$, —CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)$_n$R$^{13}$, —S(O)$_n$NR$^9$R$^{10}$, —NR$^{12}$S(O)$_n$R$^{13}$, —NO$_2$, —OR$^{14}$, —SR$^{14}$, —NR$^{15}$, —OCOR$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^9$, R$^{10}$ R$^{11}$, R$^{12}$, R$^{13}$, R$^{14}$, R$^{15}$, and R$^{16}$, are independently hydrogen, halogen, —CN, —CF$_3$, —CCl$_3$, —CBr$_3$, —CI$_3$, —OH, —NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n is 1 to 4.

Embodiment 36

A method of suppressing DNA double-strand break repair end resection, recombination, over-resection of nascent DNA in cells defective in fork protection, and restart of stalled DNA replication forks in cells or a patient in need thereof comprising administering a compound or a pharmaceutically acceptable salt thereof, wherein the compound has formula (I) or formula (II):

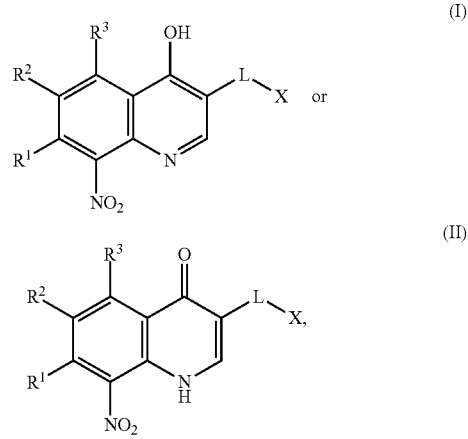

wherein
R$^1$, R$^2$, and R$^3$ are each independently hydrogen, halogen, —N$_3$, —NHC=(O)NHNH$_2$, —CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)$_n$R$^{13}$, —S(O)$_n$NR$^9$R$^{10}$, —NR$^{12}$S(O)$_n$R$^{13}$, —NO$_2$, —OR$^{14}$, —SR$^{14}$, —NR$^{15}$, —OCOR$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

L is a bond, —C(O)—NH—, —NH—C(O)—, —C(O)—, —C(O)—O—, —NH—, —O—, —S—, —S(O)—, —S(O)$_2$—, —NH—S(O)—, —NH—S(O)$_2$—, —CH$_2$N(C(O)OH)—, —CH$_2$—N(CH(O))—, —CH$_2$—N(SO$_2$)—, —CH$_2$NH—, —CH$_2$C(O)NH—, —CH$_2$NHC(O)—, —CH$_2$NHS(O)—, —CH$_2$NHS(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

X is hydrogen, halogen, —N$_3$, —NHC=(O)NHNH$_2$, —CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)$_n$R$^{13}$, —S(O)$_n$NR$^9$R$^{10}$, —NR$^{12}$S(O)R$^{13}$, —NO$_2$, —OR$^{14}$, —SR$^{14}$, —NR$^{15}$, —OCOR$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^9$, R$^{10}$, R$^{11}$, R$^{12}$, R$^{13}$, R$^{14}$, R$^{15}$, and R$^{16}$, are independently hydrogen, halogen, —CN, —CF$_3$, —CCl$_3$, —CBr$_3$, —CI$_3$, —OH, —NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n is 1 to 4.

Embodiment 37

The method of Embodiment 38, further comprising administering a chemotherapeutic agent, radiation, or a combination thereof.

Embodiment 38

A pharmaceutical composition comprising a chemotherapeutic agent; a pharmaceutically acceptable carrier; and a compound or a pharmaceutically acceptable salt thereof, wherein the compound has formula (I) or formula (II):

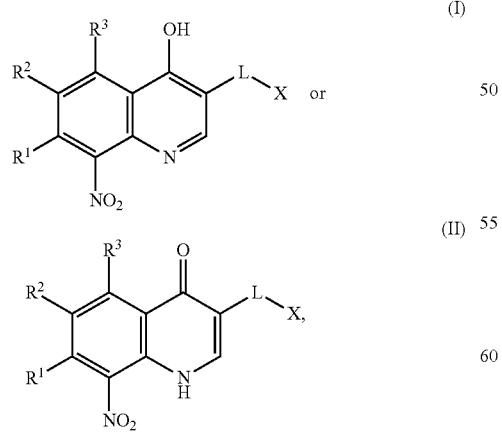

wherein
R$^1$, R$^2$, and R$^3$ are each independently hydrogen, halogen, —N$_3$, —NHC=(O)NHNH$_2$, —CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)$_n$R$^{13}$, —S(O)$_n$NR$^9$R$^{10}$, —NR$^{12}$S(O)$_n$R$^{13}$, —NO$_2$, —OR$^{14}$, —SR$^{14}$, —NR$^{15}$, —OCOR$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

L is a bond, —C(O)—NH—, —NH—C(O)—, —C(O)—, —C(O)—O—, —NH—, —O—, —S—, —S(O)—, —S(O)$_2$—, —NH—S(O)—, —NH—S(O)$_2$—, —CH$_2$N(C(O)OH)—, —CH$_2$—N(CH(O))—, —CH$_2$—N(SO$_2$)—, —CH$_2$NH—, —CH$_2$C(O)NH—, —CH$_2$NHC(O)—, —CH$_2$NHS(O)—, —CH$_2$NHS(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

X is hydrogen, halogen, —N$_3$, —NHC=(O)NHNH$_2$, —CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)$_n$R$^{13}$, —S(O)$_n$NR$^9$R$^{10}$, —NR$^{12}$S(O)$_n$R$^{13}$, —NO$_2$, —OR$^{14}$, —SR$^{14}$, —NR$^{15}$, —OCOR$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^9$, R$^{10}$, R$^{11}$, R$^{12}$, R$^{13}$, R$^{14}$, R$^{15}$, and R$^{16}$, are independently hydrogen, halogen, —CN, —CF$_3$, —CCl$_3$, —CBr$_3$, —CI$_3$, —OH, —NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n is 1 to 4.

Embodiment 39

A pharmaceutical composition comprising a PARP inhibitor; a pharmaceutically acceptable carrier; and a compound or a pharmaceutically acceptable salt thereof, wherein the compound has formula (I) or formula (II):

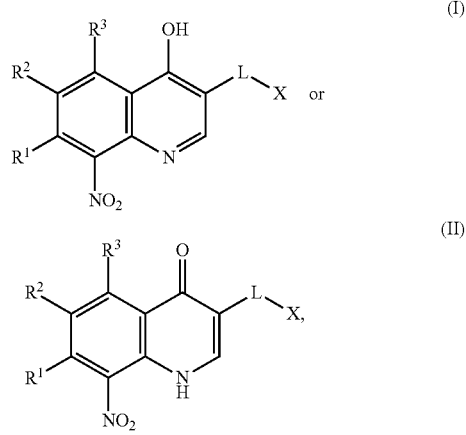

wherein
R$^1$, R$^2$, and R$^3$ are each independently hydrogen, halogen, —N$_3$, —NHC=(O)NHNH$_2$, —CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)$_n$R$^{13}$, —S(O)$_n$NR$^9$R$^{10}$, —NR$^{12}$S(O)$_n$R$^{13}$, —NO$_2$, —OR$^{14}$, —SR$^{14}$, —NR$^{15}$, —OCOR$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

L is a bond, —C(O)—NH—, —NH—C(O)—, —C(O)—, —C(O)—O—, —NH—, —O—, —S—, —S(O)—, —S(O)$_2$—, —NH—S(O)—, —NH—S(O)$_2$—, —CH$_2$N(C(O)OH)—, —CH$_2$—N(CH(O))—, —CH$_2$—N(SO$_2$)—, —CH$_2$NH—, —CH$_2$C(O)NH—, —CH$_2$NHC(O)—, —CH$_2$NHS(O)—, —CH$_2$NHS(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

X is hydrogen, halogen, —N$_3$, —NHC═(O)NHNH$_2$, —CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)$_n$ R$^{13}$, —S(O)$_n$NR$^9$R$^{10}$, —NR$^{12}$S(O)$_n$R$^{13}$, —NO$_2$, —OR$^{14}$, —SR$^{14}$, —NR$^{15}$, —OCOR$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^9$, R$^{10}$ R$^{11}$, R$^{12}$, R$^{13}$, R$^{14}$, R$^{15}$, and R$^{16}$, are independently hydrogen, halogen, —CN, —CF$_3$, —CCl$_3$, —CBr$_3$, —CI$_3$, —OH, —NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n is 1 to 4.

Embodiment 40

A pharmaceutical composition comprising a topoisomerase inhibitor; a pharmaceutically acceptable carrier; and a compound or a pharmaceutically acceptable salt thereof, wherein the compound has formula (I) or formula (II):

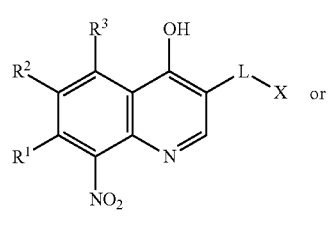

(I)

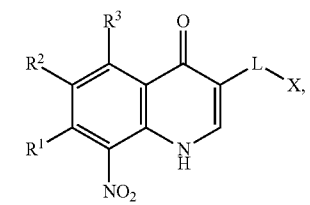

(II)

wherein
R$^1$, R$^2$, and R$^3$ are each independently hydrogen, halogen, —N$_3$, —NHC═(O)NHNH$_2$, —CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)$_n$R$^{13}$, —S(O)$_n$NR$^9$R$^{10}$, —NR$^{12}$S(O)$_n$R$_{13}$, —NO$_2$, —OR$^{14}$, —SR$^{14}$, —NR$^{15}$, —OCOR$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

L is a bond, —C(O)—NH—, —NH—C(O)—, —C(O)—, —C(O)—O—, —NH—, —O—, —S—, —S(O)—, —S(O)$_2$—, —NH—S(O)—, —NH—S(O)$_2$—, —CH$_2$N(C(O)OH)—, —CH$_2$—N(CH(O))—, —CH$_2$—N(SO$_2$)—, —CH$_2$NH—, —CH$_2$C(O)NH—, —CH$_2$NHC(O)—, —CH$_2$NHS(O)—, —CH$_2$NHS(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

X is hydrogen, halogen, —N$_3$, —NHC═(O)NHNH$_2$, —CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)$_n$ R$^{13}$, —S(O)$_n$NR$^9$R$^{10}$, —NR$^{12}$S(O)$_n$R$^{13}$, —NO$_2$, —OR$^{14}$, —SR$^{14}$, —NR$^{15}$, —OCOR$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^9$, R$^{10}$ R$^{11}$, R$^{12}$, R$^{13}$, R$^{14}$, R$^{15}$, and R$^{16}$, are independently hydrogen, halogen, —CN, —CF$_3$, —CCl$_3$, —CBr$_3$, —CI$_3$, —OH, —NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n is 1 to 4.

Embodiment 41

A method of treating Fanconi anemia in a patient in need thereof comprising administering to the patient a therapeutically effective amount of a compound or a pharmaceutically acceptable salt thereof, wherein the compound has formula (I) or formula (II):

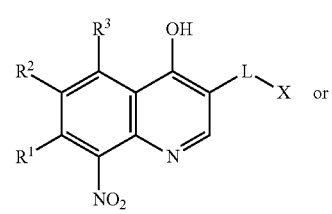

(I)

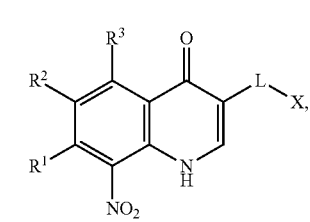

(II)

wherein

R$^1$, R$^2$, and R$^3$ are each independently hydrogen, halogen, —N$_3$, —NHC=(O)NHNH$_2$, —CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)$_n$R$^{13}$, —S(O)$_n$NR$^9$R$^{10}$, —NR$^{12}$S(O)$_n$R$^{13}$, —NO$_2$, —OR$^{14}$, —SR$^{14}$, —NR$^{15}$, —OCOR$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

L is a bond, —C(O)—NH—, —NH—C(O)—, —C(O)—, —C(O)—O—, —NH—, —O—, —S—, —S(O)—, —S(O)$_2$—, —NH—S(O)—, —NH—S(O)$_2$—, —CH$_2$N(C(O)OH)—, —CH$_2$—N(CH(O))—, —CH$_2$—N(SO$_2$)—, —CH$_2$NH—, —CH$_2$C(O)NH—, —CH$_2$NHC(O)—, —CH$_2$NHS(O)—, —CH$_2$NHS(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

X is hydrogen, halogen, —N$_3$, —NHC=(O)NHNH$_2$, —CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)$_n$ R$^{13}$, —S(O)$_n$NR$^9$R$^{10}$, —NR$^{12}$S(O)$_n$R$^{13}$, —NO$_2$, —OR$^{14}$, —SR$^{14}$, —NR$^{15}$, —OCOR$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^9$, R$^{10}$ R$^{11}$, R$^{12}$, R$^{13}$, R$^{14}$, R$^{15}$, and R$^{16}$, are independently hydrogen, halogen, —CN, —CF$_3$, —CCl$_3$, —CBr$_3$, —CI$_3$, —OH, —NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n is 1 to 4.

Embodiment 42

A method of treating Fanconi anemia in a patient in need thereof comprising administering to the patient a therapeutically effective amount of the composition of Embodiment 20.

Embodiment 43

The method of embodiment 41 or 42, wherein the patient has cancer.

EXAMPLES

DNA replication is the central process of all actively dividing cells. Blocking this process can result in cell cycle arrest, senescence, and apoptosis. Therefore, DNA replication forks are the targets of most cancer chemotherapeutics, including agents that induce DNA lesions, such as camptothecin (CPT) and cisplatin, plus those that stall forks, such as gemcitabine and 5-fluorouracil. In addition, radiotherapy (RT), which is used to treat ~50% of all cancers, induces DNA damage. If not repaired, this DNA damage may block or collapse DNA replication forks and kill cancer cells. However, a drawback of these therapies is that the cancer cell may become resistant to the radiation or chemotherapy. Reasons for resistance include increased tolerance for DNA lesions, and enhanced capacity for DNA damage response and repair. It has been shown that that cancer cells that are resistant to RT or chemotherapeutic drugs have abnormally high DNA repair capacity, and inhibition of DNA repair has successfully sensitized the cancer cells to cytotoxicity from chemotherapeutic drugs.

One major conserved DNA repair enzyme is the DNA2 helicase/nuclease (DNA2). Complete inactivation of either the helicase or nuclease activity of DNA2 in cells from a wide range of organisms, including yeast and humans, induces cell cycle arrest and cell death. Disruption of DNA2 has been associated with human disease. A splice-site mutation that causes decreased levels of human DNA2 gives rise to Seckel syndrome, a primordial dwarfism syndrome. Other mutations are linked to breast and gastric cancers. Interestingly, the DNA2-deficient Seckel cells show markers of senescence, where cells are viable but cease to proliferate.

DNA2 plays three key roles that allow the cancer cells to resist the intrinsic and extrinsic DNA replication stresses induced by chemotherapy or RT: flap removal during DNA replication, double-strand break (DSB) resection during repair and telomere replication and recombination, and stabilization and restart of reversed replication forks (Wanrooij and Burgers, 2015). During replication, DNA2 removes the long 5' RNA/DNA "flaps" that arise during Okazaki fragment processing in difficult-to-replicate genomic regions. In yeast, ScDNA2 is probably the major nuclease for RNA primer removal during Okazaki fragment maturation, in collaboration with flap endonuclease 1 (FEN1 or Rad27). For DSB repair, DNA2 acts in one of the two major DSB resection pathways. DNA2 acts with the Bloom Syndrome (BLM) helicase or Wemer Syndrome (WRN) helicase in end resection at a critical early step after licensing by limiting cleavage by the MRN/CtIP complex. BLM (or WRN), moving on the 3' terminated strand, unwinds the duplex end to create a "fork"; DNA2 acts as a nuclease on the complementary strand and degrades the 5' end to produce 3' ssDNA tails for strand invasion during homology-directed repair (HDR), BIR, and S phase checkpoint activation. This resection activity functions in parallel to and independently of resection by exonuclease 1 (EXO1). At stalled replication forks, DNA2 acts to stabilize, repair and restart forks to allow completion of replication. DNA2 also acts in signaling as both an activator and a target of checkpoint kinases. For instance, DNA2 is required to directly activate the yeast master signaling kinase ATR. Furthermore, DNA2 is a target of checkpoint effector kinase Rad53/Chk1/2, and is required to regulate potentially deleterious fork reversal and template switching during replication fork stalling in yeast and humans. DNA2 can also play a negative role when the RAD51, BRCA1, BRCA2 and the FA/BRCA (Fanconi anemia/Breast cancer) pathway is impaired. Like MRE11, which functions upstream of DNA2, DNA2 is involved in the excessive resection seen in cells deficient in fork protection. Thus, DNA2 must be highly regulated to protect genome stability.

Biochemically, DNA2 is well defined, though structure/function studies have been limited by lack of a crystal structure (Pavletich, 2015, eLife). In particular, although it is known that the helicase and nuclease are coordinated, and the nuclease catalytic site and helicase motifs are defined, the DNA binding sites remain elusive. Biochemical and genetic experiments have demonstrated an intricate interaction between the nuclease and helicase (Bae et al., 2001; Budd and Campbell, 2000, 2009; Kao et al., 2004a; Kao et al., 2004b; Levikova et al., 2013). Furthermore, biochemical studies indicate that there is a single maj or DNA binding site interacting at the junction of the flap and downstream duplex DNA that is required for both the nuclease and helicase activities (Stewart et al., 2010). The motifs in the DNA2 protein that govern this maj or binding site remains elusive. Finally, although mutations in the nuclease domain often also affect the helicase activity, no mutations in the helicase domain have been shown to reduce the nuclease activity significantly. Mutational analysis is typically used to study DNA binding, but we report the results of an alternative strategy: the isolation of small molecule inhibitors of DNA2.

Figure 8A:
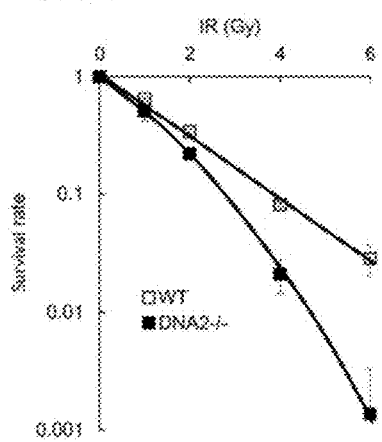
FIGS. 8A-8F.
Figure 8B:
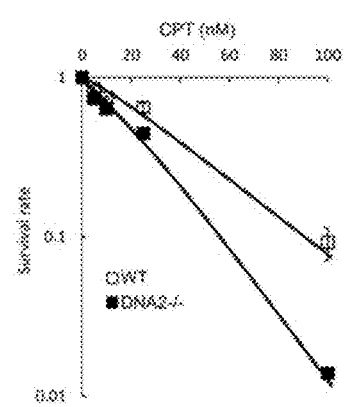
Figure 8C:
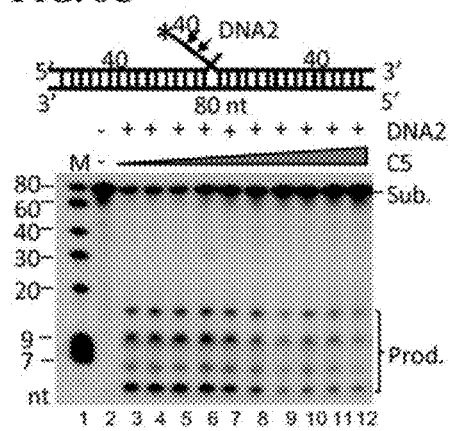
Figure 8D:
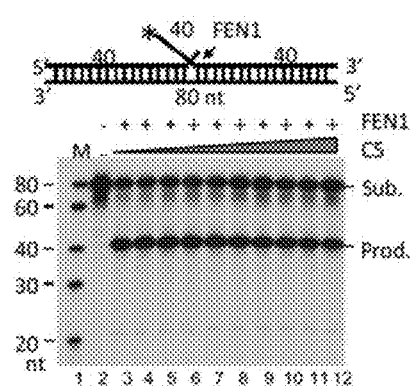
Figure 8E:
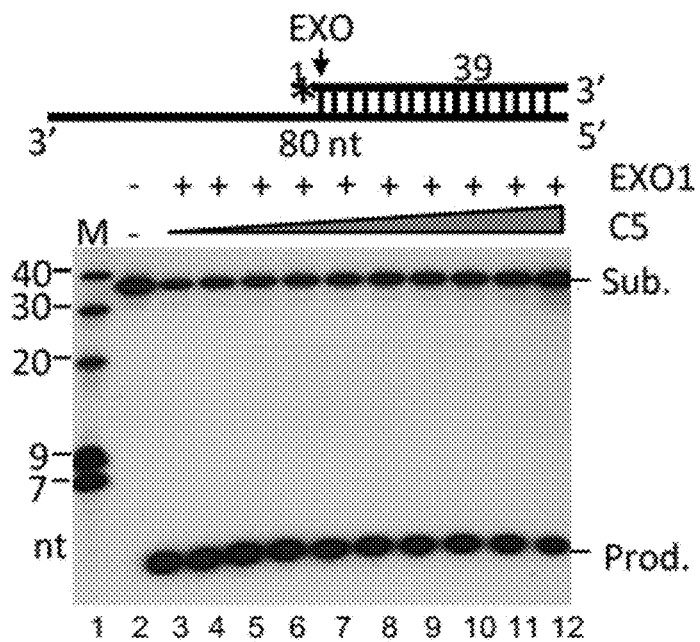
Figure 8F:
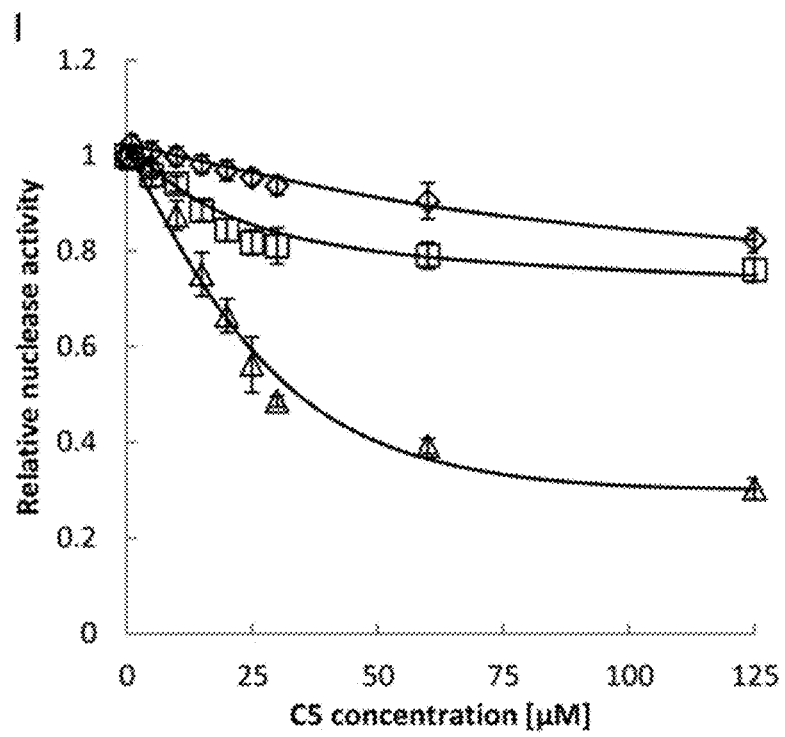

A. Elimination of the DNA2 Gene Sensitizes Cells to Radio- and Chemo-Therapeutic Agents We were interested in DNA2 as a target of inhibition because yeast and human cells that are depleted of DNA2 are sensitive to agents that cause replication stress, such as CPT and cisplatin (Budd & Campbell, 2000; Karanja et al, 2012; Peng et al, 2012). DNA2 is recruited to ionizing-radiation (IR)-induced subnuclear foci in chicken and human cell lines (Hoa et al., 2015). To further investigate the biological roles of DNA2 in mammals, we established DNA2 knockout (dna2$^{-/-}$) mouse ES (MES) cells. The dna2$^{-/-}$ MES cells were viable, presumably due to backup repair pathways, perhaps involving EXO1, as in yeast; although their proliferation rate was approximately 50% of the WT MES cells. To investigate if DNA2 knockout caused the cells to be more sensitive to DNA damaging agents, we treated WT and dna2$^{-/-}$ MES cells with γ-irradiation (IR) and CPT and observed that dna2$^{-/-}$ MES cells were significantly more sensitive than WT cells to both IR and CPT (FIGS. 8A-8B). Taken together with previous work (Duxin, J. P., Dao, B., Martinsson, P., Rajala, N., Guittat, L., Campbell, J. L., Spelbrink, J. N., and Stewart, S. A. (2009). Human Dna2 is a nuclear and mitochondrial DNA maintenance protein. Molecular and cellular biology 29, 4274-4282. Duxin, J. P., Moore, H. R., Sidorova, J., Karanja, K., Honaker, Y., Dao, B., Piwnica-Worms, H., Campbell, J. L., Monnat, R. J., and Stewart, S. A. (2012); Karanja et al., 2012, 1014), these findings suggested that DNA2 is a useful candidate for sensitizing cancer cells to DNA damage-inducing therapeutic agents.

B. Virtual High Throughput Screening and Experimental Validation for Inhibitors of DNA2

Figure 1B:
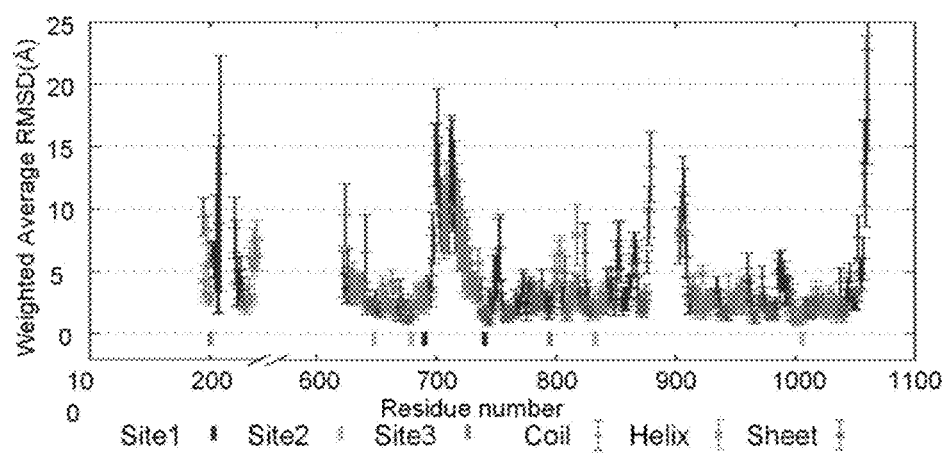
Figure 1C:
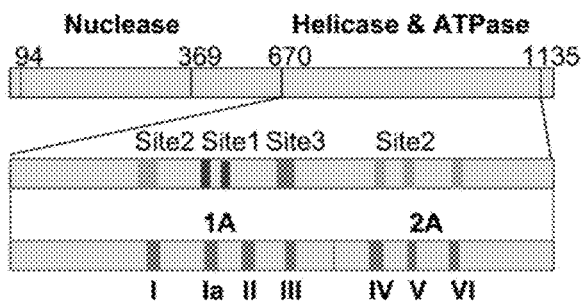

We employed a three-dimensional structural model for virtual screening of small molecules that bind to DNA2. The homology model for the DNA2 helicase domain was based on the crystal structures of the Upf1-RNA U15 complex (PDB 2XZL (Chakrabarti et al., 2011)) and the human Upf1-ADP complex (PDB 2GK6 (Cheng et al., 2007)), which have high sequence identity with DNA2. Although the sequence identity (30%) between DNA2 and Upf1 was at the lower limit for homology modeling, we were able to successfully build the Upf1-based DNA2 model structure (FIG. 1A). After aligning the DNA2 helicase domain with UPF1, the homology model was built with the SWISS-MODEL tool and refined with the Schrodinger Protein Preparation Wizard to fix missing residues and hydrogen positions (FIG. 1A). We predicted druggable sites on the DNA2 model using an in-house-developed Druggable Site Prediction by FDA-approved drugs (DSP) methodology, which uses a diverse subset of 100 FDA-approved drug molecules to dock around the protein surface and predict best binding sites on the protein surface. The definition of the "best binding site" is based on the numbers of the tested drugs bound to the protein pockets. We identified three docking pockets for screening, designated as Sites 1, 2, and 3 with 53%, 24%, and 12% of the tested drugs bound to them, respectively (FIG. 1A). Sites 1 and 3 are predicted to make close contact with DNA and Site 2 is close to the ATP binding and hydrolysis motifs of the helicase domain. The proposed Site 3 is composed of the limited residues conserved between DNA2 and UPF1 in the N-terminal model sequence and interacts with the DNA and Site 1 (FIG. 1A). More importantly, molecular dynamics simulation results further indicated the DNA2 model was stable and reasonable, making it a good choice for in silico screening of DNA2 small molecule inhibitors. Refinement of the structure by molecular dynamics simulation showed that the site centers are stable and that the N-terminal domain stays as shown in FIG. 1B. The average root-mean-square deviation (RMSD) of site centers was only 2-3 Å during simulation, although the RMSD of some flexible loop regions could be more than 15 Å, which indicates that the predicted sites are stabilized to allow ligand binding. Based on an alignment of helicase family members, there are seven highly conserved helicase motifs including I, Ia, II, III, IV, V, and VI in DNA2. The I, II, and IV motifs are for ATP binding and hydrolysis, whereas the Ia, III, and V motifs are the DNA binding domains in other helicases. Domains IV and VI coordinate the DNA unwinding and hydrolysis. One predicted site of drug binding, Site 1, contains amino acids in the Ia motif. Site 2 contains residues in motif I, as well as in motifs V and VI (FIG. 1C). This information allowed us to focus our search for candidate DNA2 inhibitors on the most likely small molecule binding sites. It also guided us to a pocket that might further illuminate how DNA2 interacts with its DNA substrate.

We then conducted a virtual high throughput screening (vHTS) for molecules binding to Site 1 because Site 1 gave the best FDA drug screen score and is predicted to affect DNA binding, making it a favorable target site. Our model also suggested that Site 1, which interacts with Site 3, might be a shared component of both the helicase and nuclease activity and that inhibitors bound to Site 1 might clarify the coordination of the nuclease and helicase activities of DNA2. We used an in-house-developed Multiple-Stage Full-Coverage (MSFC-VS) algorithm to screen an in silico a library of 260,071 compounds from the National Cancer Institute Developmental Therapeutics Program (NCI DTP) library for binding to Site 1. This generated a list of 40 compounds (Table S1).

TABLE 1

Identification of the top 40 hits by virtual screening based on the DNA2 3-D model

| No. | NSC No.* | Formula | MW (Dalton) | Docking Scores** | Nuclease inhibition | DNA-dependent ATPase |
|---|---|---|---|---|---|---|
| C1 | 6284 | C3H3N3O3 | 129.07 | −8.25 | − | − |
| C2 | 7861 | C6H6N4O2 | 166.14 | −8.63 | − | − |
| C3 | 9432 | C7H8N4O | 164.16 | −9.25 | − | − |

TABLE 1-continued

Identification of the top 40 hits by virtual screening based on the DNA2 3-D model

| No. | NSC No.* | Formula | MW (Dalton) | Docking Scores** | Nuclease inhibition | DNA-dependent ATPase |
|-----|----------|---------|-------------|------------------|---------------------|----------------------|
| C4  | 12754    | C5H8N2OS      | 144.19  | −7.59  | −  | −  |
| C5  | 15765    | C10H6N2O5     | 234.17  | −8.3   | ++ | ++ |
| C6  | 20260    | C9H15N2O15P3  | 484.14  | −10.86 | +  | +  |
| C7  | 33120    | C18H18Cl2O6   | 401.24  | −7.34  | −  | −  |
| C8  | 39858    | C32H36N6O8S4  | 760.92  | −7.41  | ++ | ++ |
| C9  | 42753    | C8H9F3O2      | 194.15  | −6.88  | −  | −  |
| C10 | 55521    | C9H6F6O       | 244.13  | −7.05  | −  | −  |
| C11 | 57727    | C5H9N3O2      | 143.13  | −6.91  | −  | −  |
| C12 | 64878    | C7H7N3S       | 165.22  | −7.04  | −  | −  |
| C13 | 65634    | C11H14N2O     | 190.24  | −7.71  | −  | −  |
| C14 | 79004    | C4H5N5S       | 155.18  | −6.58  | −  | −  |
| C15 | 79197    | C4H9N3O3      | 147.13  | −9.24  | −  | −  |
| C16 | 84922    | C16H11NO3     | 265.26  | −7.6   | −  | −  |
| C17 | 85277    | C16H14N2O3    | 282.29  | −10.06 | −  | −  |
| C18 | 99439    | C11H13N3O5    | 267.24  | −11.61 | −  | −  |
| C19 | 102552   | C6H9N3O2S     | 187.22  | −9.28  | −  | −  |
| C20 | 103797   | C13H17N3O6    | 311.29  | −11.05 | −  | −  |
| C21 | 110391   | C9H6N4O       | 186.17  | −7.14  | −  | −  |
| C22 | 115812   | C16H12FNO3    | 285.27  | −9.03  | −  | −  |
| C23 | 119749   | C3H5N3O2      | 115.09  | −8.03  | −  | −  |
| C24 | 129784   | C10H8N2O4     | 220.18  | −6.75  | −  | −  |
| C25 | 140380   | C19H29ClN6O6S | 504.99  | −7.44  | −  | −  |
| C26 | 157740   | C12H13N5O4    | 291.26  | −11.14 | −  | −  |
| C27 | 166583   | C6H4Cl2N4O    | 219.03  | −7.77  | −  | −  |
| C28 | 170103   | C10H3F7N2     | 284.13  | −6.78  | −  | −  |
| C29 | 211332   | C5H11N5       | 141.17  | −7.86  | −  | −  |
| C30 | 266142   | C6H6N2O3      | 154.12  | −7.27  | −  | −  |
| C31 | 291643   | C9H10N2O6     | 242.19  | −10.87 | −  | −  |
| C32 | 305488   | C14H14N2O4    | 274.27  | −9.26  | −  | −  |
| C33 | 313976   | C51H70N10O24P2S2 | 1340.00 | −12.74 | − | − |
| C34 | 321117   | C10H8N2O2     | 188.18  | −7.81  | −  | −  |
| C35 | 329951   | C11H8N2O      | 184.19  | −8.56  | −  | −  |
| C36 | 360177   | C6H6N4O2      | 166.14  | −8.24  | ++ | ++ |
| C37 | 367734   | C9H12N2O5S    | 260.27  | −10.05 | −  | −  |
| C38 | 375395   | C8H4N2O6      | 224.13  | −8.35  | ++ | ++ |
| C40 | 382898   | C30H18Cl3N15O7| 806.92  | −6.54  | −  | −  |

Figure 1D:
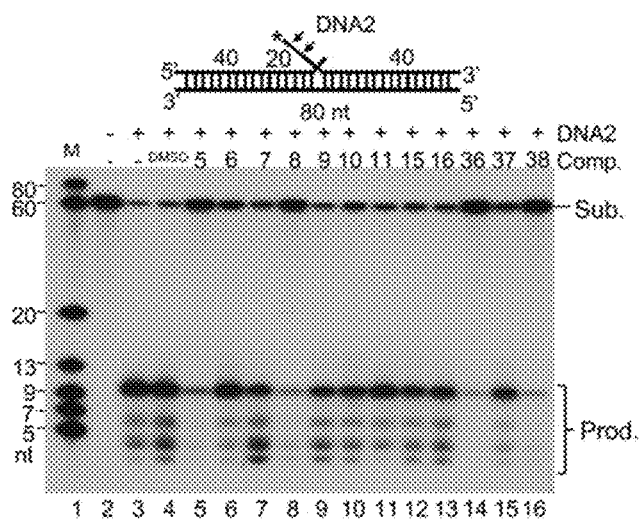
Figure 1E:
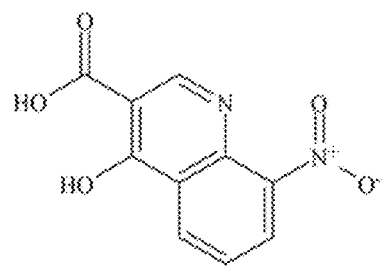

*NSC No.: the NCI's internal ID number
**Docking Score: Based on Schordinger Glide docking software at XP precision Although Site 1 is located in the putative helicase domain, we chose to search for inhibitors that might affect both the nuclease and helicase activities, because previous studies suggested that they may compete for the same DNA binding site. We therefore screened these compounds biochemically for their inhibition of DNA2 nuclease activity using purified recombinant hDNA2 and a well-defined flap substrate. Among the 40 identified compounds, 4 molecules inhibited the DNA2 nuclease activity (FIG. 1D and Table 1). Among these compounds, 4-hydroxy-8-nitroquinoline-3-carboxylic acid, designated as compound C5, had the top Glide XP Docking Score (−8.3 kcal/mol), and displayed the highest cytotoxicity to human cancer cells (FIG. 1E and Table 1). To determine if C5 specifically targets DNA2, we tested if C5 will inhibit the enzyme activities of two similar structure specific nucleases, FEN1 and EXO1. We found that C5 poorly inhibited the activities of the other two nucleases, in contrast to DNA2 (FIGS. 8C-F). Taken together, C5 is a specific inhibitor of DNA2 nuclease activity in vitro.

C. Kinetic Analysis of Compound C5 in Inhibiting DNA2 Activity

Figure 2A:
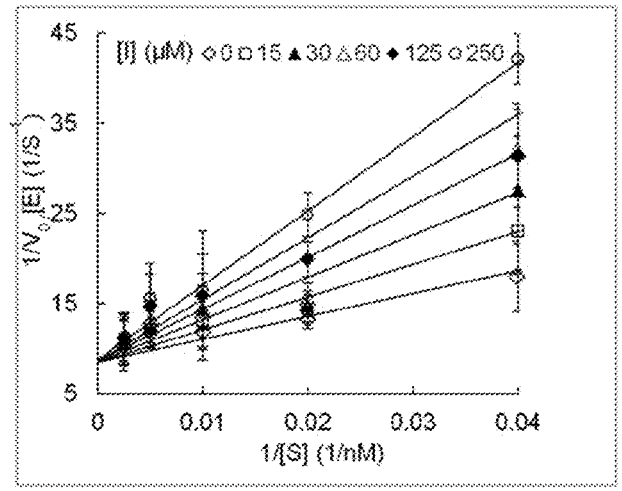
Figure 2B:
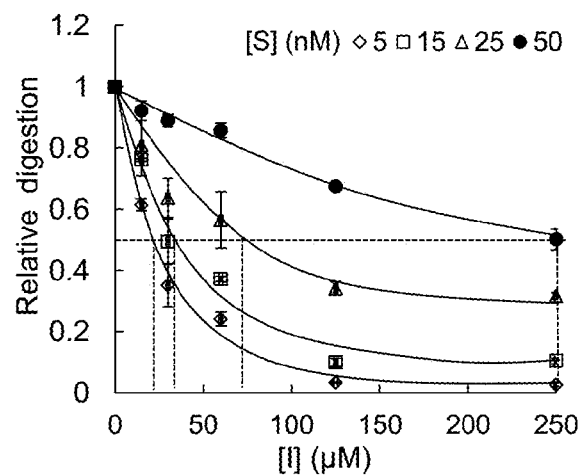
Figure 2C:
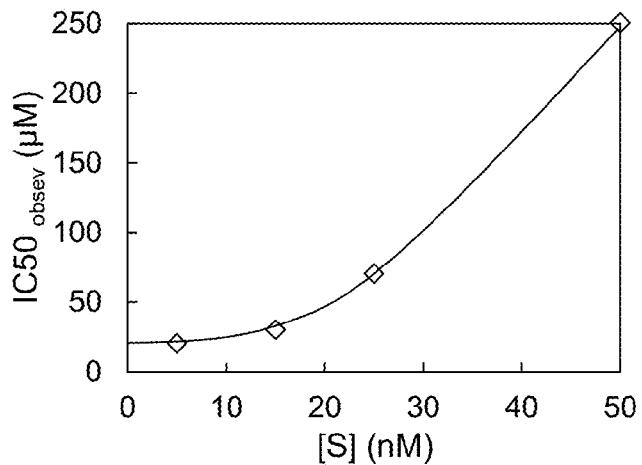
Figure 9A:
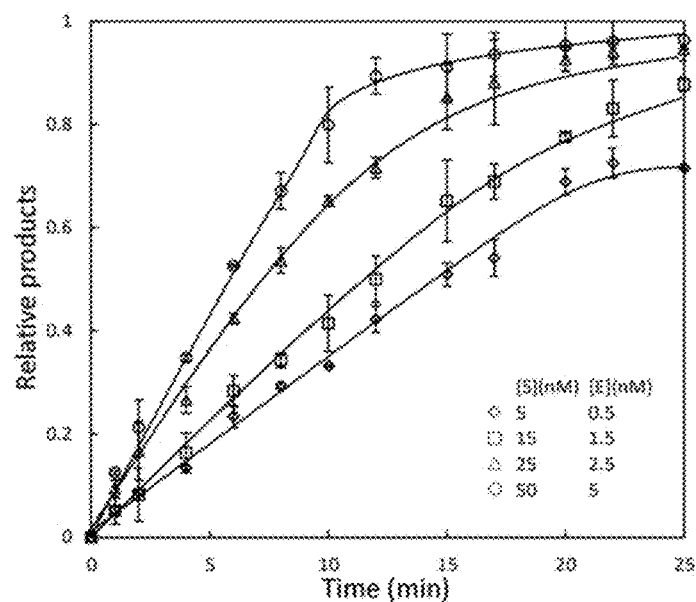
FIGS. 9A-9B. (see also FIGS. 2A-2G)

In order to determine the IC50 of C5 for inhibition of the nuclease activity of DNA2, we conducted kinetic analyses. Using a flap DNA substrate, we first studied the time course of the nuclease activity in order to determine the proper time interval for kinetic analysis at various substrate concentrations (FIG. 9A). We found that the enzyme activity was linear at 1-10 minutes, and we conducted the assays in this range. To evaluate the mechanism of inhibition of nuclease activity by C5, we measured the nuclease activity of DNA2 at various concentrations of inhibitor and substrate (FIG. 2A). Using a Lineweaver-Burk plot, we evaluated the competition patterns using competitive, noncompetitive, and uncompetitive models. The competitive inhibition model fits best to the inhibition data with C5. To extract the intrinsic inhibition constant of C5 for DNA2, we obtained apparent inhibition constant, or IC50, values, for C5 at a series of substrate concentrations (FIG. 2B). Extrapolation of the observed IC50 values to limiting substrate concentrations, as described in the Experimental Procedures section, gave an inhibition constant of 20 μM (FIG. 2C).

Figure 9B:
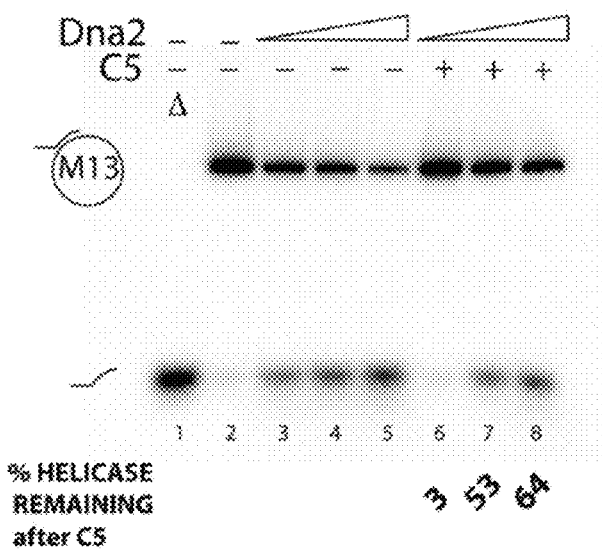

The kinetic studies suggested that C5 acts as a competitive inhibitor of DNA2 nuclease activity. A competitive model predicts C5 binding to DNA2 should block binding of DNA2 to the DNA substrate. Consistent with the model, we found that C5 inhibited the ATPase activity of DNA2, which is dependent on DNA binding (FIGS. 2D and 2E). To further test this model, we evaluated DNA2 substrate binding in the presence of various C5 concentrations directly, by electrophoretic mobility shift assay (EMSA). We found that DNA2 effectively bound flap DNA substrates, leading to reduced electrophoretic mobility; but the addition of C5 reduced the formation of the DNA2-substrate complex (FIGS. 2F and 2G). The inhibitor concentration needed to reduce the DNA2-substrate complex formation to 50% is 30 µM, which is comparable to the IC50 value for inhibition of the DNA2 nuclease activity. Finally, we tested the ability of C5 to inhibit DNA2 helicase activity. Using the DNA2 helicase substrate in which an M13 phage DNA is hybridized to a 5' tailed oligonucleotide (Masuda-Sasa et al., 2006), we found that C5 inhibits the 5' to 3', end-dependent DNA helicase activity of DNA2 (FIG. 9B, compare lanes 3 and 6, 4 and 7, 5 and 8) (Balakrishnan et al., 2010; Masuda-Sasa et al., 2006). Based on our results, we suggest that although our homology structure does not show the nuclease domain, that contacts in both ATPase and helicase domains are required for nuclease activity, consistent with the recent X-ray crystal structure of murine DNA2 (80% identical to human DNA2).

Figure 10A:
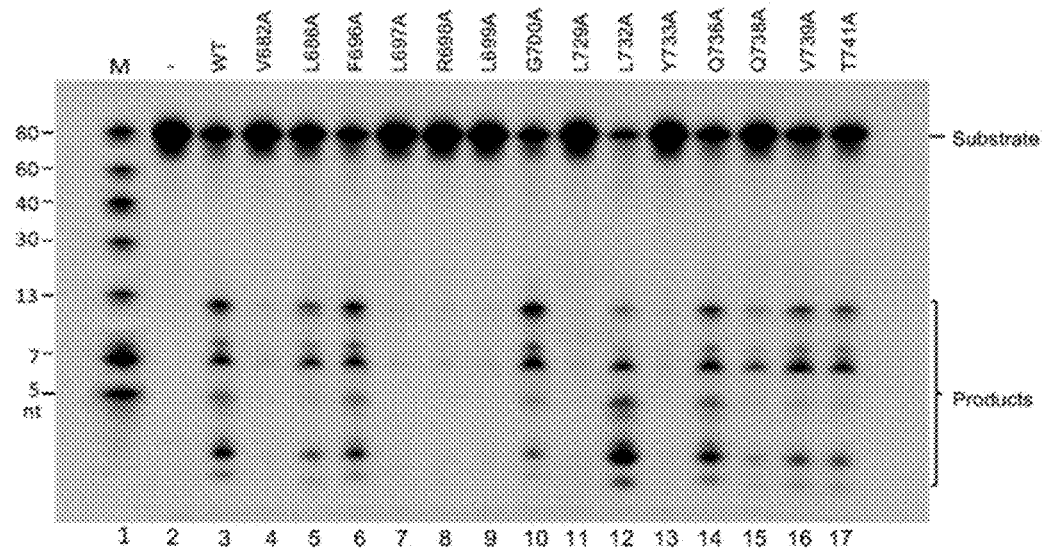
FIGS. 10A-10C. 14 residues in Site 1 were mutated to determine the DNA2 binding capacity to the inhibitor C5 (See also FIGS. 3A-3C).
Figure 10B:
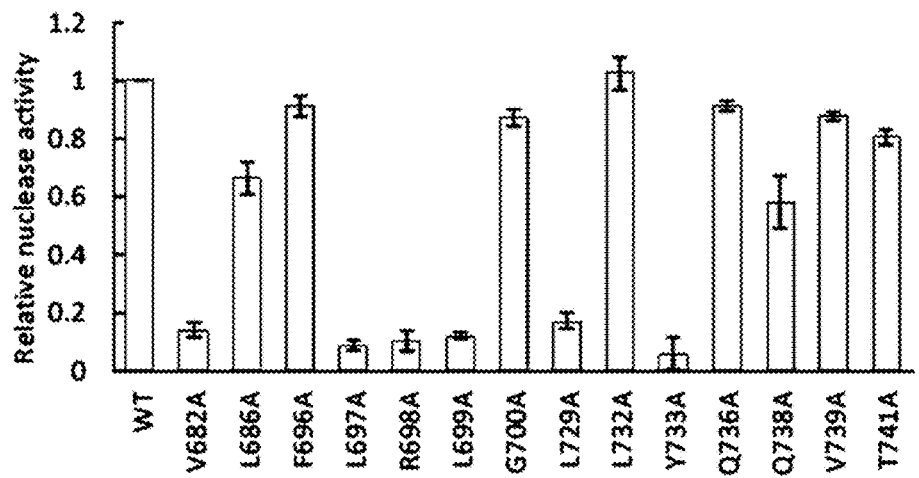
Figure 10C:
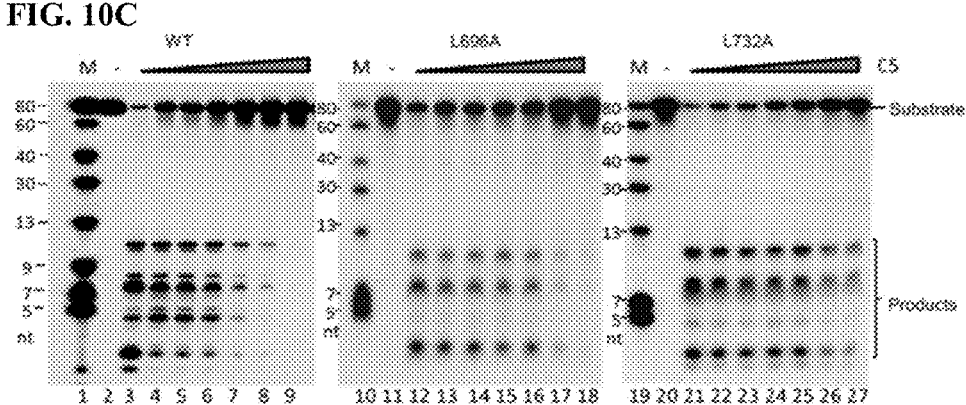

D. Validation of Site 1 on DNA2 as the Binding Pocket for Compound C5 and as a DNA Binding Motif C5 was identified by virtual screening for small molecules that bind to a pocket (Site 1) near the putative DNA binding site in our computational DNA2 model. Based on the 3-D model, we searched the residues within 6A spheres around the predicted C5 binding site. We identified multiple residues, including V682, L686, F696, L697, R698, L699, G700, L729, L732, Y733, Q736, Q738, V739, and T741, that may play a key role in coordinating C5 binding (FIG. 3A). To test if C5 indeed binds to the pocket at Site 1, we substituted these residues with alanine. The mutant and WT DNA2 proteins were purified and the nuclease activities were assayed. Although Site 1 lies in the helicase domain, many of the mutations altered the nuclease activity in the absence of inhibitor, presumably because the Site 1 pocket is close to the putative DNA substrate binding pocket. These are the first mutations within the helicase domain that have been demonstrated to concomitantly affect the nuclease activity. Other mutants, however, maintained intact nuclease activity (FIGS. 10A and 10B). We chose F696A and L732A with enzyme activity similar to the WT to test their sensitivity to compound C5. Both the nuclease activity and DNA binding activity of the two mutants were less sensitive to C5 than wild type (FIGS. 3B and 3C and FIG. 10C). The compound C5 IC50s for nuclease activities and DNA substrate binding were greater than 250 µM for F696A and L732A, compared to 30 µM for the WT. This suggests that the mutations impair the interaction of C5 with the designated binding site (Site 1) of DNA2 and that this site does define a crucial flap substrate DNA binding domain.

E. C5 Displays On-Target Effects on DNA2

Figure 4B:
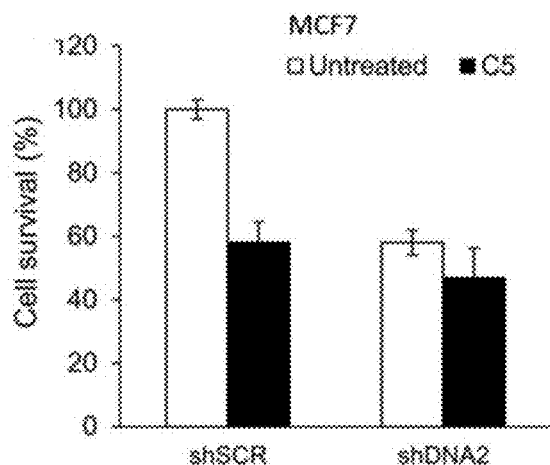
Figure 4C:
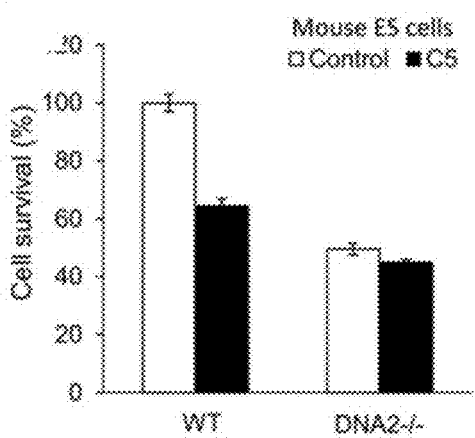

Next, we determined the cytotoxicity of DNA2 inhibitor C5 and evaluated whether the compound had on-target effects on DNA2 in cultured cells. We have measured IC50 values of C5 with a panel of 18 cell lines of 4 major types of cancers by a cell proliferation assay (Chou 2010). The IC50 values among the different cell lines varied from 7 µM to 70 µM, which is comparable to the estimated enzymatic IC50 value of 20 µM (FIG. 4A). Furthermore, we considered that if the toxic effects of C5 were due to targeting DNA2, then cells lacking DNA2 should be resistant to the effects of compound C5. As anticipated, we found a reduced spontaneous survival rate in human and mouse cells with either shRNA-mediated knockdown (FIG. 4B) or knockout (FIG. 4C) of DNA2. We found that WT MES cells and human MEF7 cancer cells treated with C5 showed a 60% survival rate, compared to the untreated WT control (FIGS. 4B and 4C), a result similar to the effects of DNA2 knockdown and knockout. Importantly, we found that treatment of dna2$^{-/-}$ MES or DNA2 knockdown human cancer cells with C5 did not further reduce the survival rate, suggesting that the cytotoxic effects of compound C5 were primarily due to specific effects on DNA2 at the given concentration. This suggests that due to residual viability, those normal cells may be less sensitive to inhibitors than cancer cells, with repair and checkpoint defects. This also suggests that other enzymes, such as FEN1 or EXO1, cannot completely compensate for the loss of DNA2, indicating that DNA2 inhibitors are likely to have significant physiological effects in cancer cells. The results suggest that C5 is a potent and specific inhibitor of DNA2 and that virtual docking is a valid method to help identify DNA2-specific drugs.

Figure 13A:
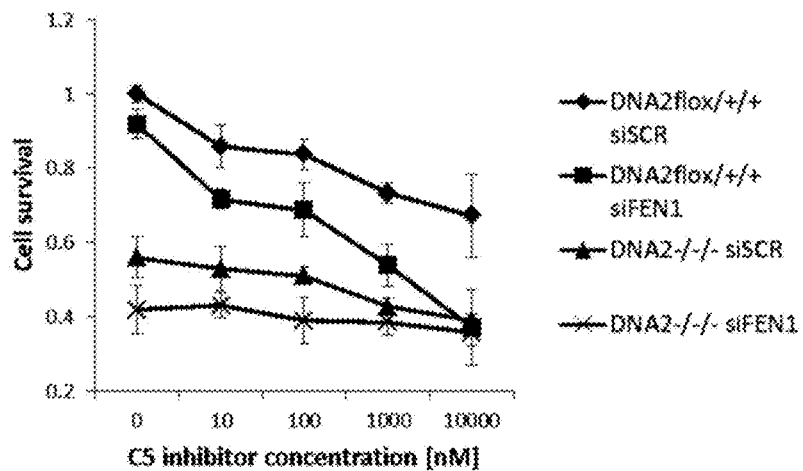
FIGS. 13A-13C. Synergy between C5 and FEN1. EXO1 or MRE11 knockdown indicates C5 has on-target effects in vivo in human cancer cells. On day 1, HCT116 DNA2$^{flox/+/+}$ and HCT116 DNA2$^{flox/-/-}$ cells (3*10$^6$ were plated in 10 cm dishes, respectively. On day 2, the genetic knockout of DNA2 was induced with tamoxifen as previously described (Karanj a et al., 2014). Control wells contained EtOH. On day 3, the tamoxifen floxed cells, now DNA2$^{-/+/+}$ and DNA2$^{-/-/-}$, and DNA2$^{flox/+/+}$ controls were plated on 24 well plates, 20,000 to 30,000 cells per well, and incubated overnight. On day 4, wells were transfected with 20 pmole control SCR siRNA or FEN1 (FIG. 13A), EXO1 (FIG. 13B), or MRE11 (FIG. 13C) si RNAs, respectively, as previously described using GeneMute. siRNAs were obtained from Invitrogen: FEN1 (H55103627, H55103629, H55176903), MRE11 (H55142960, H55142961, H55181171), EXO1 (H55113557, H55113558, H55113559). Cells were incubated overnight. To test if inhibition of DNA2 by C5 showed synthetic lethality with FEN1, EXO1 or Mre11 si RNA knockdown, C5 was added to each well of DNA2$^{flox/+/+}$, as indicated (compare red and blue curves). Cells were cultured for an additional 3 days, until DNA2$^{flox/+/+}$ cells lacking C5 were confluent. As a control for the efficacy of C5, the effect of genetic knockdown of DNA2 was tested in the presence the respective siRNA treated DNA2$^{-/-/-}$ (gray curves). Cells were then washed with PBS, trypsinized and stained with tryphan blue to differentiate live cells from dead cells. Cells were counted microscopically in a Neubauer chamber. Error bars represent data from duplicate experiments. Both inhibition of DNA2 by C5 and genetic knockout of DNA2 with tamoxifen produces synthetic lethality with FEN1, EXO1 or MRE11 deficiency.
Figure 13B:
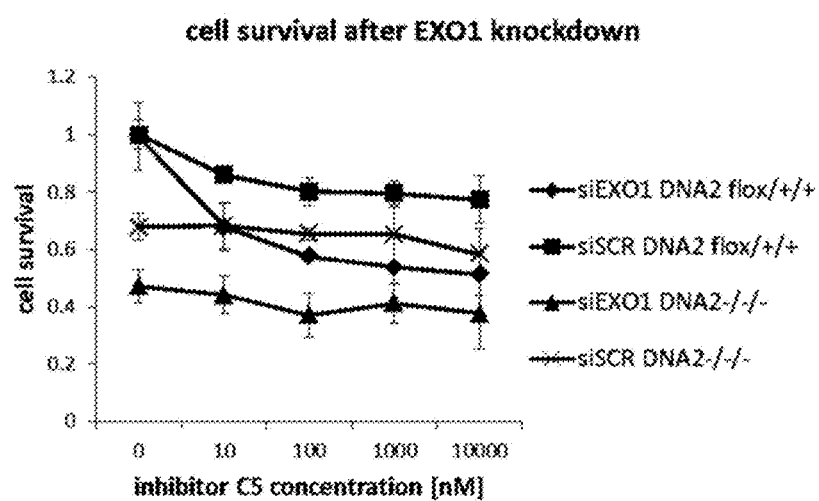
Figure 13C:
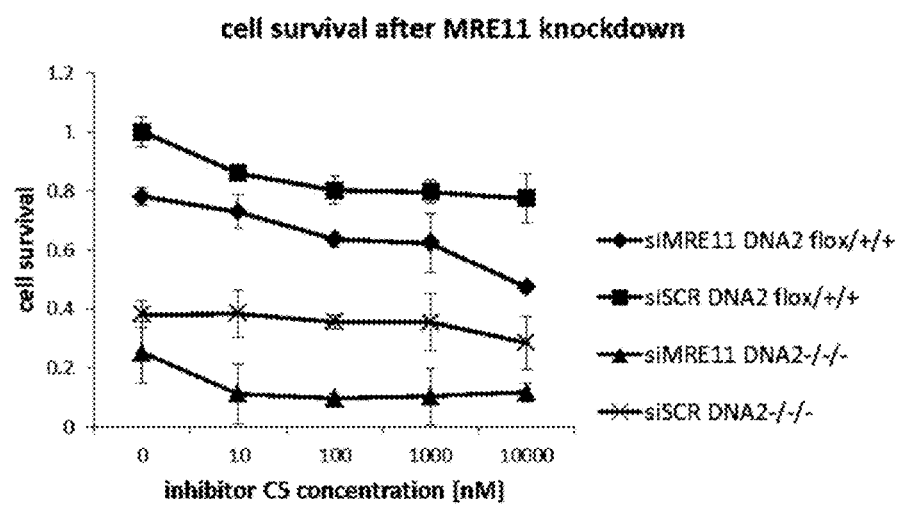

In yeast, pathways mediated by DNA2 overlap with repair or replication by FEN1, EXO1, or MRE11 and not with others (Budd, M. E., Tong, A. H., Polaczek, P., Peng, X., Boone, C., and Campbell, J. L. (2005). A network of multi-tasking proteins at the DNA replication fork preserves genome stability. PLoS genetics 1, e61). Thus, mutants defective in FEN1, EXO1, or MRE11 are viable only in the presence of active DNA2. Double mutants deficient in DNA2 and FEN1, EXO1, or MRE11, respectively, are invisible, especially in the presence of DNA damage. This effect is called synthetic lethality. To test for synthetic lethality, deficiency in DNA2, can be induced either by genetic mutation or, if a specific inhibitor is available, by inhibition of DNA2. We reasoned that if DNA2 is the major cellular target of C5, then cells deficient in FEN1, EXO1, or MRE11 should be hypersensitive to C5, i.e. C5 should synergize with deficiency in any one of these three genes. We have now shown that this is the case in both yeast and in human cells (FIGS. 13A-13C, human cells and FIG. 14, yeast cells). FIGS. 13A-13C show that siRNA knockdowns of FEN1, EXO1, or MRE11 are killed by increasing levels of C5, while the cells treated with scrambled siRNA, are resistant. To control for the efficacy of C5, we took advantage of a cell line carrying a conditional genetic knockout of DNA2, HCT116$^{flox/-/-}$ (Karanja, K. K., Lee, E. H., Hendrickson, E. A., and Campbell, J. L. (2014) Cell Cycle 13, 1540-1550). After floxing, i.e. induction of Cre nuclease with tamoxifen, this strain becomes a complete DNA2 knockout. As shown in FIGS. 13A, 13B, and 13C, gray curves, the knockout of DNA2 is synthetically lethal with deficiency in any of the three genes and the level of sensitivity to 10 µM C5 is similar to the level of lethality seen in the DNA2$^{-/-/-}$. (The Mre11 result is also described in Liu et al EBioMedicine 6 (2016) 73-86). Both inhibition of DNA2 by C5 and genetic knockout of DNA2 with tamoxifen produces synthetic lethality with FEN1, EXO1 or MRE11 deficiency.

Yeast contains many genes encoding transporters that prevent accumulation of drugs to toxic levels. Fortunately, these genes are coordinately regulated by Pdr1 (pleiotropic drug resistance regulator). When Pdr1 is fused to gene encoding a strong repressor, Pdr1 binds to many resistance genes and the repressor turns off expression, allowing accumulation of inhibitors. The chimeric repressor is expressed on a plasmid and can be easily transferred to many genetic backgrounds (Nitiss and Wang, 1988; Stepanov et al., 2008). This has improved yeast as a model for testing therapeutic agents in mechanism based-drug discovery.

We have created a number of drug-sensitive yeast strains that allow us to test the efficacy of DNA2 inhibitors in ways that are highly likely to measure only on-target effects of the compounds (Stepanov, A., Nitiss, K. C., Neale, G., and Nitiss, J. L. (2008); Mol Pharmacol 74, 423-431). In particular, rad27 mutants, lacking FEN1, specifically need DNA2 to survive in the presence of damage. FEN1 is not inhibited by C5 (Liu et al EBioMedicine 6 (2016) 73-86). So we tested if the inhibitor increased the sensitivity of rad27 to DNA damage. As shown in Fig. N+1, DNA2i C5 synergizes with MMS and with deletion of rad27, mimicking the exact and specific behavior of dna2 mutants (Budd, M. E., and Campbell, J. L. (1997) Mol Cell Biol 17, 2136-2142). We further show that derivative 2 of C5 (also referred to herein as C5-2, shown below) is more effective than C5. The compound C5-2 has the formula:

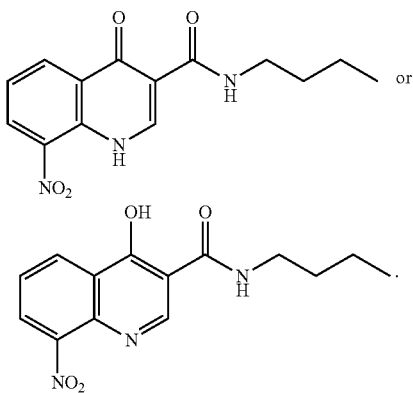

Figure 14:
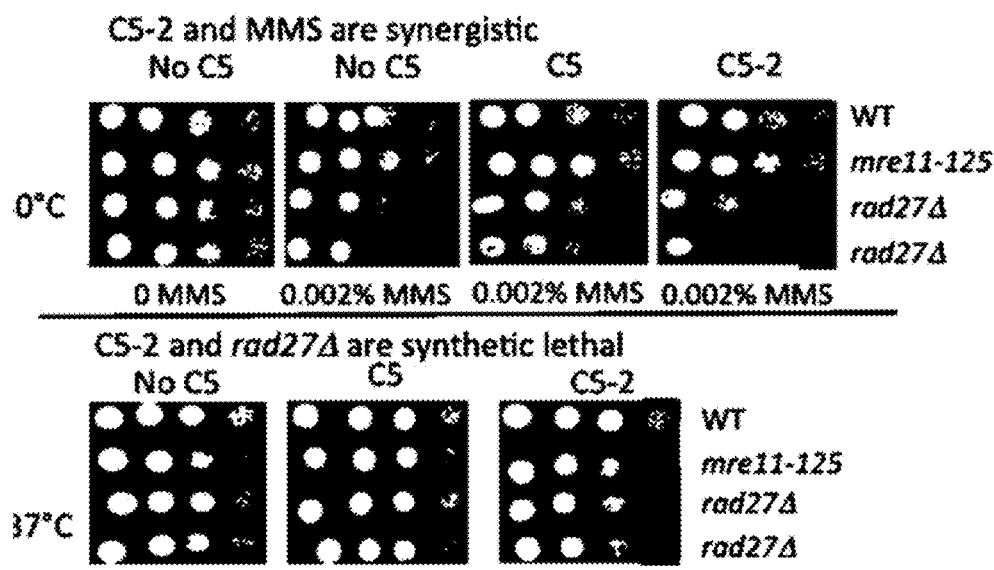
FIG. 14. Yeast cells with the designated genotypes were treated with the indicated levels of C5 and a derivative, C5-2, and survival after treating with the DNA damaging agent methyl methane sulfonate or incubating at high temperature was determined by dilution assay. Colonies represent serial 10 fold dilutions of the yeast strains. The two rows labeled rad27 are duplicate experiments. C5 suppresses cisplatin sensitivity in FANCD2−/− fibroblasts. We previously showed that knockdown of DNA2 suppressed the cisplatin sensitivity of FANCD2−/− fibroblasts. This suggests that C5 should also suppress the cisplatin sensitivity of FANCD2−/− cells, which might protect non-cancerous cells in FA patients from treatment of tumors with cisplatin.

As seen in FIG. 14, this is a dilution series of yeast, and in the presence of inhibitor, rad27 is much more sensitive to MMS and to high temperature than in the absence. Wild-type is not affected by these levels of C5 drugs. This shows that the inhibitor functions in yeast and that its target is likely DNA2.

Figure 15:
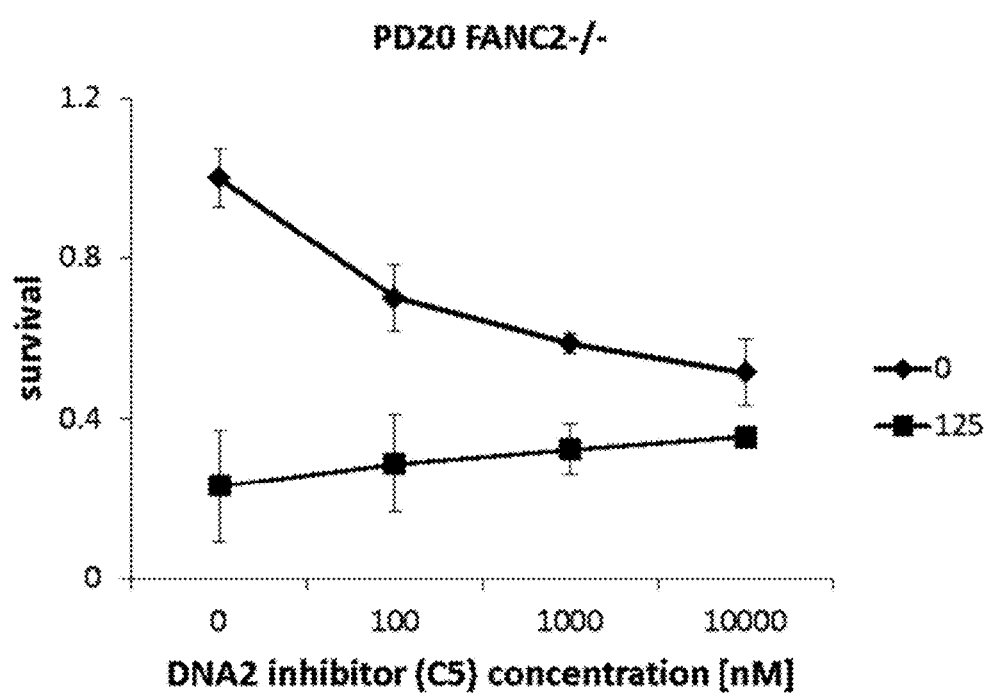
FIG. 15. Cells were treated with cisplatin in the presence of increasing amounts of C5 or in the absence of C5. The experiment was performed in duplicate.

We previously showed that knockdown of DNA2 suppressed the cisplatin sensitivity of FANCD2−/− fibroblasts (Karanja, K. K., Lee, E. H., Hendrickson, E. A., and Campbell, J. L. (2014) Cell Cycle 13, 1540-1550). This suggests that C5 should also suppress the cisplatin sensitivity of FANCD2−/− cells, which might protect non-cancerous cells in FA patients from treatment of tumors with cisplatin (see FIG. 15). Cells were treated with cisplatin in the presence of increasing amounts of C5 or in the absence of C5. Survival was determined as described in Karanja et al (Karanja, K. K., Lee, E. H., Hendrickson, E. A., and Campbell, J. L. (2014) Cell Cycle 13, 1540-1550). The experiment was performed in duplicate. As shown in FIG. 15, at 125 nM cisplatin, cells treated with 10 µM C5 showed an increase in survival compared to cells not treated with C5.

Figure 5A:
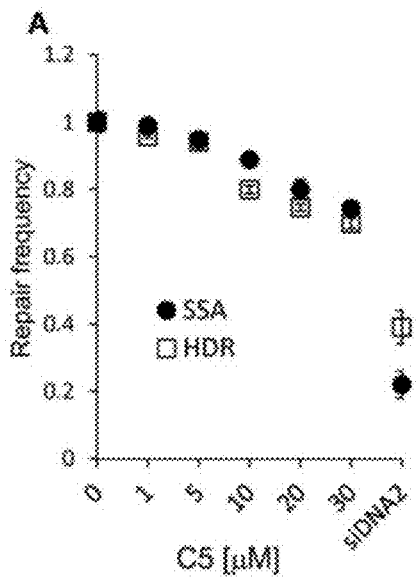
FIGS. 5A-5H. Inhibitor C5 suppresses resection-related homology directed repair (HDR) and single strand annealing (SSA) and causes accumulation of phosphorylated RPA foci (see also FIGS. 11A-11B).
Figure 5B:
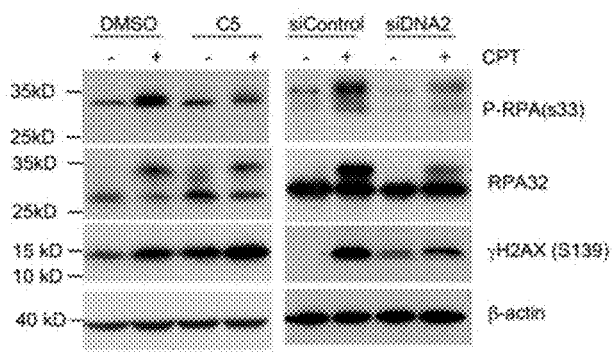
Figure 5C:
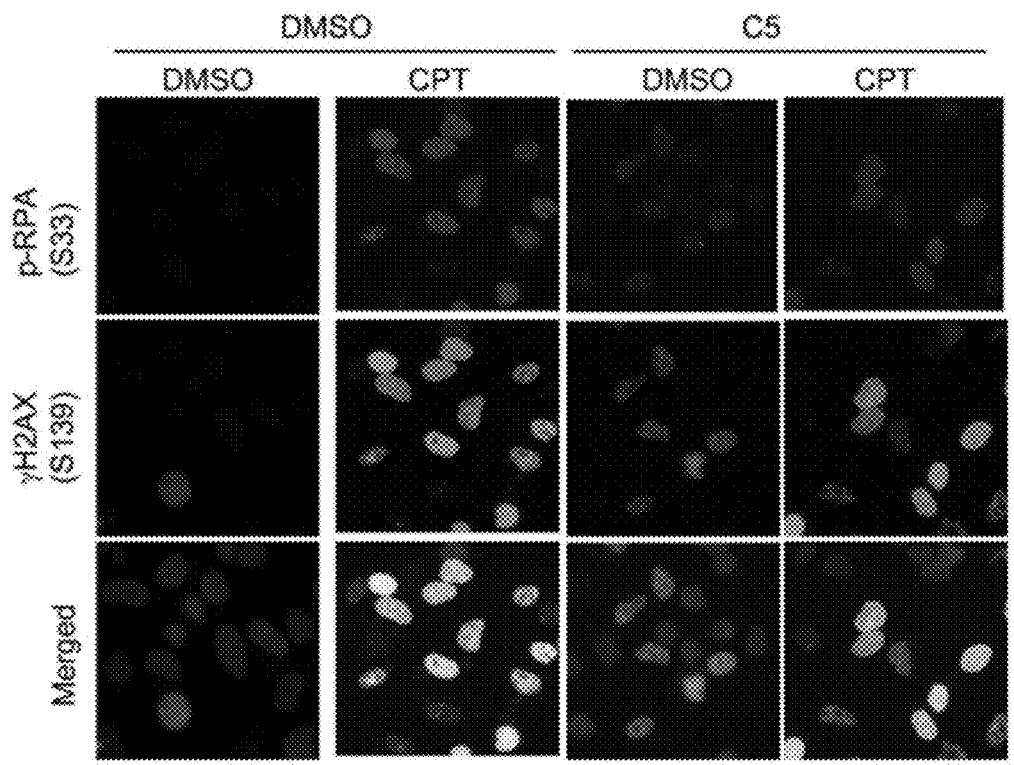
Figure 5D:
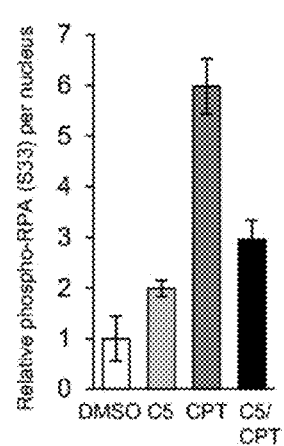
Figure 5E:
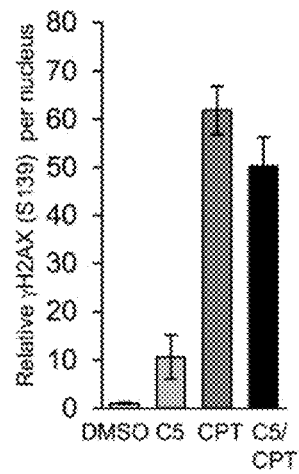
Figure 5F:
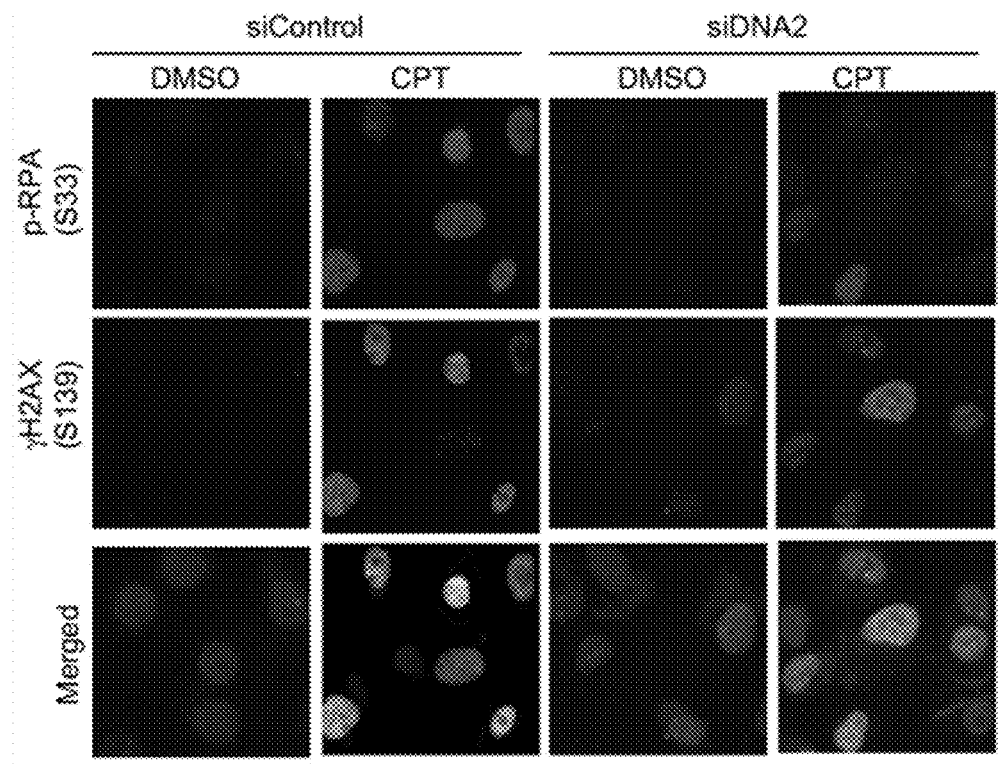
Figure 5G:
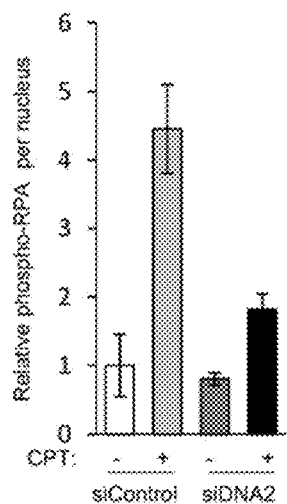
Figure 5H:
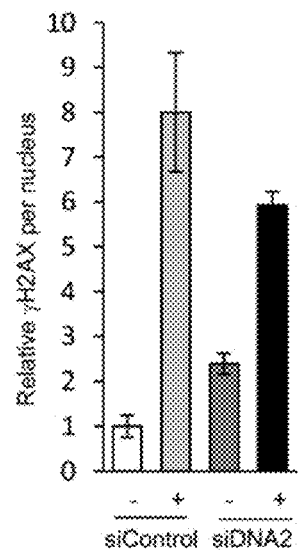
Figure 11A:
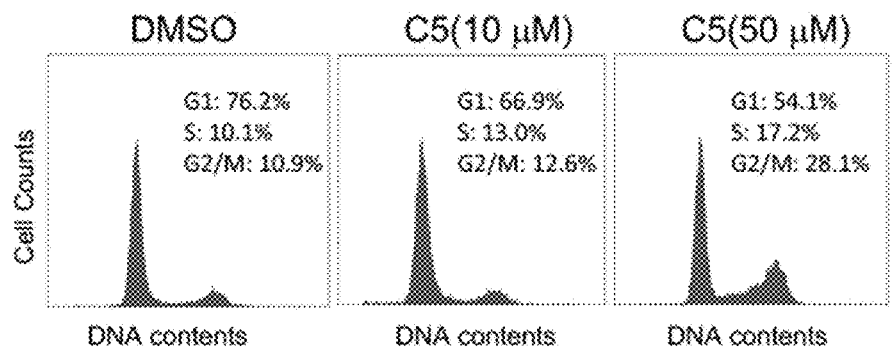
FIGS. 11A-11B.
Figure 11B:
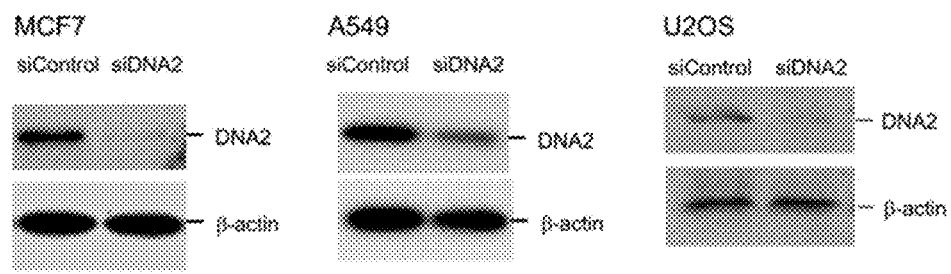

F. C5 Suppresses DNA DSB Repair End Resection, Over-Resection of Nascent DNA in Cells Defective in Fork Protection, and Restart of Stalled DNA Replication Forks To further validate C5 as a DNA2 inhibitor, we tested its effects on DNA2 functions known to be affected by knockdown or deletion of DNA2 in previous studies (Howard et al., 2015; Karanja et al., 2014; Karanja et al., 2012; Peng et al., 2012). We first determined the effect of C5 on two recombination pathways, SSA (single-strand annealing) and homologous recombination (HR), using I-SceI/GFP-based reporter assays. Since these pathways are most active in S/G2 (FIG. 11A), we determined GFP positive cells on the G2 population. We found that both SSA and HR were reduced by C5 in a dose-dependent manner (FIG. 5A). For comparison, at 60 µM C5, SSA and HR were reduced to the same level as in an siRNA DNA2 knockdown carried out in parallel (FIG. 11B).

We next wanted to verify if the defects in recombination assays were due to inhibition of end resection. During the early steps of recombination, DNA2 in complex with BLM or WRN protein resects DSB ends, producing ssDNA 3' overhangs (Karanja et al., 2012; Nimonkar et al., 2011; Sturzenegger et al., 2014). The ssDNA overhangs are coated with RPA, which is then phosphorylated by ATR (Zou and Elledge, 2003). To measure resection, we determined the level of phosphorylated RPA2 (S33 or S4/8) in cells treated with C5 in the presence or absence of CPT. CPT stabilizes cleavable complex intermediates in topoisomerase I reactions which collapse into DSBs when encountered by a replication fork (Hsiang et al., 1989; Patel et al., 2012). CPT increased phosphorylated RPA2 (P-RPA), as measured on western blots and by immunofluorescence of P-RPA2 foci (FIGS. 5B-E). C5 significantly reduced the CPT-induced P-RPA level in γH2AX-positive cells (FIGS. 5B-E). The level of C5 used here reduced RPA phoshporylation to the same extent as we observed in parallel studies using siRNA DNA2 knockdown (compare FIGS. 5C-5E and 5F-5H). Interestingly, we also noted that C5 alone caused background increase in γH2AX (FIGS. 5B-5H), presumably because the DNA2 inhibitor itself causes replication stress, similarly as shown previously for shDNA2 knockdown (Duxin, J. P., Dao, B., Martinsson, P., Rajala, N., Guittat, L., Campbell, J. L., Spelbrink, J. N., and Stewart, S. A. (2009). Human Dna2 is a nuclear and mitochondrial DNA maintenance protein. Molecular and cellular biology 29, 4274-4282. Duxin, J. P., Moore, H. R., Sidorova, J., Karanja, K., Honaker, Y., Dao, B., Piwnica-Worms, H., Campbell, J. L., Monnat, R. J., and Stewart, S. A. (2012); Karanja et al., 2012).

Figure 6A:
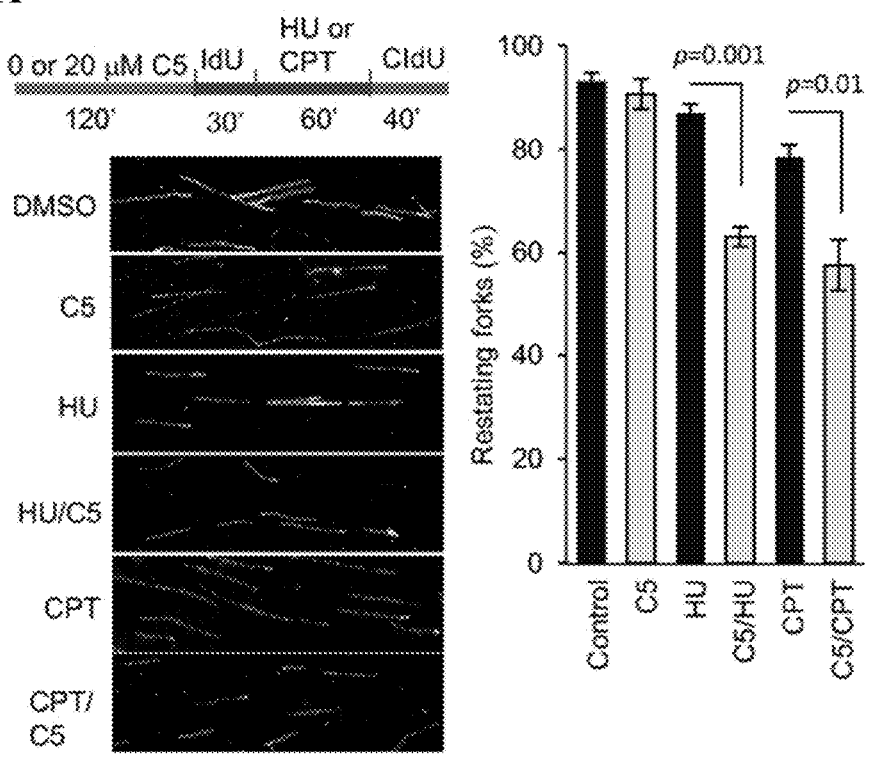
FIGS. 6A-6D. C5 suppresses restart of stalled DNA replication forks and over-resection of nascent DNA in cells defective in fork protection (see also FIGS. 12A-12B).
Figure 6B:
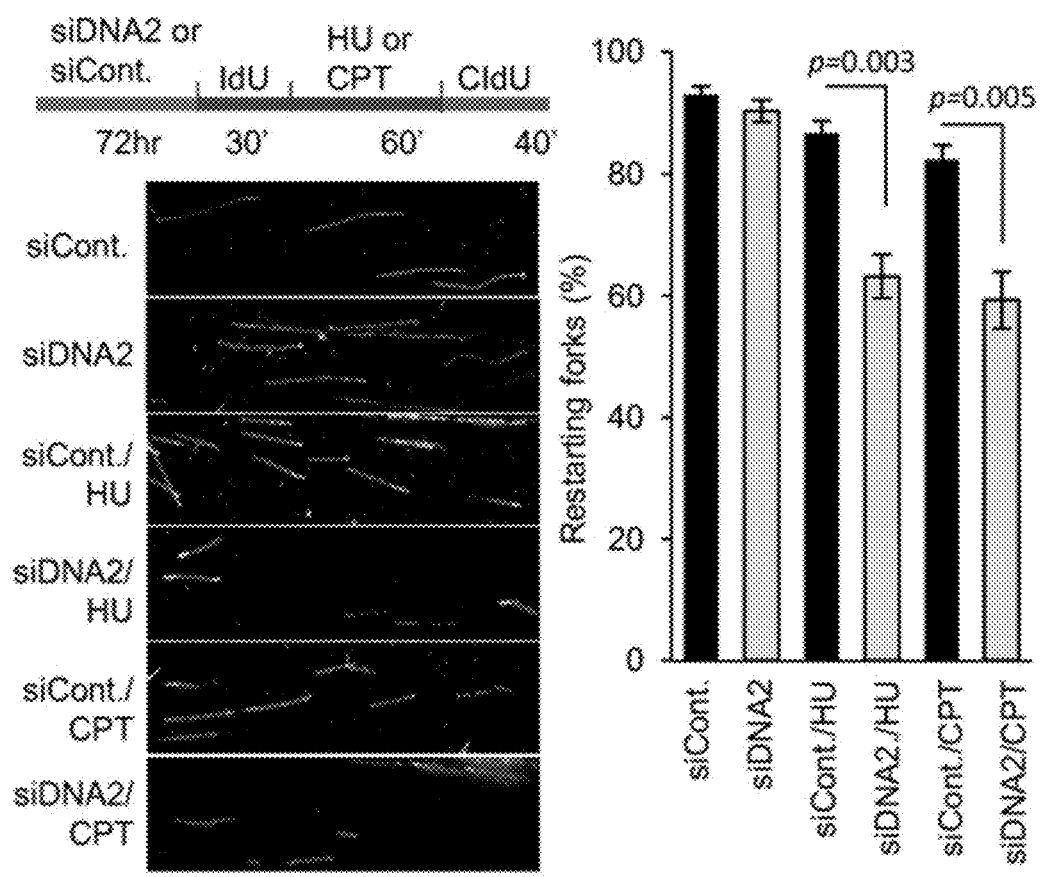
Figure 12A:
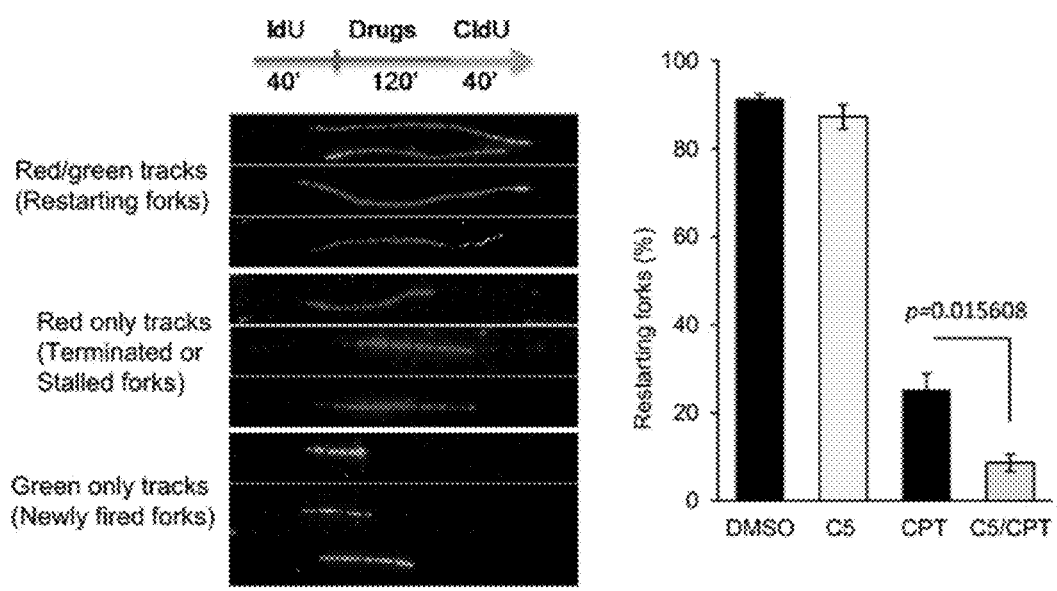
FIGS. 12A-12B. (Also see FIGS. 5A-5H).

When DNA replication forks are stalled in S-phase, DNA2 plays an important role in stabilizing the stalled forks, in preventing DSB formation, and in resection of the nascent strand to prepare for the restart of replication (Hu et al., 2012; Karanja et al., 2012; Thangavel et al., 2015; Weitao et al., 2003b; Weitao et al., 2003d). A recent study using DNA fiber assays indicated that knockdown of DNA2 by siRNAs inhibits replication fork restart in HU-treated cells or cells treated with low levels of CPT (Thangavel et al., 2015). We have conducted DNA fiber assays to evaluate the effect of C5 on restart of forks treated with low levels of CPT, which in contrast to high CPT levels does not cause DSBs but results in increased positive supercoiling and fork slowing and stalling (Ray Chaudhuri et al., 2012), or with HU, which inhibits production of nucleotide precursors. In absence of C5, 80% or 75% of replication forks could restart (red-green tracts) in HU-treated or CPT-treated cells, respectively (FIG. 6A). However, 20 µM C5 reduced the percentage of restarting forks to 60% and 50% in the HU-treated or CPT-treated cells, respectively (FIG. 6A). This level of inhibition at 20 µM C5 was equivalent to knockdown of DNA2 using siRNA (FIG. 6B). These results extend previous studies on DNA2 functions during replication restart (Ray Chaudhuri et al., 2012; Teicher, 2008) and show that DNA2 is more sensitive to inhibition at stalled replication forks than at a single DSB (FIGS. 5A-5H). C5 also inhibited restart in cells treated with high levels of CPT, resulting in replication associated DSBs (FIG. 12A).

Figure 6C:
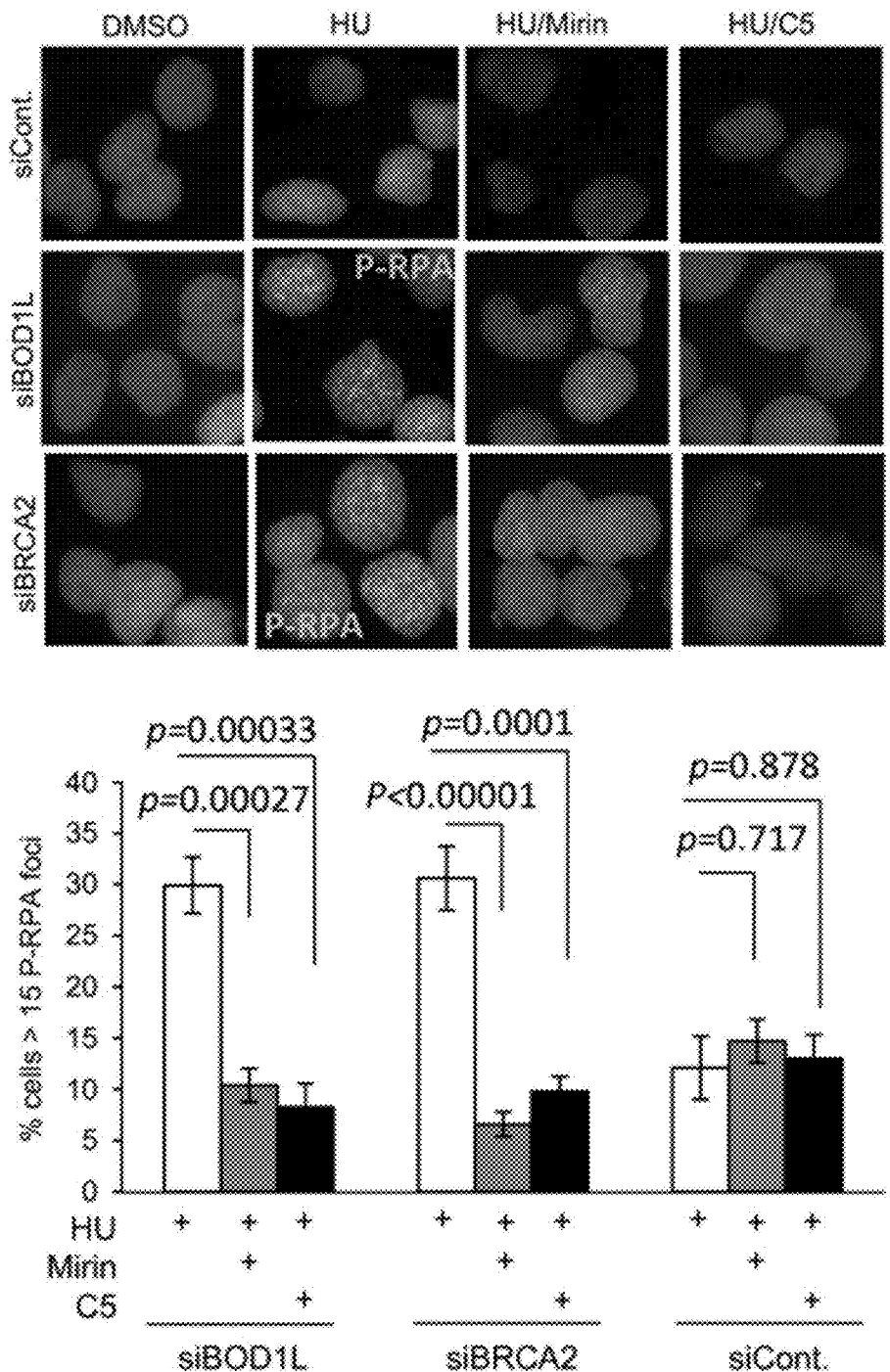
Figure 6D:
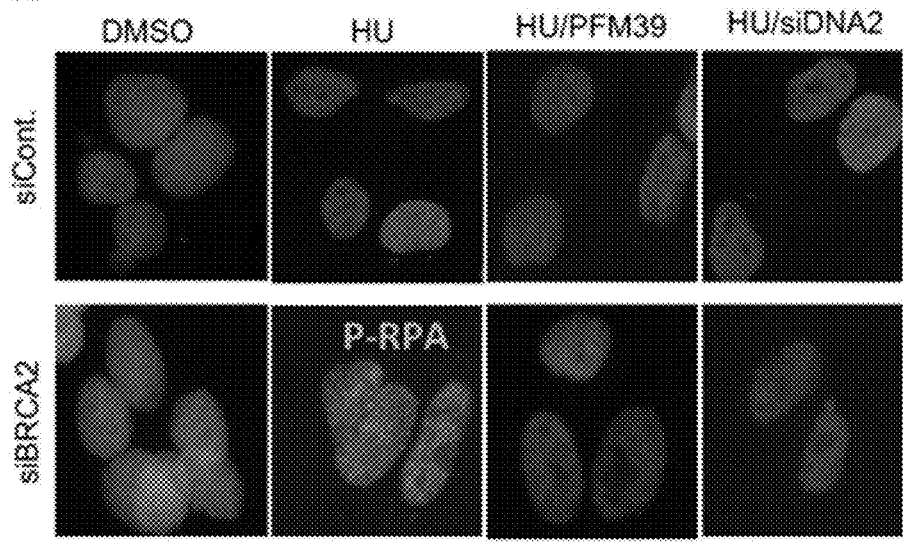
Figure 6D:
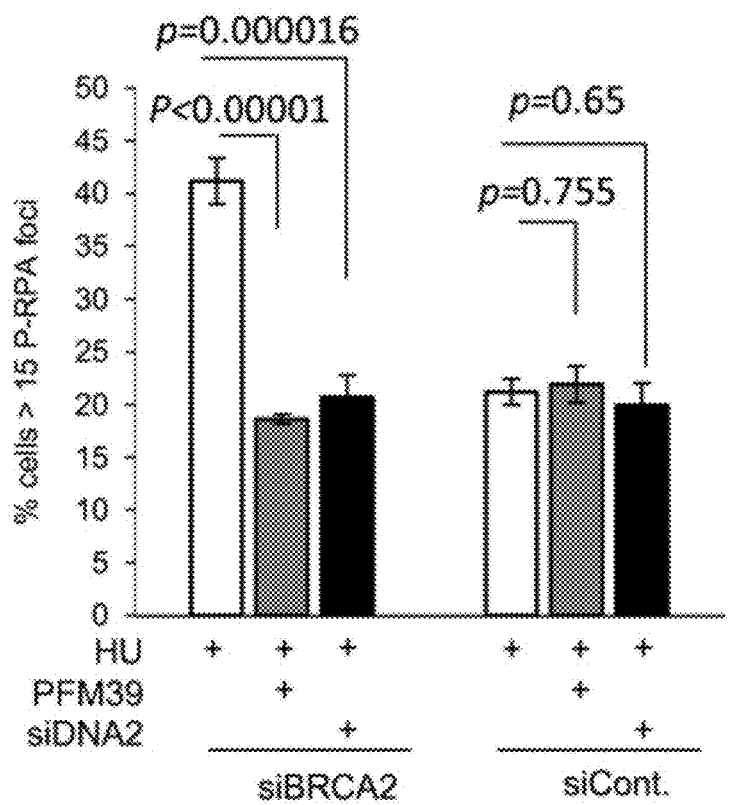
Figure 12B:
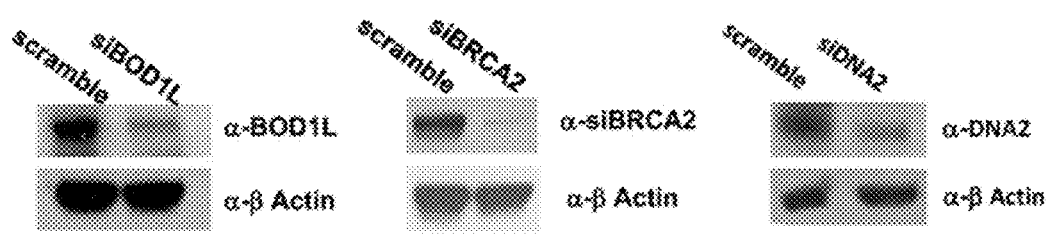

Fork protection is a DNA break repair-independent pathway suppressing genomic instability (Schlacher et al, 2011; Schlacher et al, 2012). The fork protection pathway is mediated by BRCA2, BRCA1, RAD51, members of the Fanconi anemia pathway, and BOD1l. In the absence of any of these factors, excessive nascent DNA degradation occurs at stalled replication forks. This degradation is prevented if the end-resection protein MRE11 is inhibited either by siRNA knockdown or by inhibition of MRE11 nuclease by the small molecule mirin (Schlacher et al., 2011; Schlacher et al., 2012). MRE11 functions upstream of DNA2 in resection of double-strand breaks, and DNA2, in addition to MRE11 has been implicated in over-resection at stalled replication forks in BOD1L and in RAD51 impaired cells, since over-resection is suppressed by knockdown of DNA2 in the absence of BOD1L or in a RAD51 mutant cell line (Higgs et al., 2015; Wang et al., 2015). To determine if C5, like DNA2 knockdown, suppressed nascent DNA degradation and resulting accumulation of ssDNA at stalled forks, we monitored phospho-RPA (P-RPA) foci in BRCA2- or BOD1L-depleted or mock transfected U2OS cells with and without HU treatment (FIGS. 6C and 6D). In the absence of HU, in mock-depleted cells we saw few cells with greater than 15 P-RPA foci/per cell, and neither mirin nor C5 significantly decreased the number of P-RPA positive cells, consistent with the fork protection pathway being intact (FIG. 6C). After treatment of the BRCA2- or BOD1L-depleted U2OS cells with HU, which stalls forks but is not expected to produce DSBs (Petermann et al., 2010; Schlacher et al., 2011; Schlacher et al., 2012), and which are fork protection defective, we observed a dramatic increase in P-RPA positive cells indicative of nascent DNA degradation upon treatment with HU (FIG. 6C and FIG. 12B). This degradation was suppressed by C5. The potency of C5 was estimated by comparing the effect of mirin, the MRE11 inhibitor, in the same experiment. Remarkably, 20 µM C5 has a comparable potency to 50 µM mirin in reducing this degradation (FIGS. 6C-6D). To exclude off-target effects of mirin in our experiments, we showed that another potent MRE11 inhibitor, PFM39 reduced P-RPA foci to the same extent as mirin in the BRCA2-deficient cells (FIG. 6D). Finally, we showed in a parallel experiment that the level of reduction in P-RPA foci caused by C5 in BRCA2-deficient cells is also equivalent to that observed in a DNA2 knockdown (FIG. 6D and FIG. 12B). Our results are in keeping with previous work showing that knockdown of DNA2 counteracts excessive nascent strand degradation in both BOD1L and in RAD51 impaired cells (Higgs et al., 2015; Wang et al., 2015). Importantly, extending previous reports, we show that MRE11 and DNA2 both are responsible for degrading stalled replication forks in fork protection defective cells, including BOD1L and BRCA2. We conclude that C5 suppresses the fork protection defect of the BRCA2- or BOD1L-deficient cells by inhibition of DNA2. Taken together, the data shows that C5 is a specific inhibitor of DNA2 activities at stalled replication forks in vivo.

G. C5 Sensitizes Cells to PARP Inhibitors

Figure 7A:
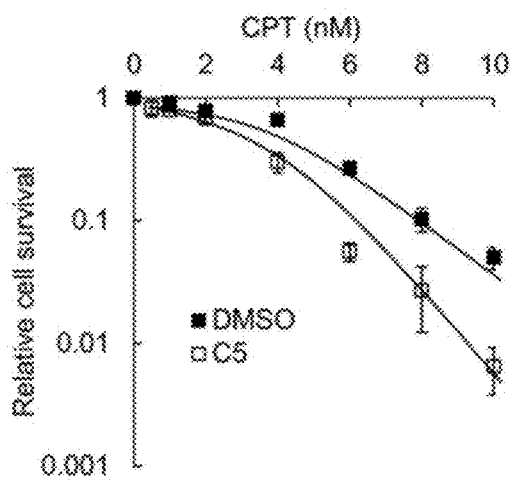
FIGS. 7A-7C. DNA2 inhibitor C5 synergistically kills breast cancer cells MCF7 with CPT and PARP inhibitor MK4827.

To test our hypothesis that inhibition of DNA2 synergizes with other chemotherapeutic agents, we treated cells with CPT and C5. We found the two agents to be synergistic for cellular lethality (FIG. 7A). These data uncover the potential for C5 in increasing killing efficiencies of DNA damaging chemotherapeutics.

Figure 7B:
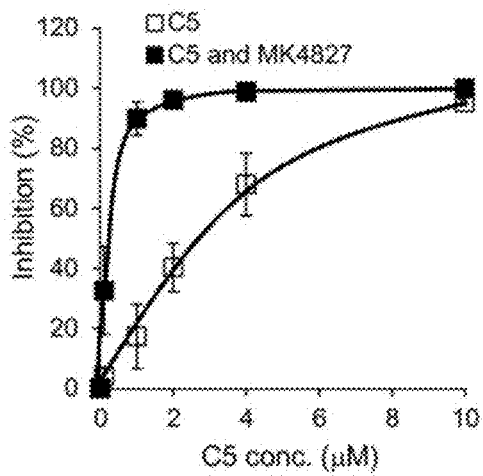
Figure 7C:
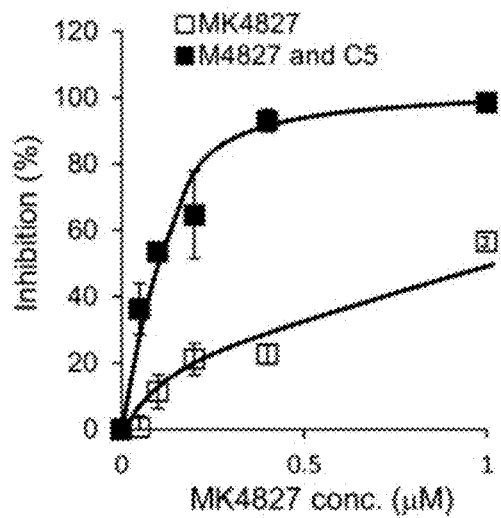

PARPs have been shown to play an important role in DNA single-strand break (SSB) repair and at stalled replication forks (Bryant et al., 2009; Hu et al., 2014; Yang et al., 2004; Ying et al., 2012), and inhibition of PARPs resulted in accumulation of SSBs and consequent DSBs in the cells (Fisher et al., 2007; Okano et al., 2003). More recently, PARPs have also been implicated in loading DNA damage response proteins to DSB sites (Hu et al., 2014; Li and Yu, 2013). Because DNA2 appears to function in many of the same pathways as the BRCA breast cancer genes, including DSB repair and replication fork protection, and PARP inhibition shows synthetic lethality with BRCA1 or BRCA2 mutants (Fathers et al., 2012; Fong et al., 2008), we considered that PARP inhibition might increase the effectiveness of the DNA2 inhibitor. To test this hypothesis, we determined the survival of MCF7 breast cancer cells cultured in the medium containing compound C5 and/or a MK4827, a PARP inhibitor (Jones et al., 2009). We found that MK4827 and C5 had a strong synergistic effect in inhibiting the survival of MCF7 cells (FIGS. 7B and 7C). The IC50 for MK4827 and C5 was 0.8 µM and 1.9 µM. The combination index for MK4827 (1 µM) and C5 (2 µM) was 0.13, indicating a very strong synergy between two drugs. These data support a model where DNA2 and PARP collaboratively participate or have complementary roles in DNA damage response, DSB repair, BER repair pathways, and replication fork protection, which will be an important issue to dissect in future studies.

H. Discussion

We have used a partial DNA2 protein structure based on the homology between the helicase domain of DNA2 and yeast Upf1-RNA U15 complex and human Upf1-ADP complex (Chakrabarti et al., 2011; Cheng et al., 2007) to identify 3 well defined pockets (Sites 1, 2, and 3), where drug like molecules can preferentially dock. We then used a virtual screen consisting of docking of 260,721 NCI deposited small molecules to these sites to identify DNA2 inhibitors. This screen is similar to a previous virtual screen used to identify inhibitors of ribonucleotide reductase (Chen et al., 2015; Zhou et al., 2013). We characterized one inhibitor, C5, which we demonstrate biochemically inhibits nuclease, DNA dependent ATPase, helicase, and DNA binding activities of DNA2. Through a series of functional analyses, we have pinpointed the specific functions of DNA2 that C5 targets to explain its cellular toxicity. C5 suppresses replication-coupled DSB end resection and restart of either HU- or CPT-stalled DNA replication forks. C5 also inhibits over-resection of nascent DNA in cells defective in replication fork protection, such as BRCA2. All these data support our conclusion that virtual screening can be efficient, and that C5 is a promising lead compound to develop sensitizers for cancer chemotherapeutics that cause replication stress.

It is interesting to note that C5, which our model and data suggest binds to the helicase domain of DNA2, can suppress the nuclease activity. We propose that this occurs because C5 can reduce DNA substrate binding to a site in the helicase domain necessary to activate the nuclease. The dramatic effect of the inhibitor on the nuclease activity, its predicted binding site, and more importantly, the effect of mutations we identified in helicase domain 1A on the nuclease activity and DNA binding reveal that the DNA binding site in helicase domain 1A (counterintuitively) is indeed critical for nuclease activity. This in turn suggests that DNA contacts in the nuclease site are not sufficiently strong to promote nuclease activity; multiple domains of DNA2 have to interact with DNA to elicit nuclease activity. These major new insights into the structure/function mechanism of this important class of enzyme, fused helicase/nuclease (including AddAB and RecB), extend recent reports on the X-ray crystal structure of murine DNA2 (80% identity to human DNA2 in the helicase domain)(Zhou et al., 2015). The structure shows DNA threading through a tunnel in the enzyme, first contacting the nuclease. The helicase domain follows and binding occurs as domain 1A and then 2A contact the DNA in the tunnel (Zhou et al., 2015). This explains why both nuclease and helicase utilize threading mechanisms (Bae et al., 2002; Balakrishnan et al., 2010; Kao et al., 2004a). Our work in turn provides direct evidence for requirement for both these domains for nuclease and helicase activity. Taken together with previous biochemical studies (Bae et al., 2002; Balakrishnan et al., 2010; Kao et al., 2004a; Stewart et al., 2010), a "thread, bind, and cleave" model now best explains how DNA2 nuclease works. C5 could either block threading, so that domain 1A does not come into contact with DNA or C5 could block binding to 1A or 2A. While we know about the active sites, the inhibitor will be useful in studying the role of the helicase, which is still conjectural. Co-crystals of DNA2 with C5 should be very informative with respect to the mechanism we propose for C5 function based on the putative binding to Site 1 in our homology structure. The putative common DNA binding site, predicted by our results and shown in the crystal structure, explains how the nuclease and helicase compete for the same substrate, as proposed by Levikova et al (Levikova et al., 2013) and that the nuclease catalytic site contacts must be disrupted for helicase to be active when duplex DNA is encountered. Therefore, in addition to possible therapeutic uses, the C5 inhibitor and well-designed derivatives will be valuable in future studies of how the helicase and nuclease activities are co-regulated and integrated.

This study of C5 adds cogent support to more circumstantial evidence that has accumulated that a major, and not minor, function of DNA2 both in yeast and human is to participate in the protection, remodeling and restart of stalled replication forks. We first reported this when we showed, using 2D gels, that yeast dna2-1 mutants led to replication fork collapse or remodelling into intermediates thought to be chi-structured (recombination) intermediates or reversed forks and DSBs, when replication forks stalled at the endogenous FOB 1 protein-mediated replication fork barrier in the rDNA (Weitao et al., 2003a; Weitao et al., 2003c). In *S. pombe*, furthermore, it was shown that DNA2 was acted on by the checkpoint to prevent fork collapse upon stalling at a similar barrier (Hu et al., 2012). More recently, human DNA2 has been shown in elegant DNA spreading experiments using knockdowns to be crucial for restart of forks stalled by CPT and specifically to promote limited resection necessary for restart (Thangavel et al., 2015). This activity must be tightly controlled, however, because the restoration of fork protection by inhibition of DNA2 in both BRCA2- and BOD1L depleted cells, at very low levels of the DNA2 inhibitor C5 (20 µM) and to the same extent as knockdown of DNA2 (FIGS. 6A-6D) if not properly regulated, over-resection by DNA2 can lead to excessive fork degradation and genome instability (Higgs et al., 2015; Wang et al., 2015). This coincides with the demonstration that depletion of DNA2 can suppress the cisplatin sensitivity of FANCD2$^{-/-}$ cells. By contrast to these replication functions, we found that higher levels of C5 were required to achieve the same level of inhibition as by knockdown of DNA2 (FIGS. 5A-5H) when measuring SSA and HR in the GFP reporter assays, which are not thought to depend on on-going replication, Until this study, there were no known small molecule inhibitors of DNA2. Discovering and testing additional DNA2 inhibitors will not only be invaluable for characterizing the integrated DNA2 enzymatic activities but will also enhance the preparation of advanced inhibitors for anticancer regimens, either alone or in combination with other chemotherapeutics. Importantly, chemical inhibition of DNA2 displayed cytotoxicity to DNA2-proficient mouse and human cells but not toward dna2$^{-/-}$ MES DNA2-deficient cells of human cells after DNA2 knockdown, supporting the assertion that we have found a DNA2-specific inhibitor. The use of inhibitors plus mutations to elucidate the mechanism of DNA2 nuclease/helicase activation as a basis for understanding its regulation in vivo is critical to design new therapeutic regimens. Inhibitors allow one to monitor the acute response of cells to the absence of DNA2, which is an important distinction from genetic studies, whose interpretation is always made difficult when studying essential genes such as DNA2. In the current study, we tested if targeting DNA2 may exploit a specific vulnerability in the cancer cells, assuming that normal cells are better protected by intact checkpoints and redundant repair processes.

We also tested the possible potentiation of PARP inhibitors by DNA2 inhibitor C5, because previous work suggested that DNA2 and PARP might participate in overlapping repair and replication stress response pathways (Bryant et al., 2009; Wanrooij and Burgers, 2015; Yang et al., 2004; Ying et al., 2012). PARP inhibitors have proved promising in treating BRCA-deficient tumors but fall short in that many such tumors are resistant. We tested if DNA2 might be partially responsible by performing a complementary function using the C5 DNA2 inhibitor. Indeed, C5 potentiated PARPi and vice versa. This "synthetic lethality" suggests novel approaches to applications of PARPi therapy. It also increases confidence that DNA2 and PARP function in response to replication stress that might occur in response to oncogene activation or treatment with DNA damaging agents such as CPT. Our demonstration of the stimulation of PARP inhibition by C5 may suggest that DNA2 plays a complementary role with PARP at stalled replication forks, where PARP has been shown to mediate replication fork restart in conjunction with MRE11, a nuclease that acts upstream of DNA2 in resection functions (Bryant et al., 2009; Shibata et al., 2014). In sum, the data presented here show that DNA2 inhibitors sensitize cancer cells to DNA damaging agents and additional agents used in current therapy and therefore may be feasible anti-cancer agents.

DNA2 is required for efficient telomere replication and repair. This is one way in which C5 and derivatives thereof may work. Additionally, DNA2 is also involved in telomere homeostasis, both in resection and in Okazaki fragment processing. Since 85% of tumor cells regenerate telomerase, there is some interest in telomerase inhibitors to fight cancer. An inhibitor of DNA2, such as for example the compounds described herein, might counteract the tumor's ability to make telomeres and therefore survive.

The generation of 3' G strand overhangs at telomere ends may play a role in regulating telomerase action and occurs by still unclear mechanisms. We show by an inducible short telomere assay that Sae2 and the Sgs1 RecQ helicase control two distinct but partially complementary pathways for nucleolytic processing of *S. cerevisiae* telomeres, with Sae2 function requiring its serine 267 phosphorylation. No processing activity is detectable in sae2Delta sgs1Delta cells, while the Exo1 exonuclease contributes to telomere end processing and elongation in both sae2Delta and sgs1Delta cells, suggesting that Exo1 telomeric function requires either Sgs1 or Sae2 action. Moreover, Dna2 might also support Sgs1 activity, as it acts redundantly with Exo1, but not with Sgs1. Finally, both length maintenance and G strand overhang generation at native telomeres are affected in sae2Delta sgs1Delta cells, further supporting the notion that Sae2 and Sgs1 combined activities control telomere length by regulating telomere processing.

I. Experimental Methodology

Protein Purification and Nuclease Activity Assay.

All WT and mutant DNA2 proteins in this study were expressed as 3× Flag-tagged recombinant proteins in 293T cells and were purified using affinity chromatography as previously described (Ronchi et al., 2013). The nuclease assay was conducted as previously described (Zheng et al., 2008).

ATPase Assays and EMSA Assays.

The ATPase assay was conducted as previously described (Masuda-Sasa et al., 2006). WT DNA2 nuclease cleaves the DNA substrate, which makes it technically difficult to display the helicase and ATPase activities. We therefore chose to use the D294A mutant, which is defective in nuclease activity but has similar ATPase activity to WT DNA2, to test the inhibitory effects of C5 (Masuda-Sasa et al., 2006). The EMSA was performed as described previously (Hellman and Fried, 2007).

Inhibition Mode and Nonlinear Regression to Determine the Inhibitor Ki.

For different concentrations of substrate, we increased the enzyme concentration in the same ratio to obtain the precise relative mean velocity, using 0.5 nM, 1.5 nM, 2.5 nM, 5 nM DNA2 for 5 nM, 15 nM, 25 nM, 50 nM substrates, respectively. For analysis of competitive inhibition, the Lineweaver-Burk plot was used with various concentrations of substrate and inhibitor. At a given substrate concentration, apparent inhibition constants of the inhibitor ($IC50_{observ}$) were derived from fit of the data to Eq 1, $$\text{fraction inhibition} = \frac{[I]}{IC50_{obsev} + [I]} \quad (1)$$

The inhibition constant $K_i$, which describes inhibitor binding to DNA2 in the absence of substrates, is related to observed $IC_{50}$ values by equation (2), $$IC50_{obsev} = K_i \left(1 + \frac{[S]}{K_M}\right) \quad (2)$$

in which KM is the Michaelis constant for the substrate. At limiting substrate concentrations, the $IC50_{observ}$ values approaches $K_i$. Thus, the $K_i$ value is obtained from extrapolation of the [S]-dependence of $IC50_{observ}$.

Cell Culture, Measurement of IC50, Clonogenic Assay, and Cell Proliferation Assay.

Cancerous and non-cancerous cells were cultured based on the culture instructions from the American Type Culture Collection (ATCC). Chemical compounds for the candidate DNA2 inhibitors were requested from NCI DTP (http://dtp.nci.nih.gov/). CPT was purchased from Sigma (St. Louis, Mo., purity >99%) and MK4827 was from MedChem Express (Monmouth Junction, N.J.). The cell survival rate of MES or human cancer cells under different treatments was measured by clonogenic assays following a published protocol (Franken et al, 2006). Briefly, 500 cells were seeded in a 6-well plate and incubated in culture medium containing DMSO or drugs, fresh medium with or without C5 for the cultured cells was changed every 3-4 days. For clonogenic assay, the plate was washed with PBS buffer after 14 days of culture and the colonies were fixed and stained with crystal violet solution and the number of colonies (>50 cells) was counted. The combination index, indicating the synergistic effect of the compounds, was measured following a previously published method (Chou, 2010). To measure the IC50 with the proliferation assay, 1,000-2,000 cells were seeded in a 96-well plate and incubated in culture medium containing DMSO or drugs, fresh medium with or without C5 for the cultured cells was changed every three days. After six days, the CellTiter 96 One Solution Reagent (Promega, Madison, Wis.) was added to the culture medium to measure the viable cells and the absorbance at 490 nm (A490), which is positively correlated to the number of cells, in each well was measured. The relative number of viable cells in the untreated control group was arbitrarily set as 1, and the relative number of viable cells in a C5-treated well was calculated by dividing its A490 by that of the control well.

Immunofluorescence Staining.

Cells (on cover-slips) with or without various drug treatments for 24 h were fixed with 4% paraformaldehyde, permeabilized with 0.1% Triton X100, blocked with the Image iT FX signal enhancer (Invitrogen), and incubated (1.5 h, room temperature) with the indicated primary antibodies. The antibodies against γ-H2AX and phosphorylated RPA2 were from Sigma Aldrich. The cells were then washed with PBS buffer and incubated (1 h, room temperature) with the corresponding secondary antibodies (1:200, Invitrogen). The slides were then washed with PBS buffer, counter stained with DAPI and analyzed with a fluorescence microscope (Olympus AX70).

DSB Repair Reporter Assays.

HDR-GFP and SSA-GFP were integrated in U2OS cells (Gunn and Stark, 2012; Howard et al., 2015). The U2OS cells were transfected with the I-sceI expression vector, or the empty vector and GFP vector as negative and positive controls, respectively. At 3 hours after transfection, we changed the culture medium to fresh medium with or without compound C5, and cultured the cells for 3 more days. The cells were harvested and the GFP+ frequencies (repair frequencies) were determined by flow cytometry using a CyAn ADP Analyzer (Beckman Coulter, Inc.).

Establishment of DNA2 Knockout ES Cells.

To construct the knockout vector for the mouse DNA2 allele, two DNA fragments corresponding to the mouse DNA2 gene were inserted into the poly-linker A and B, respectively, on the gene targeting vector, PKO scrambler NTK (Invitrogen, Carlsbad, Calif.) containing a neomycin or puromycin selection marker. One DNA fragment (5' arm) covered DNA sequences from intron 1 to intron 3 of the mouse DNA2 gene, and the other DNA fragment (3' arm) corresponded to DNA sequences from intron 7 to intron 12 of the mouse DNA2 gene. The knockout vector (neomycin) was electroporated into embryonic stem cells of the 129S1 genetic background. Recombination between the knockout vector and the WT DNA2 allele resulted in a mutant DNA2 allele, which deletes the exons 4-7 and disrupts the mouse DNA2 gene. DNA2+/−ES cells were selected by neomycin marker and confirmed with Southern blotting analysis. A second DNA2 knockout vector (puromycin) was electroporated into the DNA2+/−ES cells and DNA2−/−ES cells were selected by both neomycin and puromycin markers and confirmed with Southern blotting and PCR analysis DNA Fiber Assay.

DNA fibers performed and the data were analyzed as described previously (Schwab & Niedzwiedz, 2011; Techer et al, 2013; Thangavel et al, 2015). Briefly, A549 cells with or without DNA2 inhibition by C5 or siDNA2 were pre-incubated with 50 µM IdU for 40 min, left untreated or treated with indicated drugs in IdU medium, and then incubated with 250 µM CldU for 40 min. The cells were then collected and suspended in ice-cold PBS at $7.5 \times 10^5$ cells/ml.

The labeled cells (2 μl) were dropped on a glass slide and waited for 5 min to partially dry, and then lysed with 7 μl of lysis buffer (0.5% SDS in 200 mM Tris-HCl, pH 7.4, and 50 mM EDTA) for 2 min. The slides were tilted ~15° to allow DNA fiber spreads. After drying, the slides were fixed in 3:1 methanol/acetic acid for 10 min. The DNA was then denatured in 2.5 M HCl for 80 min, followed by PBS washes for 15 min (triple), and the slides were blocked with 5% BSA for 30 min. The slides were then incubated with 1:50 rat anti-BrdU (Abcam, clone BU1/75 (ICR1), for detection of CldU) followed by 1:50 mouse anti-BrdU (BD Biosciences, clone B44, for detection of IdU) for 1 hour. After incubation with the primary antibodies and extensive washes, slides were incubated with 1:200 Alexa Fluor 488-conjugated anti-rat (Life Technologies) and Alexa Fluor 555 anti-mouse (Life Technologies) for 1 h. Next, the slides were mounted with ProLong Gold Antifade reagent (Life Technologies). Images were taken with a Zeiss AxioCam 506 Mono microscope.

REFERENCES

Bae, S.-H., Kim, D. W., Kim, J., Kim, J.-H., Kim, D.-H., Kim, H.-D., Kang, H.-Y., and Seo, Y.-S. (2002). Coupling of DNA helicase and endonuclease activities of yeast Dna2 facilitates Okazaki fragment processing. J Biol Chem 277, 26632-26641. Bae, S. H., Bae, K.-H., Kim, J. A., and Seo, Y. S. (2001). RPA governs endonuclease switching during processing of Okazaki fragments in eukaryotes. Nature 412, 456-461. Balakrishnan, L., Polaczek, P., Pokharel, S., Campbell, J. L., and Bambara, R. A. (2010). Dna2 exhibits a unique strand end-dependent helicase function. J Biol Chem 285, 38861-38868. Begg, A. C., Stewart, F. A., and Vens, C. (2011). Strategies to improve radiotherapy with targeted drugs. Nature reviews Cancer 11, 239-253. Bryant, H. E., Petermann, E., Schultz, N., Jemth, A. S., Loseva, O., Issaeva, N., Johansson, F., Femandez, S., McGlynn, P., and Helleday, T. (2009). PARP is activated at stalled forks to mediate Mre11-dependent replication restart and recombination. The EMBO journal 28, 2601-2615. Budd, M. E., and Campbell, J. L. (1995). A new yeast gene required for DNA replication encodes a protein with homology to DNA helicases. Proc Natl Acad Sci USA 92, 7642-7646. Budd, M. E., and Campbell, J. L. (1997). A yeast replicative helicase, Dna2 helicase, interacts with yeast FEN-1 nuclease in carrying out its essential function. Mol Cell Biol 17, 2136-2142. Budd, M. E., and Campbell, J. L. (2000). The pattern of sensitivity of yeast dna2 mutants to DNA damaging agents suggests a role in DSB and postreplication repair pathways. Mutation research 459, 173-186. Budd, M. E., and Campbell, J. L. (2009). Interplay of Mre11 nuclease with Dna2 plus Sgs1 in Rad51-dependent recombinational repair. PLoS one 4, e4267. Budd, M. E., Tong, A. H., Polaczek, P., Peng, X., Boone, C., and Campbell, J. L. (2005). A Network of Multi-Tasking Proteins at the DNA Replication Fork Preserves Genome Stability. PLoS genetics 1, 634-650. Cejka, P., Cannavo, E., Polaczek, P., Masuda-Sasa, T., Pokharel, S., Campbell, J. L., and Kowalczykowski, S. C. (2010). DNA end resection by Dna2-Sgs1-RPA and its stimulation by Top3-Rmil and Mre11-Rad50-Xrs2. Nature 467, 112-116. Chakrabarti, S., Jayachandran, U., Bonneau, F., Fiorini, F., Basquin, C., Domcke, S., Le Hir, H., and Conti, E. (2011). Molecular mechanisms for the RNA-dependent ATPase activity of Upf1 and its regulation by Upf2. Molecular cell 41, 693-703. Chen, M. C., Zhou, B., Zhang, K., Yuan, Y. C., Un, F., Hu, S., Chou, C. M., Chen, C. H., Wu, J., Wang, Y., et al. (2015). The Novel Ribonucleotide Reductase Inhibitor COH29 Inhibits DNA Repair In Vitro. Mol Pharmacol 87, 996-1005. Cheng, Z., Muhlrad, D., Lim, M. K., Parker, R., and Song, H. (2007). Structural and functional insights into the human Upf1 helicase core. EMBO J 26, 253-264. Chou, T. C. (2010). Drug combination studies and their synergy quantification using the Chou-Talalay method. Cancer Res 70, 440-446. Duxin, J. P., Dao, B., Martinsson, P., Rajala, N., Guittat, L., Campbell, J. L., Spelbrink, J. N., and Stewart, S. A. (2009). Human Dna2 is a nuclear and mitochondrial DNA maintenance protein. Molecular and cellular biology 29, 4274-4282. Duxin, J. P., Moore, H. R., Sidorova, J., Karanja, K., Honaker, Y., Dao, B., Piwnica-Worms, H., Campbell, J. L., Monnat, R. J., and Stewart, S. A. (2012). Okazaki fragment processing-independent role for human Dna2 during DNA replication. J Biol Chem, 21980-21991. Fathers, C., Drayton, R. M., Solovieva, S., and Bryant, H. E. (2012). Inhibition of poly(ADP-ribose) glycohydrolase (PARG) specifically kills BRCA2-deficient tumor cells. Cell Cycle 11, 990-997. Fisher, A. E., Hochegger, H., Takeda, S., and Caldecott, K. W. (2007). Poly(ADP-ribose) polymerase 1 accelerates single-strand break repair in concert with poly(ADP-ribose) glycohydrolase. Mol Cell Biol 27, 5597-5605. Fong, Y., Chou, S. J., Hung, K. F., Wu, H. T., and Kao, S. Y. (2008). An investigation of the differential expression of Her2/neu gene expression in normal oral mucosa, epithelial dysplasia, and oral squamous cell carcinoma in Taiwan. Journal of the Chinese Medical Association: JCMA 71, 123-127. Gunn, A., and Stark, J. M. (2012). I-SceI-based assays to examine distinct repair outcomes of mammalian chromosomal double strand breaks. Methods in molecular biology 920, 379-391. Hashimoto, Y., Chaudhuri, A. R., Lopes, M., and Costanzo, V. (2010). Rad51 protects nascent DNA from Mre11-dependent degradation and promotes continuous DNA synthesis. Nature structural & molecular biology 17, 1305-1311. Hellman, L. M., and Fried, M. G. (2007). Electrophoretic mobility shift assay (EMSA) for detecting protein-nucleic acid interactions. Nature protocols 2, 1849-1861. Higgs, M. R., Reynolds, J. J., Winczura, A., Blackford, A. N., Borel, V., Miller, E. S., Zlatanou, A., Nieminuszczy, J., Ryan, E. L., Davies, N. J., et al. (2015). BOD1L Is Required to Suppress Deleterious Resection of Stressed Replication Forks. Molecular cell 59, 462-477. Hoa, N. N., Kobayashi, J., Omura, M., Hirakawa, M., Yang, S. H., Komatsu, K., Paull, T. T., Takeda, S., and Sasanuma, H. (2015). BRCA1 and CtIP Are Both Required to Recruit Dna2 at Double-Strand Breaks in Homologous Recombination. PLoS one 10, e0124495. Howard, S. M., Yanez, D. A., and Stark, J. M. (2015). DNA damage response factors from diverse pathways, including DNA crosslink repair, mediate alternative end joining. PLoS Genet 11, e1004943. Hsiang, Y. H., Lihou, M. G., and Liu, L. F. (1989). Arrest of replication forks by drug-stabilized topoisomerase I-DNA cleavable complexes as a mechanism of cell killing by camptothecin. Cancer Res 49, 5077-5082. Hu, J., Sun, L., Shen, F., Chen, Y., Hua, Y., Liu, Y., Zhang, M., Hu, Y., Wang, Q., Xu, W., et al. (2012). The intra-s phase checkpoint targets dna2 to prevent stalled replication forks from reversing. Cell 149, 1221-1232. Hu, Y., Petit, S. A., Ficarro, S. B., Toomire, K. J., Xie, A., Lim, E., Cao, S. A., Park, E., Eck, M. J., Scully, R., et al. (2014). PARPi-driven poly-ADP-ribosylation regulates BRCA1 function in homologous recombination-mediated DNA repair. Cancer discovery 4, 1430-1447. Imamura, O., and Campbell, J. L. (2003). The human Bloom syndrome gene suppresses the DNA replication and repair defects of yeast dna2 mutants. Proc Natl Acad Sci USA 100, 8193-8198. Jones, P., Altamura, S., Boueres, J., Ferrigno, F., Fonsi, M., Giomini, C., Lamartina, S., Monteagudo, E., Ontoria, J. M., Orsale, M. V., et al. (2009). Discovery of 2-{4-[(3 S)-piperidin-3-yl] phenyl}-2H-indazole-7-carboxamide (MK-4827): a novel oral poly (ADP-ribose)polymerase (PARP) inhibitor efficacious in BRCA-1 and -2 mutant tumors. Journal of medicinal chemistry 52, 7170-7185. Kang, J.-Y., Choi, E., Bae, S.-H., Lee, K.-H., Gim, B.-S., Kim, H.-D., Park, C., MacNeill, S. A., and Seo, Y.-S. (2000). Genetic analyses of *Schizosaccharomyces pombe* dna2+ reveal that Dna2 plays an essential role in Okazaki fragment metabolism. Genetics 155, 1055-1067. Kang, Y. H., Lee, C. H., and Seo, Y. S. (2010). Dna2 on the road to Okazaki fragment processing and genome stability in eukaryotes. Crit Rev Biochem Mol Biol 45, 71-96. Kao, H.-I., Campbell, J. L., and Bambara, R. A. (2004a). Dna2p helicase/nuclease is a tracking protein, like FEN1, for flap cleavage during Okazaki fragment maturation. J Biol Chem 279, 50840-50849. Kao, H. I., Veeraraghavan, J., Polaczek, P., Campbell, J. L., and Bambara, R. A. (2004b). On the roles of *Saccharomyces cerevisiae* Dna2p and FEN1 in Okazaki fragment processing. J Biol Chem 279, 15014-15024. Karanja, K. K., Lee, E. H., Hendrickson, E. A., and Campbell, J. L. (2014). Preventing over-resection by DNA2 helicase/nuclease suppresses repair defects in Fanconi anemia cells. Cell Cycle 13, 1540-1550. Karanja, K. K., S. W., C., Duxin, J. P., Stewart, S. A., and Campbell, J. L. (2012). DNA2 and EXO1 in Replication-coupled Homology Directed Repair and in the Interplay Between HDR and the F A/BRCA Network. Cell Cycle 11, 3983-3996. Kim, D.-H., Lee, K.-H., Kim, J.-H., Ryu, G.-H., Bae, S.-H., Lee, B.-C., Moon, K.-Y., Byun, S.-M., Koo, H.-S., and Seo, Y.-S. (2005). Enzymatic properties of the *Caenorhabditis elegans* Dna2 endonuclease/helicase and a species-specific interaction between RPA and Dna2. Nucl Acids Res 33, 1372-1383. Kumar, S., and Burgers, P. M. (2013). Lagging strand maturation factor Dna2 is a component of the replication checkpoint initiation machinery. Genes & development 27, 313-321. Lai, M. S., and Foiani, M. (2012). Dna2 offers support for stalled forks. Cell 149, 1181-1183. Le Tourneau, C., Stathis, A., Vidal, L., Moore, M. J., and Siu, L. L. (2010). Choice of starting dose for molecularly targeted agents evaluated in first-in-human phase I cancer clinical trials. Journal of clinical oncology: official journal of the American Society of Clinical Oncology 28, 1401-1407. Levikova, M., Klaue, D., Seidel, R., and Cejka, P. (2013). Nuclease activity of *Saccharomyces cerevisiae* Dna2 inhibits its potent DNA helicase activity. Proc Natl Acad Sci USA, E1992-2001. Li, M., and Yu, X. (2013). Function of BRCA1 in the DNA damage response is mediated by ADP-ribosylation. Cancer Cell 23, 693-704. Liao, S., Toczylowski, T., and Yan, H. (2008). Identification of the *Xenopus* DNA2 protein as a major nuclease for the 5'→3' strand-specific processing of DNA ends. Nucleic Acids Res 36, 6091-6100. Liao, S., Toczylowski, T., and Yan, H. (2011). Mechanistic analysis of *Xenopus* EXO1's function in 5'-strand resection at DNA double-strand breaks. Nucleic Acids Res 39, 5967-5977. Lin, W., Sampathi, S., Dai, H., Liu, C., Zhou, M., Hu, J., Huang, Q., Campbell, J., Shin-Ya, K., Zheng, L., et al. (2013). Mammalian DNA2 helicase/nuclease cleaves G-quadruplex DNA and is required for telomere integrity. The EMBO journal 32, 1425-1439. Masuda-Sasa, T., Imamura, O., and Campbell, J. L. (2006). Biochemical analysis of human Dna2. Nucleic acids research 34, 1865-1875. Masuda-Sasa, T., Polaczek, P., Peng, X. P., Chen, L., and Campbell, J. L. (2008). Processing of G4 DNA by Dna2 Helicase/nuclease and RPA provides insights into the mechanism of Dna2/RPA substrate recognition. J Biol Chem 283, 24359-24373. Nimonkar, A. V., Genschel, J., Kinoshita, E., Polaczek, P., Campbell, J. L., Wyman, C., Modrich, P., and Kowalczykowski, S. C. (2011). BLM-DNA2-RPA-MRN- and EXO1-BLM-RPA-MRN constitute two DNA end resection machineries for human DNA break repair. Genes & development 25, 350-362. Niu, H., Raynard, S., and Sung, P. (2009). Multiplicity of DNA end resection machineries in chromosome break repair. Genes & development 23, 1481-1486. Okano, S., Lan, L., Caldecott, K. W., Mori, T., and Yasui, A. (2003). Spatial and temporal cellular responses to single-strand breaks in human cells. Mol Cell Biol 23, 3974-3981. Patel, A. G., Flatten, K. S., Schneider, P. A., Dai, N. T., McDonald, J. S., Poirier, G. G., and Kaufmann, S. H. (2012). Enhanced killing of cancer cells by poly(ADP-ribose) polymerase inhibitors and topoisomerase I inhibitors reflects poisoning of both enzymes. J Biol Chem 287, 4198-4210. Peng, G., Dai, H., Zhang, W., Hsieh, H. J., Pan, M. R., Park, Y. Y., Tsai, R. Y., Bedrosian, I., Lee, J. S., Ira, G., et al. (2012). Human Nuclease/Helicase DNA2 Alleviates Replication Stress by Promoting DNA End Resection. Cancer research 72, 2802-2813. Petermann, E., Orta, M. L., Issaeva, N., Schultz, N., and Helleday, T. (2010). Hydroxyurea-stalled replication forks become progressively inactivated and require two different RAD51-mediated pathways for restart and repair. Molecular cell 37, 492-502. Pierce, A. J., Johnson, R. D., Thompson, L. H., and Jasin, M. (1999). XRCC3 promotes homology-directed repair of DNA damage in mammalian cells. Genes & development 13, 2633-2638. Ray Chaudhuri, A., Hashimoto, Y., Herrador, R., Neelsen, K. J., Fachinetti, D., Bermejo, R., Cocito, A., Costanzo, V., and Lopes, M. (2012). Topoisomerase I poisoning results in PARP-mediated replication fork reversal. Nature structural & molecular biology 19, 417-423. Ronchi, D., Di Fonzo, A., Lin, W., Bordoni, A., Liu, C., Fassone, E., Pagliarani, S., Rizzuti, M., Zheng, L., Filosto, M., et al. (2013). Mutations in DNA2 link progressive myopathy to mitochondrial DNA instability. Am J Hum Genet 92, 293-300. Schlacher, K., Christ, N., Siaud, N., Egashira, A., Wu, H., and Jasin, M. (2011). Double-strand break repair-independent role for BRCA2 in blocking stalled replication fork degradation by MRE11. Cell 145, 529-542. Schlacher, K., Wu, H., and Jasin, M. (2012). A Distinct Replication Fork Protection Pathway Connects Fanconi Anemia Tumor Suppressors to RAD51-BRCA1/2. Cancer cell 22, 106-116. Shaheen, R., Faqiih, E., Ansari, S., Abdel-Salam, G., Al-Hassnan, Z. N., Al-Shidi, T., Alomar, R., Sogaty, S., and Alkuraya, F. S. (2014). Genomic analysis of primorial dwarfism reveals novel disease genes. Genome Res 24, 291-299. Shibata, A., Moiani, D., Arvai, A. S., Perry, J., Harding, S. M., Genols, M.-M., Maity, R., Rossum-Fikkert, S.v., Kertokallo, A., Romoli, F., et al. (2014). DNA Double-Strand Break Repair Pathway Choice is Directed by Distinct MRE11 Nuclease Activities. Molecular cell 53, 7-18. Stewart, J. A., Campbell, J. L., and Bambara, R. A. (2010). Dna2 is a structure-specific nuclease, with affinity for 5'-flap intermediates. Nucleic Acids Res 38, 920-930. Stewart, J. A., Miller, A. S., Campbell, J. L., and Bambara, R. A. (2008). Dynamic removal of replication protein A by Dna2 facilitates primer cleavage during Okazaki fragment processing in *Saccharomyces cerevisiae*. J Biol Chem 283, 31356-31365. Strauss, C., Komowski, M., Benvenisty, A., Shahar, A., Masury, H., Ben-Porath, I., Ravid, T., Arbel-Eden, A., and Goldberg, M. (2014). The DNA2 nuclease/helicase is an estrogen-dependent gene mutated in breast and ovarian cancers. Oncotarget 5, 9396-9409. Sturzenegger, A., Burdova, K., Kanagaraj, R., Levikova, M., Pinto, C., Cejka, P., and Janscak, P. (2014). DNA2 cooperates with the WRN and BLM RecQ helicases to mediate long-range DNA end resection in human cells. J Biol Chem 289, 27314-27326. Symington, L. S., and Gautier, J. (2011). Double-Strand Break End Resection and Repair Pathway Choice. Annu Rev

What is claimed is:

1. A method of
   (i) sensitizing cancer cells to radiation therapy or chemotherapy;
   (ii) potentiating clinical efficacy of a PARP inhibitor or a topoisomerase inhibitor;
   (iii) inhibiting DNA replication;
   (iv) suppressing DNA double-strand break repair end resection, recombination, or over-resection of nascent DNA in cells defective in fork protection, and restart of stalled DNA replication forks in cells; or
   (v) interfering with telomere replication or repair; wherein
   the method comprising administering a compound or pharmaceutically acceptable salt thereof, wherein the compound is:

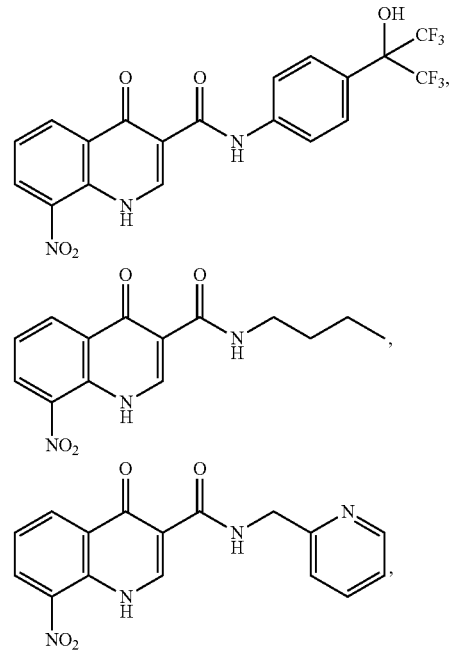

or a tautomer of any of the foregoing.

2. The method of claim 1, wherein the topoisomerase inhibitor is a topoisomerase I inhibitor.

3. The method of claim 1, further comprising administering a chemotherapeutic agent, radiation, or a combination thereof.

4. A method of treating Fanconi anemia in a patient in need thereof comprising administering to the patient a therapeutically effective amount of a compound or pharmaceutically acceptable salt thereof, wherein the compound is:

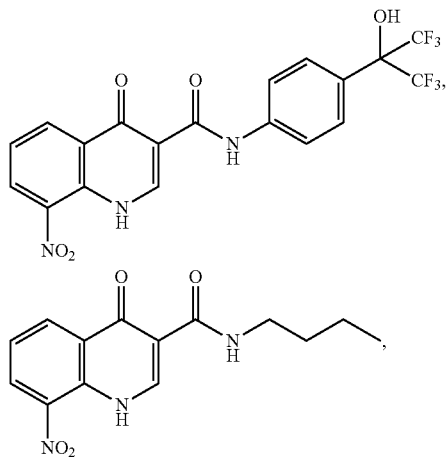

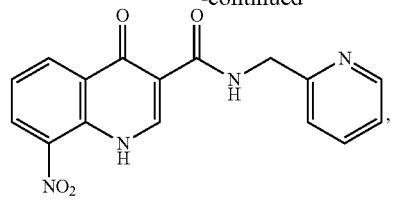

or a tautomer of any of the foregoing.

5. The method of claim 1, wherein the method is sensitizing cancer cells to radiation therapy or chemotherapy.

6. The method of claim 5, further comprising administering a chemotherapeutic agent, radiation, or a combination thereof.

7. The method of claim 1, wherein the method is inhibiting DNA replication.

8. The method of claim 7, further comprising further comprising administering a chemotherapeutic agent, radiation, or a combination thereof.

* * * * *